(12) United States Patent
Campana et al.

(10) Patent No.: US 12,404,491 B2
(45) Date of Patent: *Sep. 2, 2025

(54) METHODS FOR ENHANCING EFFICACY OF THERAPEUTIC IMMUNE CELLS

(71) Applicant: National University of Singapore, Singapore (SG)

(72) Inventors: Dario Campana, Singapore (SG); Takahiro Kamiya, Singapore (SG)

(73) Assignee: NATIONAL UNIVERSITY OF SINGAPORE, Singapore (SG)

(*) Notice: Subject to any disclaimer, the term of this patent is extended or adjusted under 35 U.S.C. 154(b) by 1284 days.

This patent is subject to a terminal disclaimer.

(21) Appl. No.: 16/943,400

(22) Filed: Jul. 30, 2020

(65) Prior Publication Data

US 2021/0046112 A1 Feb. 18, 2021

Related U.S. Application Data

(63) Continuation of application No. 15/548,577, filed as application No. PCT/SG2016/050063 on Feb. 5, 2016, now Pat. No. 10,765,699.

(Continued)

(51) Int. Cl.
*C12N 5/0783* (2010.01)
*A61K 40/11* (2025.01)
(Continued)

(52) U.S. Cl.
CPC ............ *C12N 5/0646* (2013.01); *A61K 40/11* (2025.01); *A61K 40/15* (2025.01); *A61K 40/31* (2025.01);
(Continued)

(58) Field of Classification Search
CPC ................ C12N 5/0646; C12N 5/0636; C12N 2510/00; A61K 40/11; A61K 40/15;
(Continued)

(56) References Cited

U.S. PATENT DOCUMENTS 4,946,778 A 8/1990 Ladner et al.
5,260,203 A 11/1993 Ladner et al.
(Continued)

FOREIGN PATENT DOCUMENTS

CA 2 937 157 A1 1/2018
CN 107709548 A 2/2018
(Continued)

OTHER PUBLICATIONS

Lanitis et al A Human ErbB2-Specific T-Cell Receptor Confers Potent Antitumor Effector Functions in Genetically Engineered Primary Cytotoxic Lymphocytes Human Gene Therapy 25:730-739 (Aug. 2014).*
(Continued)

*Primary Examiner* — Tracy Vivlemore
*Assistant Examiner* — Thomas R. Amick
(74) *Attorney, Agent, or Firm* — Wilson Sonsini Goodrich & Rosati

(57) ABSTRACT

The present invention relates to a method of using a receptor (e.g., chimeric antigen receptor—CAR) that activates an immune response upon binding a cancer cell ligand in conjunction with a target-binding molecule that targets a protein or molecule for removal or neutralization to generate enhanced anti-cancer immune cells. The present invention also relates to engineered immune cells having enhanced therapeutic efficacy and uses thereof.

23 Claims, 10 Drawing Sheets

Specification includes a Sequence Listing.

Related U.S. Application Data

(60) Provisional application No. 62/130,970, filed on Mar. 10, 2015, provisional application No. 62/112,765, filed on Feb. 6, 2015.

(51) Int. Cl.
  *A61K 40/15* (2025.01)
  *A61K 40/31* (2025.01)
  *A61K 40/42* (2025.01)
  *C07K 16/28* (2006.01)

(52) U.S. Cl.
  CPC ...... *A61K 40/4211* (2025.01); *A61K 40/4224* (2025.01); *C07K 16/2809* (2013.01); *C07K 16/2833* (2013.01); *C07K 16/289* (2013.01); *C12N 5/0636* (2013.01); *A61K 2239/48* (2023.05); *C07K 2319/03* (2013.01); *C12N 2510/00* (2013.01)

(58) Field of Classification Search
  CPC ................ A61K 40/31; A61K 40/4211; A61K 40/4224; A61K 2239/48; A61K 39/4611; A61K 39/4613; A61K 39/4631; A61K 39/464412; A61K 39/464429; C07K 16/2809; C07K 16/2833; C07K 16/289; C07K 2319/03; A61P 35/00; A61P 37/02
  See application file for complete search history.

(56) References Cited

U.S. PATENT DOCUMENTS

| | | |
|---|---|---|
| 7,887,805 B2 | 2/2011 | Pedersen et al. |
| 8,119,775 B2 | 2/2012 | Moretta |
| 8,399,645 B2 | 3/2013 | Campana et al. |
| 8,580,714 B2 | 11/2013 | Almagro et al. |
| 8,614,307 B2 | 12/2013 | Moretta et al. |
| 8,637,258 B2 | 1/2014 | Padkjaer et al. |
| 8,796,427 B2 | 8/2014 | Spee |
| 8,981,065 B2 | 3/2015 | Moretta et al. |
| 9,181,527 B2 | 11/2015 | Sentman |
| 9,273,283 B2 | 3/2016 | Sentman |
| 9,422,368 B2 | 8/2016 | Spee et al. |
| 9,683,042 B2 | 6/2017 | Lee et al. |
| 9,902,936 B2 | 2/2018 | Moretta et al. |
| 10,550,183 B2 | 2/2020 | Png et al. |
| 10,730,942 B2 | 8/2020 | Pule et al. |
| 10,765,699 B2 | 9/2020 | Campana et al. |
| 11,161,907 B2 * | 11/2021 | Powell ................. C12N 15/113 |
| 11,440,958 B2 | 9/2022 | Png et al. |
| 11,648,269 B2 | 5/2023 | Campana et al. |
| 11,679,132 B2 | 6/2023 | Campana et al. |
| 11,945,865 B2 | 4/2024 | Png et al. |
| 2005/0282181 A1 | 12/2005 | Yan et al. |
| 2006/0034834 A1 | 2/2006 | Marasco et al. |
| 2007/0036773 A1 | 2/2007 | Cooper et al. |
| 2009/0196850 A1 | 8/2009 | Romagne et al. |
| 2012/0282256 A1 | 11/2012 | Campana et al. |
| 2013/0266551 A1 | 10/2013 | Campana et al. |
| 2013/0287748 A1 | 10/2013 | June |
| 2014/0120622 A1 | 5/2014 | Gregory |
| 2014/0186387 A1 | 7/2014 | Lauer |
| 2016/0256488 A1 | 9/2016 | Wu |
| 2016/0312182 A1 | 10/2016 | Sentman |
| 2017/0335331 A1 | 11/2017 | Zhao et al. |
| 2018/0008638 A1 | 1/2018 | Campana |
| 2018/0066034 A1 | 3/2018 | Ma et al. |
| 2018/0086831 A1 | 3/2018 | Pule |
| 2019/0002912 A1 | 1/2019 | Lu et al. |
| 2019/0038733 A1 | 2/2019 | Campana et al. |
| 2019/0046571 A1 | 2/2019 | Campana et al. |
| 2019/0345217 A1 | 11/2019 | Ma et al. |
| 2020/0087398 A1 | 3/2020 | Qasim et al. |

FOREIGN PATENT DOCUMENTS

| | | |
|---|---|---|
| CN | 113713091 A | 11/2021 |
| CN | 107709548 B | 6/2022 |
| CN | 115029362 A | 9/2022 |
| EP | 0404097 A2 | 12/1990 |
| EP | 2247619 A1 | 11/2010 |
| EP | 3169773 A2 | 5/2017 |
| EP | 3322801 A1 | 5/2018 |
| EP | 3359168 A1 | 8/2018 |
| EP | 3474867 A1 | 5/2019 |
| EP | 3568467 A1 | 11/2019 |
| JP | H03219896 A | 9/1991 |
| JP | H09501824 A | 2/1997 |
| JP | 2001516766 A | 10/2001 |
| JP | 2004529610 A | 9/2004 |
| JP | 2008506368 A | 3/2008 |
| JP | 2008518021 A | 5/2008 |
| JP | 2009511495 A | 3/2009 |
| JP | 2010537671 A | 12/2010 |
| JP | 2011510047 A | 3/2011 |
| JP | 2014507118 A | 3/2014 |
| JP | 6895380 B2 | 6/2021 |
| JP | 2021137024 A | 9/2021 |
| WO | WO-8801649 A1 | 3/1988 |
| WO | WO-9311161 A1 | 6/1993 |
| WO | WO 99/14353 A2 | 3/1999 |
| WO | WO 2003/051926 A2 | 6/2003 |
| WO | WO-2005017163 A2 | 2/2005 |
| WO | WO 2006/003179 A2 | 1/2006 |
| WO | WO 2009/092805 A1 | 7/2009 |
| WO | WO 2012/079000 A1 | 6/2012 |
| WO | WO-2013126712 A1 | 8/2013 |
| WO | WO-2014011984 A1 | 1/2014 |
| WO | WO 2014/124143 A1 | 8/2014 |
| WO | WO-2014134165 A1 | 9/2014 |
| WO | WO-2014159940 A1 | 10/2014 |
| WO | WO 2015/075468 A1 | 5/2015 |
| WO | WO-2015121454 A1 | 8/2015 |
| WO | WO 2015/150771 A1 | 10/2015 |
| WO | WO 2016/055551 A1 | 4/2016 |
| WO | WO 2016/102965 A1 | 6/2016 |
| WO | WO 2016/126213 A1 | 8/2016 |
| WO | WO 2017/213979 A1 | 12/2017 |
| WO | WO 2018/027036 | 2/2018 |
| WO | WO-2019032916 A1 | 2/2019 |

OTHER PUBLICATIONS

Alanen et al., Beyond KDEL: the role of positions 5 and 6 in determining ER localization. J. Mol. Biol. (2011) 409, 291-297. Available online Apr. 6, 2011.

Alarcon et al., Assembly of the human T cell receptor-CD3 complex takes place in the endoplasmic reticulum and involves intermediary complexes between the CD3-gamma.delta.epsilon core and single T cell receptor alpha or beta chains, Journal of Biological Chemistry, Feb. 25, 1988;263(6):2953-61.

Almagro, Juan C., Fransson, Johan. Humanization of antibodies. Frontiers in Bioscience 13;1619-1633 (Jan. 1, 2008).

Altschul et al. Basic local alignment search tool. J Mol Biol 215(3):403-410 (1990).

Anti-CD3 epsilon [OKT-3 (muromonab)]. Absolute Antibody. Website. Copyright 2021. Retrieved Dec. 26, 2021 at URL: https://absoluteantibody.com/product/anti-cd3-epsilon-okt-3- . . . 4 pages.

Anti-CD3D monoclonal antibody, clone PLU4 (DCABH-10124). Product Information. CD Creative Diagnostics. Publication date unknown. 2 pages.

Anti-TCR [BMA031]. Absolute Antibody. Website. Copyright 2021. Retrieved Dec. 26, 2021 at URL: https://absoluteantibody.com/product/anti-tcr-bma031/ 4 pages.

Anwer et al., Donor origin CAR T cells: graft versus malignancy effect without GVHD, a systematic review, Immunotherapy, Jan. 2017;9(2):123-130.

Appelbaum. Haematopoietic cell transplantation as immunotherapy. Nature, vol. 411, pp. 385-389 (2001).

(56) References Cited

OTHER PUBLICATIONS

Arafat et al. Antineoplastic effect of anti-erbB-2 intrabody is not correlated with scFv affinity for its target. Cancer Gene Therapy, vol. 7, No. 9, 2000: pp. 1250-1256.
Arase et al. Recognition of virus infected cells by NK cells (w/ English abstract). Department of Immunochemistry, Research Institute for Microbial Diseases, Osaka University, vol. 54, No. 2, pp. 153-160 (2004).
Austyn et al. T cell activation by anti-CD3 antibodies: function of Fc receptors on B cell blasts, but not resting B cells, and CD18 on the responding T cells. Eur J Immunol 17:1329-1335 (1987).
Böldicke et al. Functional inhibition of transitory proteins by intrabody-mediated retention in the endoplasmatic reticulum. Methods 56 (2012) 338-350. Available online Oct. 20, 2011.
Bleakley et al., Molecules and mechanisms of the graft-versus-leukaemia effect, Nature Reviews, Cancer, May 2004;4(5):371-80.
Boettcher et al., Choosing the Right Tool for the Job: RNAi, TALEN, or CRISPR, Mol Cell. May 21, 2015;58:575-85.
Brentjens et al. CD19-targeted T cells rapidly induce molecular remissions in adults with chemotherapy-refractory acute lymphoblastic leukemia. Sci Transl Med. Mar. 20, 2013;5(177):177ra38. 9 pages.
Brentjens et al. Eradication of systemic B-cell tumors by genetically targeted human T lymphocytes co-stimulated by CD80 and interleukin-15. Nat Med. Mar. 2003;9(3):279-86.
Brentjens et al. Safety and persistence of adoptively transferred autologous CD19-targeted T cells in patients with relapsed or chemotherapy refractory B-cell leukemias. Blood. Nov. 3, 2011;118(18):4817-28. Prepublished online Aug. 17, 2011.
Brudno et al. Allogeneic T cells that express an anti-CD19 chimeric antigen receptor induce remissions of B-cell malignancies that progress after allogeneic hematopoietic stem-cell transplantation without causing graft-versus-host disease. J Clin Oncol 34(10):1112-1121 (2016).
Burns et al. Two monoclonal anti-human T lymphocyte antibodies have similar biologic effects and recognize the same cell surface antigen. J Immunol 1982; 129:1451-1457.
Campana et al. 4-1BB chimeric antigen receptors. Cancer J. Mar.-Apr. 2014;20(2):134-40.
Ceuppens et al. Failure of OKT3 monoclonal antibody to induce lymphocyte mitogenesis: a familial defect in monocyte helper function. J Immunol, vol. 134, No. 3, pp. 1498-1502 (Mar. 1985).
Chang et al. A chimeric receptor with NKG2D specificity enhances natural killer cell activation and killing of tumor cells. Cancer Res 73(6):1777-86 (Mar. 15, 2013). Published online Jan. 9, 2013.
Chen et al., Donor-derived CD19-targeted T cell infusion induces minimal residual disease-negative remission in relapsed B-cell acute lymphoblastic leukaemia with no response to donor lymphocyte infusions after haploidentical haematopoietic stem cell transplantation. British Journal of Haematology, 2017, 179, 598-605. Epub Oct. 26, 2017.
Clevers et al., The T cell receptor/CD3 complex: a dynamic protein ensemble, Annual Review of Immunology, 1988;6:629-62.
Cooley et al. Donor selection for natural killer cell receptor genes leads to superior survival after unrelated transplantation for acute myelogenous leukemia. Blood (2010) 116 (14): 2411-2419.
Cooper, et al. T-cell clones can be rendered specific for CD19: toward the selective augmentation of the graft-versus-B-lineage leukemia effect. Blood. Feb. 15, 2003;101(4):1637-44. Epub Oct. 10, 2002.
Co-pending U.S. Appl. No. 17/862,721, inventors Campana; Dario et al., filed Jul. 12, 2022.
Co-pending U.S. Appl. No. 17/862,797, inventors Campana; Dario et al., filed Jul. 12, 2022.
Dai et al., Tolerance and efficacy of autologous or donor-derived T cells expression CD19 chimeric antigen receptors in adult B-ALL with extramedullary leukemia. OncoImmunology, 4:11, e1027469 (2015). 12 pages.
Davila. Efficacy and toxicity management of 19-28z CAR T cell therapy in B cell acute lymphoblastic leukemia. Sci Transl Med 6(224):224ra25 (2014).

EP16746922.0 Extended European Search Report dated Sep. 21, 2018.
EP18844536.5 Extended European Search Report dated Mar. 18, 2021.
Eshhar et al. Specific activation and targeting of cytotoxic lymphocytes through chimeric single chains consisting of antibody-binding domains and the gamma or zeta subunits of the immunoglobulin and T-cell receptors. Proc Natl Acad Sci U S A, vol. 90, pp. 720-724 (Jan. 1993).
Eyquem et al., Targeting a CAR to the TRAC locus with CRISPR/Cas9 enhances tumour rejection, Nature. Mar. 2, 2017; 543(7643): 113-117.
Gale. Cellular and Molecular Basis of Cancer. Merck Manual Professional Version. Last full review/revision Nov. 2020. Content last modified Nov. 2020. Retrieved Jan. 8, 2021 at URL: https://www.merckmanuals.com/professional/hematology-and-oncology/overview-of-cancer/cellular-and-molecular-basis-of-cancer# 8 pages.
Gan et al. Molecular Mechanisms and Potential Therapeutic Reversal of Pancreatic Cancer-Induced Immune Evasion. Cancers 2020, 12, 1872. Published Jul. 11, 2020. 22 pages.
Gao et al. Retention mechanisms for ER and Golgi membrane proteins. Trends in Plant Science, vol. 19, Issue 8, pp. 508-515 (Aug. 2014).
Geiger et al. Integrated src kinase and costimulatory activity enhances signal transduction through single-chain chimeric receptors in T lymphocytes. Blood 98(8):2364-2371 (2001).
Geiger et al. The TCR zeta-chain immunoreceptor tyrosine-based activation motifs are sufficient for the activation and differentiation of primary T lymphocytes. The Journal of Immunology, 1999, 162: 5931-5939.
Ghosh et al., Donor CD19 CAR T cells exert potent graft-versus-lymphoma activity with diminished graft-versus-host activity, Nat Med. Feb. 2017 ; 23(2): 242-249.
Giebel et al. Survival advantage with KIR ligand incompatibility in hematopoietic stem cell transplantation from unrelated donors. Blood (2003) 102 (3): 814-819.
Grimshaw. Developing a universal T cell for use in adoptive immunotherapy (thesis), University College London (2015). Retrieved Aug. 22, 2022 at URL: http://discovery.ucl.ac.uk/1470207/1/Grimshaw%20Ben%20Thesis.pdf. 267 pages.
Grimshaw et al. Creating a Null T Cell for Adoptive Immunotherapy. Poster. Mar. 9, 2012. One page.
Grovender et al. Single-chain antibody fragment-based adsorbent for the extracorporeal removal of β2-microglobulin. Kidney International, vol. 65 (2004), pp. 310-322.
Grupp et al. Chimeric Antigen Receptor-Modified T Cells for Acute Lymphoid Leukemia. N Engl J Med 368; 16, pp. 1509-1508 (Apr. 18, 2013). With correction published N. Engl J. Med (2016) 374(10) 998.
Haegert et al. Co-expression of surface immunoglobulin and T3 on hairy cells. Scand J Haematol 1986;37:196-202.
Haynes et al. Rejection of syngeneic colon carcinoma by CTLs expressing single-chain antibody receptors codelivering CD28 costimulation. J Immunol 2002; 169:5780-5786.
Haynes et al. Single-chain antigen recognition receptors that costimulate potent rejection of established experimental tumors. Blood. Nov. 1, 2002;100(9):3155-63. Published online Jul. 5, 2002.
Hegde, M. et al., Supplementary Material for "Combinational targeting offsets antigen escape and enhances effector functions of adoptively transferred T cells in glioblastoma", Molecular Therapy, 2013, vol. 21, pp. 2087-2101. Retrieved Jan. 6, 2022 from URL: https://ars.els-cdn.com/content/image/1-s2.0-S1525001616309315-mmc1.pdf. 9 pages.
Hexham et al. Influence of relative binding affinity on efficacy in a panel of anti-CD3 scFv immunotoxins. Molecular Immunology 38 (2001) 397-408.
Holliger et al. "Diabodies": small bivalent and bispecific antibody fragments. Proc Natl Acad Sci USA, vol. 90, pp. 6444-6448 (Jul. 1993).
Hombach et al. Tumor-Specific T Cell Activation by Recombinant Immunoreceptors: CD3Z Signaling and CD28 Costimulation Are Simultaneously Required for Efficient IL-2 Secretion and Can Be

(56) References Cited

OTHER PUBLICATIONS

Integrated Into One Combined CD28/CD3ζ Signaling Receptor Molecule. J Immunol 2001; 167:6123-6131.
Imai et al. Chimeric receptors with 4-1BB signaling capacity provoke potent cytotoxicity against acute lymphoblastic leukemia. Leukemia (2004) 18, 676-684.
Imai et al. Genetic modification of primary natural killer cells overcomes inhibitory signals and induces specific killing of leukemic cells. Blood (2005) 106 (1): 376-383.
Imamura. M. et al., Supplementary Material for "Autonomous growth and increased cytotoxicity of natural killer cells expressing membrane-bound interleukin-15", Blood, 2014, vol. 124, pp. 1081-1088. Retrieved Jan. 6, 2021 at URL: https://ash.silverchair-cdn.com/ash/content_public/journal/blood/124/7/10.1182_blood-2014-02-556837/4/blood-2014-02-556837-1.pdf?Expires=1644340511&Signature=uyyKt0KS8WtXpVUILTgok2RyynmzBJgE2vCNIDD4xdwCv13vsg0goCLOpQLU~KVPtITvlHtmCLeX2MhA7mcxzXy~ydDqrj6rHeZEBNohY4NOkmjpH9529c9SCChMFB1n80TH-cM-MgQfrETegs4oK6vjiveJODaZP6TfW1gGK~5JUAn5LesZfPv9W28NmBfMoAOMVeX4Pz54V~9dWaBcCfXCR7vOrx1N8cpbxmlAumSziwKqxNCy79dwOL6ddz3joiyKtMiGNuY1c6l1f6b~MwbLxZ3jKI6EE-giQZhSxfLm2ctwuCbOMj8RIHCM4cO5a2zIKMAM6dut-dafGbQaRQ_&Key-Pair-Id=APKAIE5G5CRDK6RD3PGA. 11 pages.
Jackson et al., Identification of a consensus motif for retention of transmembrane proteins in the endoplasmic reticulum, Embo J. Oct. 1990; 9(10): 3153-3162.
Joshi et al. Fusion to a highly charged proteasomal retargeting sequence increases soluble cytoplasmic expression and efficacy of diverse anti-synuclein intrabodies. mAbs, vol. 4, Issue 6, pp. 686-693 (2012). Published online: Aug. 28, 2012.
Kalos, et al., "T Cells with Chimeric Antigen Receptors Have Potent Antitumor Effects and Can Establish Memory in Patients with Advanced Leukemia", Science Translation Medicine 3.95 (2011):95ra73-95ra73.
Kamiya et al. Blocking expression of inhibitory receptor NKG2A overcomes tumor resistance to NK cells. J Clin Invest. 2019; 129(5):2094-2106.
Kloss, C.C. et al., Supplementary Text and Figures for "Combinatorial antigen recognition with balanced signaling promotes selective tumor eradication by engineered T cells", Nature Biotechnology, 2013, vol. 31, pp. 71-75. Retrieved Jan. 6, 2021 at URL: https://static-content.springer.com/esm/art%3A10.1038%2Fnbt.2459/MediaObjects/41587_2013_BFnbt2459_MOESM2_ESM.pdf. 5 pages.
Kloss. Combinatorial antigen recognition with balanced signaling promotes selective tumor eradication by engineered T cells. Nature Technology, vol. 31, No. 1, pp. 71-75 (Jan. 2013). Published online Dec. 16, 2012.
Kochenderfer et al. B-cell depletion and remissions of malignancy along with cytokine- associated toxicity in a clinical trial of anti-CD19 chimeric-antigen-receptor-transduced T cells. Blood. 2012;119(12):2709-2720. Published online Dec. 8, 2011.
Kochenderfer et al., Chemotherapy-refractory diffuse large B-cell lymphoma and indolent B-cell malignancies can be effectively treated with autologous T cells expressing an anti-CD19 chimeric antigen receptor, Journal of Clinical Oncology, Feb. 20, 2015; 33(6); pp. 540-549. Published online Aug. 25, 2014.
Kochenderfer et al., Donor-derived CD19-targeted T cells cause regression of malignancy persisting after allogeneic hematopoietic stem cell transplantation, Blood. 2013;122(25):4129-4139.
Kolb et al. Graft-versus-leukemia effect of donor lymphocyte transfusions in marrow grafted patients. Blood, vol. 86. No. 5 (Sep. 1), 1995: pp. 2041-2050.
Kotteas et al. Immunotherapy for pancreatic cancer. J Cancer Res Clin Oncol (2016) 142:1795-1805. Published online Feb. 3, 2016.
Lee, et al. Current concepts in the diagnosis and management of cytokine release syndrome. Blood. Jul. 10, 2014;124(2):188-95. doi: 10.1182/blood-2014-05-552729. Epub May 29, 2014.
Lee et al., T cells expressing CD 19 chimeric antigen receptors for acute lymphoblastic leukaemia in children and young adults: a phase 1 dose-escalation trial. Lancet, Feb. 7, 2015; 385 (9967); pp. 517-528. Epub Oct. 13, 2014.
Lo et al. Harnessing the tumour-derived cytokine, CSF-1, to costimulate T-cell growth and activation. Molecular Immunology 45 (2008) 1276-1287. Available online Oct. 24, 2007.
Lorentzen et al. CD19-Chimeric Antigen Receptor T Cells for Treatment of Chronic Lymphocytic Leukaemia and Acute Lymphoblastic Leukaemia. Scandinavian Journal of Immunology, 2015, 82, 307-319.
Maciocia et al. A simple protein-based method for generation of 'off the shelf' allogeneic chimeric antigen receptor T-cells. Database Embase [Online] 1-15, Elsevier Science Publishers, Amsterdam, NL (May 1, 2018). Abstract. XP002784541. Database Accession No. EMB-623339718.
Maciocia et al. A simple protein-based method for generation of 'off the shelf' allogeneic chimeric antigen receptor T-cells. Molecular Therapy, vol. 26, No. 5, Supplement 1, pp. 296-297 (May 2018). Cell Press NLD. May 16, 2018 to May 19, 2018 Chicago, IL-297 Conf. ISSN: 1525-0024.
MacLeod et al., Integration of a CD19 CAR into the TCR Alpha Chain Locus Streamlines Production of Allogeneic Gene-Edited CAR T Cells, Molecular Therapy, vol. 25, No. 4, pp. 949-961, Apr. 2017.
Maher et al. Human T-lymphocyte cytotoxicity and proliferation directed by a single chimeric TCRzeta /CD28 receptor. Nat Biotech 20(1):70-75 (2002).
Marasco et al. Design, intracellular expression, and activity of a human anti-human immunodeficiency virus type 1 gp120 single-chain antibody. PNAS USA 90:7889-7893 (1993).
Maude, et al., Chimeric Antigen Receptor T Cells for Sustained Remissions in Leukemia. N. Engl J. Med (2014) 371(16) 1507-1517. With correction published N. Engl J. Med 374(10):998 (2016).
Miller et al. Successful adoptive transfer and in vivo expansion of human haploidentical NK cells in patients with cancer. Blood 105:3051-3057 (2005).
Miller. Therapeutic applications: natural killer cells in the clinic. Hematology Am Soc Hematol Educ Program (2013) 2013 (1): 247-253.
Munro et al., A C-terminal signal prevents secretion of luminal ER proteins, Cell. Mar. 13, 1987;48:899-907. Retrieved Apr. 7, 2022 at URL: https://bio.davidson.edu/molecular/MunPelham/mufixed.html.
Kochenderfer et al., Eradication of B-lineage cells and regression of lymphoma in a patient treated with autologous T cells genetically engineered to recognize CD19 (Blood, 2010, 116:4099-4102) (Year: 2010).
Needleman et al. A general method applicable to the search for similarities in the amino acid sequence of two proteins. Journal of molecular biology 48(3):443-453 (1970).
Neelapu et al., Axicabtagene Ciloleucel CAR T-Cell Therapy in Refractory Large B-Cell Lymphoma, N Engl J Med 377;26 pp. 2531-2544 (Dec. 28, 2017).
Pardoll. The blockade of immune checkpoints in cancer immunotherapy. Nat Rev Cancer. 12(4):252-264 (2012).
Park et al. Are all chimeric antigen receptors created equal? J Clin Oncol. Feb. 20, 2015;33(6):651-3. Epub Jan. 20, 2015.
Park et al., CD19-targeted CAR T-cell therapeutics for hematologic malignancies: interpreting clinical outcomes to date, Blood. 2016;127(26):3312-3320.
PCT/SG2016/050063 International Search Report and Written Opinion dated May 9, 2016.
PCT/US2018/046137 International Search Report and Written Opinion dated Oct. 29, 2018.
Pearson and Lipman, Improved tools for biological sequence comparison, Proc. Nat. Acad Sci USA., 85:2444-2448, (1988).
Peipp et al. A Recombinant CD7-specific Single-Chain Immunotoxin Is a Potent Inducer of Apoptosis in Acute Leukemic T Cells. Cancer Research 62, pp. 2848-2855 (May 15, 2002).
Poirot et al. Multiplex Genome-Edited T-cell Manufacturing Platform for Off-the-Shelf Adoptive T-cell Immunotherapies. Cancer Research 75(18):3853-3864 (2015).

(56) References Cited

OTHER PUBLICATIONS

Porter et al., Chimeric antigen receptor-modified T cells in chronic lymphoid leukemia. N Engl J Med 365:725-733 (2011). With correction published N. Engl J. Med (2016) 374(10) 998.
Porter et al. Induction of Graft-versus-Host Disease as Immunotherapy for Relapsed Chronic Myeloid Leukemia. N Engl J Med 1994; 330:100-106.
Qasim et al., Molecular remission of infant B-ALL after infusion of universal TALEN gene-edited CART cells. Sci. Transl. Med. 9, eaaj2013 (2017). With Erratum. Erratum retrieved Apr. 7, 2022 at URL: https://www.science.org/doi/10.1126/scitranslmed.aam9292. 3 pages.
Reshef et al. Blockade of lymphocyte chemotaxis in visceral graft-versus-host disease. N Engl J Med 367;3 pp. 135-145 (Jul. 12, 2012).
Rosenberg et al. Adoptive cell transfer as personalized immunotherapy for human cancer. Science 348(6230):62-68 (2015).
Rowley, J. et al., Supplementary Information for "Expression of IL-15RA or an IL-15/IL-15RA fusion on CD8+ T cells modifies adoptively transferred T-cell function in cis", European Journal of Immunology, 2009, vol. 39, pp. 491-506. Retrieved Jan. 6, 2022 at URL: https://onlinelibrary.wiley.com/action/downloadSupplement?doi=10.1002%2Feji.200838594&file=eji_200838594_sm_SupplInfoFig.pdf. 6 pages.
Rubnitz et al. NKAML: A Pilot Study to Determine the Safety and Feasibility of Haploidentical Natural Killer Cell Transplantation in Childhood Acute Myeloid Leukemia. J Clin Oncol. Feb. 20, 2010; 28(6): 955-959.
Rudikoff, et al. Single amino acid substitution altering antigen-binding specificity. Proc Natl Acad Sci U S A. Mar. 1982;79(6):1979-83.
Ruggeri et al. Effectiveness of donor natural killer cell alloreactivity in mismatched hematopoietic transplants. Science 295(5562):2097-2100 (2002).
Sadelain et al. The Basic Principles of Chimeric Antigen Receptor Design. Cancer Discov. Apr. 2013 ; 3(4): 388-398.
Sadelain et al. Therapeutic T cell engineering. Nature 545:423-431 (2017).
Sato et al. Single domain intrabodies against WASP inhibit TCR-induced immune responses in transgenic mice T cells. Sci Rep. Oct. 21, 2013;3:3003. 10 pages.
Schumann, et al. Generation of knock-in primary human T cells using Cas9 ribonucleoproteins. Proc Natl Acad Sci U S A. Aug. 18, 2015;112(33):10437-42. doi: 10.1073/pnas.1512503112. Epub Jul. 27, 2015.
Schuster et al., Chimeric Antigen Receptor T Cells in Refractory B-Cell Lymphomas, Dec. 28, 2017,, the New England Journal of Medicine, 2017; 377; pp. 2545-2554.
Schwartz. T cell anergy. Annu Rev Immunol. 2003;21:305-34. First published online as a Review in Advance on Dec. 5, 2002.
Score Search Results Detail for U.S. Appl. No. 17/862,721 and Search Results Aug. 29, 2022_091720_us-17-862-721-16.rag. Search run on Aug. 29, 2022. Copy retrieved Aug. 30, 2022 at score.uspto.gov/ScoreAccessWeb/getItemDetail?appId=17862721&docId=bc544287-1664-44c7-9aff-7ec7ba8cb7ea&itemName=20220829_091720 . . . 14 pages.
Score Search Results Detail for U.S. Appl. No. 17/862,721 and Search Results Aug. 29, 2022_091720_us-17-862-721-16.rai. Search run on Aug. 29, 2022. Copy retrieved Aug. 30, 2022 at score.uspto.gov/ScoreAccessWeb/getItemDetail?appId=17862721&docId=131a34de-dcc5-448f-b75f-7ea24f699275&itemName=20220829_091720_ . . . 8 pages.
Score Search Results Detail for U.S. Appl. No. 17/862,721 and Search Results Aug. 29, 2022_091720_us-17-862-721-16.rapm. Search run on Aug. 29, 2022. Copy retrieved Aug. 30, 2022 at score.uspto.gov/ScoreAccessWeb/getItemDetail?appId=17862721&docId=e6f49583-c02c-4eee-a87c-e0ece396955c&itemName=20220829_091720 . . . 10 pages.
Score Search Results Detail for U.S. Appl. No. 17/862,721 and Search Results Aug. 29, 2022_091720_us-17-862-721-17.rag. Search run on Aug. 29, 2022. Copy retrieved Aug. 30, 2022 at score.uspto.gov/ScoreAccessWeb/getItemDetail?appId=17862721&docId=cbb41ae5-1511-498f-ac7c-0b33abd2492f&itemName=20220829_091720 . . . 15 pages.
Score Search Results Detail for U.S. Appl. No. 17/862,721 and Search Results Aug. 29, 2022_091720_us-17-862-721-17.rai. Search run on Aug. 29, 2022. Copy retrieved Aug. 31, 2022 at score.uspto.gov/ScoreAccessWeb/getItemDetail?appId=17862721&docId=73e892a9-d59f-4aff-8df1-883c983c2966&itemName=20220829_091720_u . . . 8 pages.
Score Search Results Detail for U.S. Appl. No. 17/862,721 and Search Results Aug. 29, 2022_091720_us-17-862-721-17.rapm. Search run on Aug. 29, 2022. Copy retrieved Aug. 31, 2022 at score.uspto.gov/ScoreAccessWeb/getItemDetail?appId=17862721&docId=9851a8bc-7a77-4e69-985e-903a1f2622ae&itemName=20220829_09172 . . . 10 pages.
Score Search Results Detail for U.S. Appl. No. 17/862,721 and Search Results Aug. 29, 2022_091720_us-17-862-721-17.rpr. Search run on Aug. 29, 2022. Copy retrieved Aug. 31, 2022 at score.uspto.gov/ScoreAccessWeb/getItemDetail?appId=17862721&docId=e04b2be2-c5c8-4cba-b806-cd02a1efe868&itemName=20220829_091720_ . . . 7 pages.
Score Search Results Detail for U.S. Appl. No. 17/862,721 and Search Results Aug. 29, 2022_091720_us-17-862-721-20.rai. Search run on Aug. 29, 2022. Copy retrieved Aug. 31, 2022 at score.uspto.gov/ScoreAccessWeb/getItemDetail?appId=17862721&docId=d17ad86f-3b93-47e9-a94e-a9258afaa3e3&itemName=20220829_091720_ . . . 9 pages.
Score Search Results Detail for U.S. Appl. No. 17/862,721 and Search Results Aug. 29, 2022_091720_us-17-862-721-20.rapm. Search run on Aug. 29, 2022. Copy retrieved Aug. 31, 2022 at score.uspto.gov/ScoreAccessWeb/getItemDetail?appId=17862721&docId=5747899e-d2f6-4407-8197-6ae6e43ac551&itemName=20220829_09172 . . . 11 pages.
Score Search Results Detail for U.S. Appl. No. 17/862,721 and Search Results Aug. 29, 2022_091720_us-17-862-721-20.rpr. Search run on Aug. 29, 2022. Copy retrieved Aug. 31, 2022 at score.uspto.gov/ScoreAccessWeb/getItemDetail?appId=17862721&docId=8db4eb9f-566a-448b-8a1b-9244e2b8f0ee&itemName=20220829_091720_ . . . 7 pages.
Score Search Results Detail for U.S. Appl. No. 17/862,721 and Search Results Aug. 29, 2022_091720_us-17-862-721-21.rag. Search run on Aug. 29, 2022. Copy retrieved Aug. 31, 2022 at score.uspto.gov/ScoreAccessWeb/getItemDetail?appId=17862721&docId=69e4190a-317d-4f26-9846-c30ab0601669&itemName=20220829_09172 . . . 14 pages.
Score Search Results Detail for U.S. Appl. No. 17/862,721 and Search Results Aug. 29, 2022_091720_us-17-862-721-21.rai. Search run on Aug. 29, 2022. Copy retrieved Aug. 31, 2022 at score.uspto.gov/ScoreAccessWeb/getItemDetail?appId=17862721&docId=a9c72e86-3699-4e4c-8110-8367d0fe6cf4&itemName=20220829_091720_ . . . 8 pages.
Sharma et al., "Novel cancer immunotherapy agents with survival benefit: recent successes and next steps," Nat Rev Cancer, 11(11):805-812 (2011).
Shikano et al., Membrane receptor trafficking: Evidence of proximal and distal zones conferred by two independent endoplasmic reticulum localization signals, PNAS May 13, 2003 100 (10) 5783-5788.
Shimasaki et al. A clinically adaptable method to enhance the cytotoxicity of natural killer cells against B-cell malignancies. Cytotherapy, 2012; 14: 830-840.
Shimasaki et al., Natural killer cell reprogramming with chimeric immune receptors, Methods Mol Biol. 2013;969:203-20.
Slavin et al. Allogeneic cell therapy with donor peripheral blood cells and recombinant human interleukin-2 to treat leukemia relapse after allogeneic bone marrow transplantation. Blood (1996) 87 (6): 2195-2204.
Smith et al. Comparison of Biosequences. Advances in Applied Mathematics. 2:482-489 (1981).
Smith et al. T cell activation by anti-T3 antibodies: Comparison of IgG1 and IgG2b switch variants and direct evidence for accessory function of macrophage Fc receptors. Eur J Immunol 16:478-486 (1986).

(56) References Cited

OTHER PUBLICATIONS

Sommermeyer et al., Fully human CD19-specific chimeric antigen receptors for T-cell therapy. Leukemia. Oct. 2017 ; 31(10): 2191-2199.
Strebe et al. Functional knockdown of VCAM-1 at the post-translational level with ER retained antibodies. Journal of Immunological Methods 341 (2009) 30-40. Available online Nov. 25, 2008.
Su et al., CRISPR-Cas9 mediated efficient PD-I disruption on human primary T cells from cancer patients, Sci Rep 6, 20070, Published: Jan. 28, 2016. 14 pages.
Till et al. CD20-specific adoptive immunotherapy for lymphoma using a chimeric antigen receptor with both CD28 and 4-1BB domains: pilot clinical trial results. Blood 119(17):3940-3950 (2012).
Todorovska et al. Design and application of diabodies, triabodies and tetrabodies for cancer targeting. Journal of Immunological Methods 248 (2001) 47-66.
Topp et al. Targeted therapy with the T-cell-engaging antibody blinatumomab of chemotherapy-refractory minimal residual disease in B-lineage acute lymphoblastic leukemia patients results in high response rate and prolonged leukemia-free survival. J Clin Oncol. Jun. 20, 2011;29(18):2493-8.
Torikai et al. A foundation for universal T-cell based immunotherapy: T cells engineered to express a CD19-specific chimeric-antigen-receptor and eliminate expression of endogenous TCR. Blood 119(24):5697-5705 (2012).
Turtle et al. CD19 CAR-T cells of defined CD4+:CD8+ composition in adult B cell All patients. J Clin Invest 126(6):2123-2138 (2016).
U.S. Appl. No. 15/548,577 Notice of Allowance dated May 4, 2020.
U.S. Appl. No. 15/548,577 Office Action dated Jan. 14, 2019.
U.S. Appl. No. 15/548,577 Office Action dated Jul. 20, 2018.
U.S. Appl. No. 15/548,577 Office Action dated Sep. 17, 2019.
U.S. Appl. No. 16/100,117 Office Action dated Aug. 12, 2022.
U.S. Appl. No. 16/100,117 Office Action dated Dec. 9, 2021.
U.S. Appl. No. 16/100,117 Office Action dated May 3, 2021.
U.S. Appl. No. 16/100,120 Office Action dated Aug. 2, 2019.
U.S. Appl. No. 16/100,120 Office Action dated Feb. 24, 2020.
U.S. Appl. No. 16/100,120 Office Action dated Jan. 28, 2019.
U.S. Appl. No. 16/100,120 Office Action dated Oct. 6, 2020.
U.S. Appl. No. 17/862,721 Office Action dated Sep. 7, 2022.
Van Wauwe et al. Human T lymphocyte activation by monoclonal antibodies; OKT3, but not UCHT1, triggers mitogenesis via an interleukin 2-dependent mechanism. J Immunol, vol. 133, No. 1, pp. 129-132 (Jul. 1984).
Verneris et al. Natural Killer Cell Consolidation for Acute Myelogenous Leukemia: A Cell Therapy Ready for Prime Time? J Clin Oncol. Feb. 20, 2010; 28(6): 909-910.
Verwilghen et al. Differences in the stimulating capacity of immobilized anti-CD3 monoclonal antibodies: variable dependence on interleukin-1 as a helper signal for T-cell activation. Immunology 72:269-276 (1991).
Vivier, Eric et al., Innate or adaptive immunity? The example of natural killer cells, Science (New York, N.Y.) vol. 331,6013 (2011): 44-9. doi:10.1126/science.1198687.
Wang et al. Expression and characterization of recombinant soluble monkey CD3 molecules: mapping the FN18 polymorphic epitope. Molecular Immunology 40:1179-1188 (2004).
Weetall et al. T-cell depletion and graft survival induced by anti-human CD3 immunotoxins in human CD3ε transgenic mice. Transplantation, vol. 73, 1658-1666, No. 10 (May 27, 2002).
Wheeler et al. Intrabody and intrakine strategies for molecular therapy. Molecular Therapy, vol. 8, No. 3, pp. 355-366, Sep. 2003.
Wunderlich et al. OKT3 prevents xenogeneic GVHD and allows reliable xenograft initiation from unfractionated human hematopoietic tissues. Blood. 2014; 123(24):e134-e144.
Yang et al., Challenges and opportunities of allogeneic donor-derived CAR T cells, Current Opinion in Hematology, Nov. 2015; 22 (6); pp. 509-515.
Zang et al. The B7 family and cancer therapy: costimulation and coinhibition. Clin Cancer Res 13(18) pp. 5271-5279 (Sep. 15, 2007).
Zhan et al. Modification of ricin A chain, by addition of endoplasmic reticulum (KDEL) or Golgi (YQRL) retention sequences, enhances its cytotoxicity and translocation. Cancer Immunology, Immunotherapy. vol. 46, pp. 55-60 (1998).
Score Search Results Details for U.S. Appl. No. 15/548,577 and Search Result Jan. 7, 2019_143513_us-15-548-577-37.rag. Search run on Jan. 7, 2019. Copy retrieved Sep. 11, 2019 at http://score.uspto.gov/ScoreAccessWeb/getItem.htm?AppId=15548577&seqId=09323b67 . . . 4 pages.
Score Search Results Details for U.S. Appl. No. 15/548,577 and Search Result Jan. 7, 2019_143514_us-15-548-577-36.rapbm. Search run on Jan. 7, 2019. Copy retrieved Sep. 11, 2019 at http://score.uspto.gov/ScoreAccessWeb/getItem.htm?AppId=15548577&seqId=09323b67 . . . 4 pages.
Score Search Results Details for U.S. Appl. No. 15/548,577 and Search Result Jan. 7, 2019_143513_us-15-548-577-37.rag. Search run on Jan. 7, 2019. Copy retrieved Jan. 8, 2019 at http://score.uspto.gov/ScoreAccessWeb/getItem.htm?AppId=15548577&seqId=09323b678 . . . 21 pages.
Score Search Results Details for U.S. Appl. No. 15/548,577 and Search Result Jan. 7, 2019_143514_us-15-548-577-36.rapbm. Search run on Jan. 7, 2019. Copy retrieved Jan. 8, 2019 at http://score.uspto.gov/ScoreAccessWeb/getItem.htm?AppId=15548577&seqId=09323b678 . . . 13 pages.
Score Search Results Details for U.S. Appl. No. 15/548,577 and Search Result Jan. 7, 2019_143514_us-15-548-577-37.rai. Search run on Jan. 7, 2019. Copy retrieved Jan. 8, 2019 at http://score.uspto.gov/ScoreAccessWeb/getItem.htm?AppId=15548577&seqId=09323b678 . . . 11 pages.
Score Search Results Details for U.S. Appl. No. 15/548,577 and Search Result Jan. 7, 2019_145543_us-15-548-577-32.rag. Search run on Jan. 7, 2019. Copy retrieved Jan. 8, 2019 at http://score.uspto.gov/ScoreAccessWeb/getItem.htm?AppId=15548577&seqId=09323b678 . . . 23 pages.
Score Search Results Details for U.S. Appl. No. 15/548,577 and Search Result Jan. 7, 2019_145544_us-15-548-577-32.rai. Search run on Jan. 7, 2019. Copy retrieved Jan. 8, 2019 at http://score.uspto.gov/ScoreAccessWeb/getItem.htm?AppId=15548577&seqId=09323b678 . . . 4 pages.
Score Search Results Details for U.S. Appl. No. 15/548,577 and Search Result Jan. 7, 2019_145544_us-15-548-577-32.rapbm. Search run on Jan. 7, 2019. Copy retrieved Jan. 8, 2019 at http://score.uspto.gov/ScoreAccessWeb/getItem.htm?AppId=15548577&seqId=09323b678 . . . 6 pages.
Score Search Results Details for U.S. Appl. No. 15/548,577 and Search Result Jan. 7, 2019_145544_us-15-548-577-33.rai. Search run on Jan. 7, 2019. Copy retrieved Jan. 8, 2019 at http://score.uspto.gov/ScoreAccessWeb/getItem.htm?AppId=15548577&seqId=09323b678 . . . 4 pages.
Score Search Results Details for U.S. Appl. No. 15/548,577 and Search Result Jan. 7, 2019_145544_us-15-548-577-33.rapbm. Search run on Jan. 7, 2019. Copy retrieved Jan. 8, 2019 at http://score.uspto.gov/ScoreAccessWeb/getItem.htm?AppId=15548577&seqId=09323b678 . . . 12 pages.
XP-002784541 "A simple protein-based method for generation of 'off the shelf' allogeneic chimeric antigen receptor T-cells", Journal Conference Abstract, Molecular Therapy, May 1, 2018, vol. 26, No. 5, pp. 296-297.
Arase, Hisashi, et al. "Recognition of virus infected cells by NK cells", Department of Immunochemistry, Research Institute for Microbial Diseases, Osaka University, vol. 54, No. 2, pp. 153-160.
Böldicke, Thomas, Blocking translocation of cell surface molecules from the ER to the cell surface by intracellular antibodies trageted to the ER, J. Cell. Mol. Med., vol. 11, No. 1, 2007, pp. 54-70.
Clift, Dean, et al "A Method for the Acute and Rapid Degradation of Endogenous Proteins", Elsevier Inc., Cell 172, Dec. 14, 2017, pp. 1692-1706.
Dotti, et al., 2014 Design and development of therapies using chimeric antigen receptor-expressing T cells Immunological Rev, pp. 107-126.

(56) References Cited

OTHER PUBLICATIONS

Grimshaw, B.D. et al., BGST Abstract Mar. 9, 2012, abstract P023, "Creating a 'null' T cell for use in adoptive immunotherapy", British Society for Gene and Cell Therapy 2012, http://www.bsgct.org, Human Gene Therapy, 22 pages.

Hegde, M. et al., "Combinational targeting offsets antigen escape and enhances effector functions of adoptively transferred T cells in glioblastoma", Molecular Therapy, 2013, vol. 21, pp. 2087-2101.

Kamiya, et al., A novel method to generate T-cell receptor-deficient antigen receptor T cells, Blood Advances, vol. 2, No. 5, Mar. 13, 2018, pp. 517-528.

Kloss, C.C. et al., "Combinatorial antigen recognition with balanced signaling promotes selective tumor eradication by engineered T cells", Nature Biotechnology, 2013, vol. 31, pp. 71-75.

Kudo, K. et al., "T lymphocytes expressing a CD16 signaling receptor exert antibody dependent cancer cell killing". Cancer Research, 2014, vol. 74, pp. 93-103.

Lantis, E. et al., "Chimeric antigen receptor T Cells with dissociated signaling domains exhibit focused antitumor activity with reduced potential for toxicity in vivo", Cancer Immunology Research, 2013, vol. 1, pp. 43-53.

Lo, A.S.Y. et al., "Harnessing the tumour-derived cytokine, CSF-1, to co-stimulate Tcell growth and activation", Molecular Immunology, 2008, vol. 45, pp. 1276-1287.

Imamura. M. et al., "Autonomous growth and increased cytotoxicity of natural killer cells expressing membrane-bound interleukin-15", Blood, 2014, vol. 124, pp. 1081-1088.

Marschall, Andrea LJ, et al "Specific in vivo knockdown of protein function by intrabodies", Taylor & Francis Group, LLC, Nov./Dec. 2015, vol. 7, Issue 6, pp. 1010-1035.

Milone, Michael C., et al. "Chimeric Receptors Containing CD137 Signal Transduction Domains Mediate Enhanced Survival of T Cells and Increased Antileukemic Efficacy In Vivo," Mol. Ther., 2009, vol. 17, No. 8, pp. 1453-1464.

Png, et al., "Blockade of CD7 expression in T cells for effective chimeric antigen receptor targeting of T-cell malignancies", Blood Advances, vol. 1, No. 25, Nov. 28, 2017, pp. 2348-2360.

Rossig, C. et al., "Genetic modification of T lymphocytes for adoptive immunotherapy", Molecular Therapy, 2004, vol. 10, pp. 5-18.

Rowley, J. et al., "Expression of IL-15RA or an IL-15/IL-15RA fusion on CD8+ T cells modifies adoptively transferred T-cell function in cis", European Journal of Immunology, 2009, vol. 39, pp. 491-506.

Sanz, L. et al., "Antibodies and gene therapy: teaching old 'magic bullets' new tricks", Trends in Immunology, 2004, vol. 25, pp. 85-91.

Zhou, P. et al., "Cells transfected with a non-neutralizing antibody gene are resistant to HIV infection: targeting the endoplasmic reticulum and *trans-Golgi* network", The Journal of Immunology, 1998, vol. 160, pp. 1489-1496.

Grimshaw, Benjamin David "Developing a universal T cell for use in adoptive immunotherapy", XP055493578, Jan. 1, 2015, pp. 190-197, retrieved from internet: URL:http://discovery.ucl.ac.uk/1470207/1/Grimshaw%20Ben%20Thesis.pdf.

Brown et al. Novel Treatments for Chronic Lymphocytic Leukemia and Moving Forward. American Society of Clinical Oncology Educational Book, pp. e317-e325 (2014). Retrieved at URL: https://ascopubs.org/doi/pdfdirect/10.14694/EdBook_AM.2014.34.e317.

Caruana et al. From Monoclonal Antibodies to Chimeric Antigen Receptors for the Treatment of Human Malignancies. Semin Oncol. Oct. 2014 ; 41(5): 661-666.

Certified PCT/US2016/019953 priority document U.S. Appl. No. 62/121,842, Ma, Yupo et al., inventors, filed Feb. 27, 2015.

Feng et al. Treatment of Aggressive T Cell Lymphoblastic Lymphoma/leukemia Using Anti-CD5 CAR T Cells. Stem Cell Reviews and Reports (2021) 17:652-661. Published online Jan. 6, 2021.

Fujiwara, et al. Adoptive Immunotherapy for Hematological Malignancies Using T Cells Gene-Modified to Express Tumor Antigen-Specific Receptors. Pharmaceuticals (Basel). Dec. 2014; 7(12): 1049-1068.

Glienke et al. Advantages and applications of CAR-expressing natural killer cells. Frontiers in Pharmacology, vol. 6, Article 21 (Feb. 12, 2015). 7 pages.

Guo et al. Efficiency and side effects of anti-CD38 CAR T cells in an adult patient with relapsed B-ALL after failure of bi-specific CD19/CD22 CAR T cell treatment. Cell Mol Immunol 17, 430-432 (2020).

Hishima et al. CD5 Expression in Thymic Carcinoma. American Journal of Pathology, vol. 145, No. 2, pp. 268-275 (Aug. 1994).

Imboden et al. Stimulation of CD5 enhances signal transduction by the T cell antigen receptor. J Clin Invest. 1990. 85:130-134.

Jena et al., Redirecting T-cell specificity by introducing a tumor-specific chimeric antigen receptor. Blood. 116:1035-1044 (2010).

Kapp et al. Chapter 1: Post-Targeting Functions of Signal Peptides. In Protein Transport into the Endoplasmic Reticulum, Zimmerman, ed., 2009, Landes Bioscience. 13 pages. Retrieved at URL: https://www.ncbi.nlm.nih.gov/books/NBK6322/.

Lemaistre et al. Phase I Trial of H65-RTA Immunoconjugate in Patients With Cutaneous T-cell Lymphoma. Blood, vol. 78, No. 5 (Sep. 1), 1991: pp. 1173-1182.

Lewis et al. The immunophenotype of pre-TALL/LBL revisited. Experimental and Molecular Pathology 81 (2006) 162-165. Available online Aug. 14, 2006.

Li et al. Flow Cytometry in the Differential Diagnosis of Lymphocyte-Rich Thymoma From Precursor T-Cell Acute Lymphoblastic Leukemia/Lymphoblastic Lymphoma. Am J Clin Pathol 2004;121:268-274.

Litzow et al. How I treat T-cell acute lymphoblastic leukemia in adults. Blood. 2015; 126(7):833-841. Retrieved at URL: https://www.academia.edu/download/47911039/j.yexmp.2006.06.00620160809-3503-eb5sgz.pdf.

Liu et al. [NK cell surface receptors and their research progress—review]. Zhongguo shi yan xue ye xue za zhi. Aug. 2012;20(4):1034-1038. English abstract only. Retrieved at URL: https://pubmed.ncbi.nlm.nih.gov/22931679/. One page.

Morris et al. Antibody-based therapy of leukaemia. Expert Rev Mol Med. Sep. 30, 2009; 11:e29.

Pinz et al. Preclinical targeting of human T cell malignancies using CD4-specific chimeric antigen receptor (CAR)-engineered T cells. Leukemia, accepted article preview (Nov. 3, 2015). Retrieved at URL: https://www.researchgate.net/profile/Alexander-Jares/publication/283493430_Preclinical_targeting_of_human_T_cell_malignancies_using_CD4-specific_chimeric_antigen_receptor_CAR-engineered_T_cells/links/5643662808aef646e6c6a549/Preclinical-targeting-of-human-T-cell-malignancies-using-CD4-specific-chimeric-antigen-receptor-CAR-engineered-T-cells.pdf. 30 pages.

Rezvani et al. The Application of Natural Killer Cell immunotherapy for the Treatment of Cancer. Frontiers in Immunology, vol. 6, Article 578 (Nov. 17, 2015). 13 pages.

Roitt et al. Roitt's Essential Immunology. 12th Edition, Wiley-Blackwell, Chapter 4 (2012).

Sommermeyer, et al., Chimeric antigen receptor-modified T cells derived from defined CD8+ and CD4+ subsets confer superior antitumor reactivity in vivo. Leukemia 30(2):492-500 (2016).

U.S. Appl. No. 17/862,721 Notice of Allowance dated Jun. 9, 2023.

Zhong-Fu et al. Clinical Applications of NK Cells in Tumor Immunotherapy. Chinese Journal of Biochemistry and Molecular Biology 27(12):1088-1093 (Dec. 2011). With English translation.

Arakawa et al. Cloning and Sequencing of the VH and YK Genes of an Anti-CD3 Monoclonal Antibody, and Construction of a Mouse/Human Chimeric Antibody. J Biochem, vol. 120, No. 3, pp. 657-662 (1996).

Certificate of Disclosure by Benjamin D. Grimshaw signed Dec. 15, 2021 for: Grimshaw et al. Creating a Null T Cell for Adoptive Immunotherapy. Poster. Mar. 9, 2012. One page.

Certificate of Disclosure by David Linch signed Dec. 16, 2021 for: Grimshaw et al. Creating a Null T Cell for Adoptive Immunotherapy. Poster. Mar. 9, 2012. One page.

(56) References Cited

OTHER PUBLICATIONS

Certificate of Disclosure by Martin Pule signed Dec. 15, 2021 for: Grimshaw et al. Creating a Null T Cell for Adoptive Immunotherapy. Poster. Mar. 9, 2012. One page.
Co-pending U.S. Appl. No. 18/295,226, inventors Campana; Dario et al., filed Apr. 3, 2023.
Declaration by Benjamin D. Grimshaw signed Sep. 17, 2022. 2 pages.
Nilsson et al. Retention and retrieval in the endoplasmic reticulum and the Golgi apparatus. Current Opinion in Cell Biology 1994, 6:517-521.
Dong, et al. Modern Hematopoietic Stem Cell Transplant Therapeutics. Military Health Press. 1st Edition (2001):175-176. With English machine translation.
GenBank Accession No. AAA83267. Version No. AAA83267.1. sFv antibody, partial [Mus musculus]. Record created Dec. 14, 1995. Page Range: 1-4. Retrieved May 15, 2024 at URL: https://www.ncbi.nlm.nih.gov/protein/AAA83267.1.
GenBank Accession No. AAM12015. Version No. AAM12015.1. monoclonal anti-alpha-1,3-galactosyltransferase IgM heavy chain, partial [Mus musculus]. Record created Apr. 17, 2002. Page Range: 1-3. Retrieved May 15, 2024 at URL: https://www.ncbi.nlm.nih.gov/protein/AAM12015.1.
GenBank Accession No. ABK63997. Version No. ABK63997.1. Immunoglobulin light chain variable region, partial [Mus musculus]. Record created Nov. 25, 2006. Page Range: 1-3. Retrieved May 15, 2024 at URL: https://www.ncbi.nlm.nih.gov/protein/ABK63997.
Chen, Kevin H., et al. Novel Anti-cd3 Chimeric Antigen Receptor Targeting of Aggressive T Cell Malignancies. Oncotarget, vol. 7, 56219-56232 (2016).
Kipriyanov, Sergey M., et al. Two amino acid mutations in an anti-human CD3 single chain Fv antibody fragment that affect the yield on bacterial secretion but not the affinity. Protein Engineering, vol. 10, 445-453 (1997).
U.S. Appl. No. 18/295,226 Office Action dated Aug. 2, 2024.
Ali Khan, Hyder, and Bulent Mutus. Protein disulfide isomerase a multifunctional protein with multiple physiological roles. Frontiers in Chemistry 2:70, 1-9 (2014).
Janeway Jr, Charles A. et al. T-cell receptor gene rearrangement. Immunobiology: The Immune System in Health and Disease, 5th Edition. Garland Science :1-5 (2001).
Tragoolpua, Khajornsak. et al. Generation of functional scFv intrabody to abate the expression of CD147 surface molecule of 293A cells. BMC biotechnology 8:5, 1-13 (2008).
U.S. Appl. No. 17/862,797 Office Action dated Nov. 27, 2024.
EP22180254.9 Extended European Search Report dated Jan. 16, 2023.
U.S. Appl. No. 16/100,117 Notice of Allowance dated Feb. 17, 2023.
U.S. Appl. No. 16/100,117 Notice of Allowance dated Jan. 5, 2023.
U.S. Appl. No. 17/862,721 Notice of Allowance dated Feb. 15, 2023.
U.S. Appl. No. 17/862,721 Office Action dated Jan. 5, 2023.

* cited by examiner

| Name | Specificity tested | Signal peptide & ScFv | | | | Localization domains | | |
|---|---|---|---|---|---|---|---|---|
| mb | CD3,CD45,β2M,HLA I,KIR2DL1-3,NKG2A | CD8 SP | VL | Linker | VH | CD8 TM | | |
| PEST | CD3 | CD8 SP | VL | Linker | VH | PEST | | |
| mb PEST | CD3,CD45,β2M,KIR2DL1-3,NKG2A | CD8 SP | VL | Linker | VH | CD8 TM | PEST | |
| KDEL | CD3,CD45 | CD8 SP | VL | Linker | VH | KDEL | | |
| SEKDEL | CD3 | CD8 SP | VL | Linker | VH | SEKDEL | | |
| AEKDEL | CD3 | CD8 SP | VL | Linker | VH | AEKDEL | | |
| myc KDEL | CD3,CD7,CD45,β2M | CD8 SP | VL | Linker | VH | myc | KDEL | |
| PEST KDEL | CD3 | CD8 SP | VL | Linker | VH | PEST | KDEL | |
| link.(20) KDEL | CD3 | CD8 SP | VL | Linker | VH | Linker | KDEL | |
| link.(10) KDEL | CD3 | CD8 SP | VL | Linker | VH | Linker | KDEL | |
| link.(20) AEKDEL | CD3,CD7,CD45,β2M,HLA I,KIR2DL1-3,NKG2A | CD8 SP | VL | Linker | VH | Linker | AEKDEL | |
| mb EEKKMP | CD3,CD45,β2M,HLA I,KIR2DL1-3,NKG2A | CD8 SP | VL | Linker | VH | CD8 TM | EEKKMP | |
| mb DEKKMP | CD3,CD7,CD45,β2M,KIR2DL1-3,NKG2A | CD8 SP | VL | Linker | VH | CD8 TM | DEKKMP | EEKKMP |
| mb HA KKMP | CD3 | CD8 SP | VL | Linker | VH | CD8 TM (+Cys) | HA | EEKKMP |
| mb PEST KKMP | CD3 | CD8 SP | VL | Linker | VH | CD8 TM | PEST | |
| mb KKTN | CD3 | CD8 SP | VL | Linker | VH | CD8 TM | KKTN | |
| mb YQRL | CD3,CD45 | CD8 SP | VL | Linker | VH | CD8 TM | YQRL | |
| mb RMKCD | CD3 | CD8 SP | VL | Linker | VH | CD8 TM | RMKCD | |
| link.(20)KDER1 | CD3 | CD8 SP | VL | Linker | VH | Linker | KDEL receptor 1 | |

FIG. 2

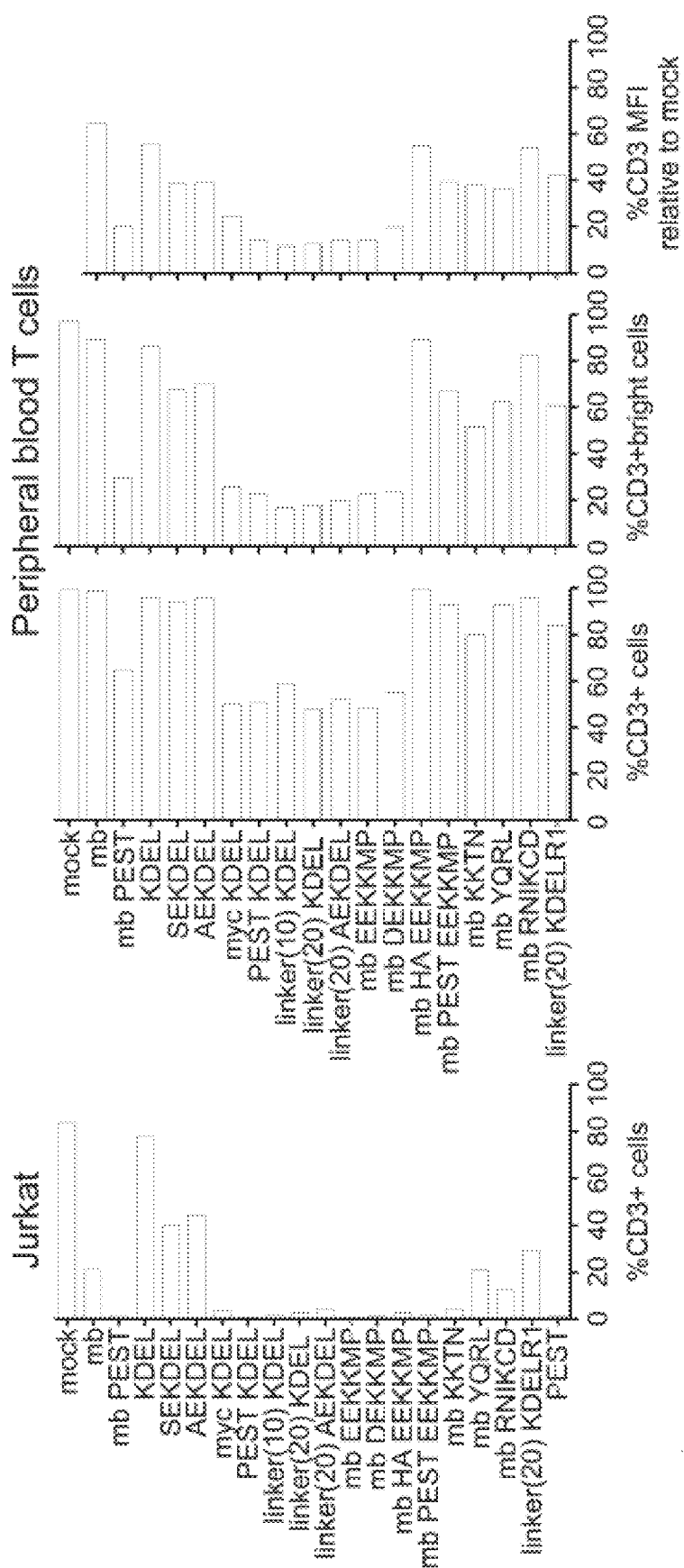

METHODS FOR ENHANCING EFFICACY OF THERAPEUTIC IMMUNE CELLS

CROSS-REFERENCE TO RELATED APPLICATIONS

This application is a continuation of U.S. patent application Ser. No. 15/548,577, filed Aug. 3, 2017, now U.S. Pat. No. 10,765,699, which is a 371 U.S. National Phase Application of International Patent Cooperation Treaty Application PCT/SG2016/050063, filed Feb. 5, 2016, which claims benefit to U.S. Provisional Application No. 62/112,765, filed Feb. 6, 2015, and U.S. Provisional Application No. 62/130,970, filed Mar. 10, 2015, the disclosures of which are incorporated herein by reference in its entirety for all purposes.

REFERENCE TO A SEQUENCE LISTING

The instant application contains a Sequence Listing which has been submitted electronically in ASCII format and is hereby incorporated by reference in its entirety. Said ASCII copy, created on Aug. 2, 2017, is named 14445N SEQUENCE LISTING 8-2-17.TXT and is 32.43 kilobytes in size.

BACKGROUND OF THE INVENTION

Immune cells can be potent and specific "living drugs". Immune cells have the potential to target tumor cells while sparing normal tissues; several clinical observations indicate that they can have major anti-cancer activity. Thus, in patients receiving allogeneic hematopoietic stem cell transplantation (HSCT), T-cell-mediated graft-versus-host disease (GvHD) (Weiden, P L et al., *N. Engl. J. Med.* 1979; 300(19):1068-1073; Appelbaum, FR *Nature,* 2001; 411 (6835):385-389; Porter, D L et al., *N. Engl. J. Med.* 1994; 330(2):100-106; Kolb, H J et al. *Blood.* 1995; 86(5):2041-2050; Slavin, S. et al., *Blood.* 1996; 87(6):2195-2204), and donor natural killer (NK) cell alloreactivity (Ruggeri L, et al. *Science.* 2002; 295(5562):2097-2100; Giebel S, et al. *Blood.* 2003; 102(3):814-819; Cooley S, et al. *Blood.* 2010; 116 (14):2411-2419) are inversely related to leukemia recurrence. Besides the HSCT context, administration of antibodies that release T cells from inhibitory signals (Sharma P, et al., *Nat Rev Cancer.* 2011; 11(11):805-812; Pardoll D M., *Nat Rev Cancer.* 2012; 12(4):252-264), or bridge them to tumor cells (Topp M S, et al. *J. Clin. Oncol.* 2011; 29(18):2493-2498) produced major clinical responses in patients with either solid tumors or leukemia. Finally, infusion of genetically-modified autologous T lymphocytes induced complete and durable remission in patients with refractory leukemia and lymphoma (Maude S L, et al. *N Engl J Med.* 2014; 371(16):1507-1517).

Nevertheless, there is a significant need for improving immune cell therapy by broadening its applicability and enhancing its efficacy.

SUMMARY OF THE INVENTION

The present invention relates to engineered immune cells having enhanced therapeutic efficacy for, e.g., cancer therapy. In certain embodiments, the present invention provides an engineered immune cell that comprises a nucleic acid comprising a nucleotide sequence encoding an immune activating receptor, and a nucleic acid comprising a nucleotide sequence encoding a target-binding molecule linked to a localizing domain.

In other embodiments, the present invention provides the use of an engineered immune cell that comprises a gene encoding an immune activating receptor, and a gene encoding a target-binding molecule linked to a localizing domain for treating cancer, comprising administering a therapeutic amount of the engineered immune cell to a subject in need thereof.

In various embodiments, the present invention also provides a method for producing an engineered immune cell, the method comprising introducing into an immune cell a nucleic acid comprising a nucleotide sequence encoding an immune activating receptor, and a nucleic acid comprising a nucleotide sequence encoding a target-binding molecule linked to a localizing domain, thereby producing an engineered immune cell.

In some embodiments, the engineered immune cells possess enhanced therapeutic efficacy as a result of one or more of reduced graft-versus-host disease (GvHD) in a host, reduced or elimination of rejection by a host, extended survival in a host, reduced inhibition by the tumor in a host, reduced self-killing in a host, reduced inflammatory cascade in a host, or sustained natural/artificial receptor-mediated (e.g., CAR-mediated) signal transduction in a host.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A is an overall mechanism of CAR mediated killing of cancer cells. FIG. 1B shows the combined expression of CAR with different formats of compartment-directed scFv (an example of a target-binding molecule linked to a localizing domain) and examples of possible targets. The CAR can be replaced by other receptors that can enhance immune cell capacity.

FIG. 2 is a schematic diagram of constructs containing scFv together with domains that localize them to specific cellular compartments. Abbreviations: β2M, β-2 microglobulin; SP, signal peptide; VL, variable light chain; VH, variable heavy chain; TM, transmembrane domain; HA, human influenza hemagglutinin. Additional constructs not listed in the figure include membrane-bound (mb) myc EEKKMP, mb myc KKTN, mb myc YQRL, mb TGN38 cytoplasmic domain, mb myc RNIKCD, linker(20-amino acid) mb EEKKMP, as well as variants of constructs without signaling peptide and with a varying number of amino acids in the CD8 transmembrane domain. The nucleotide sequence of the 10-amino acid linker is GGTGGT-GGCGGCAGTGGTGGCGGTGGCTCA (SEQ ID NO: 61); the amino acid sequence is GGGGSGGGGS (SEQ ID NO: 62). The nucleotide sequence of the 20-amino acid linker is GGTGGTGGCGGCAGTGGTGGCGGTGGCTCAGGC-GGTGGTGGCTCCGGTGGCGGT GGCTCT (SEQ ID NO: 63); the amino acid sequence is GGGGSGGGG-SGGGGSGGGGS (SEQ ID NO: 41). Various localization domains are indicated under the heading "Localization domains," and depicts linkers in some examples, as indicated. The constructs "myc KDEL" and "PEST KDEL" show the use of more than one localization domains in a single construct.

FIGS. 3A-3C show downregulation of CD3/TCR in T cells by scFv targeting of CD3ε. FIG. 3A shows expression of surface CD3ε in Jurkat cells, transduced with either a retroviral vector containing green fluorescent protein (GFP) only ("mock") or a vector containing GFP plus different constructs as indicated Expression of CD3ε on the cell membrane was compared to that of mock-transduced cells 1 week after transduction using an anti-CD3 antibody conjugated to allophycocyanin (BD Biosciences). All comparisons were performed after gating on GFP-positive cells. FIG. 3B depicts similar experiments performed with peripheral blood T lymphocytes expanded with anti-CD3/CD28 beads (Lifesciences). Staining was performed 1 week after transduction. FIG. 3C shows flow cytometry plots illustrating downregulation of membrane CD3ε in Jurkat cells after transduction with the constructs indicated. Dashed rectangles on the upper right quadrant of each plot enclose GFP+CD3+ cells.

DETAILED DESCRIPTION OF THE INVENTION

Figure 1A:
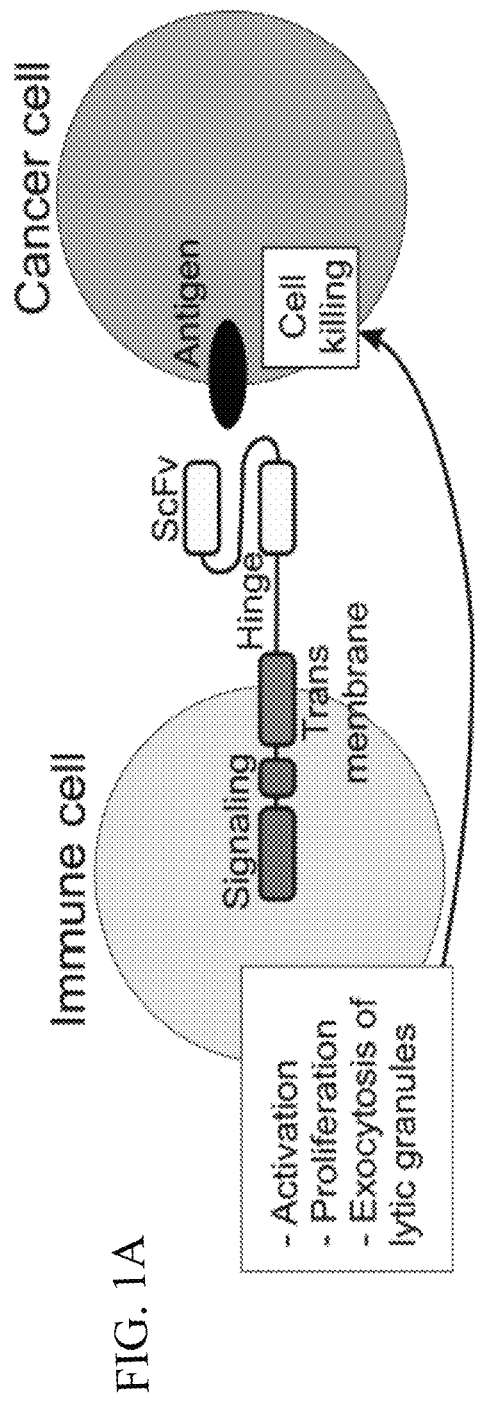
FIGS. 1A-1B is a schematic representation of a strategy employed in the present invention.

A description of example embodiments of the invention follows.

In recent years, gains in knowledge about the molecular pathways that regulate immune cells have been paralleled by a remarkable evolution in the capacity to manipulate them ex vivo, including their expansion and genetic engineering. It is now possible to reliably prepare highly sophisticated clinical-grade immune cell products in a timely fashion. A prime example of how the anti-cancer activity of immune cells can be directed and magnified by ex vivo cell engineering is the development of chimeric antigen receptor (CAR) T cells (Eshhar, Z. et al., *PNAS.* 1993; 90(2):720-724).

CARs are artificial multi-molecular proteins, which have been previously described (Geiger T L, et al., *J Immunol.* 1999; 162(10):5931-5939; Brentjens R J, et al., *Nat Med.* 2003; 9(3):279-286; Cooper L J, et al., *Blood.* 2003; 101 (4):1637-1644). CARs comprise an extracellular domain that binds to a specific target, a transmembrane domain, and a cytoplasmic domain. The extracellular domain and transmembrane domain can be derived from any desired source for such domains, as described in, e.g., U.S. Pat. No. 8,399,645, incorporated by reference herein in its entirety. Briefly, a CAR may be designed to contain a single-chain variable region (scFv) of an antibody that binds specifically to a target. The scFv may be linked to a T-cell receptor (TCR)-associated signaling molecule, such as CD3ζ, via transmembrane and hinge domains. Ligation of scFv to the cognate antigen triggers signal transduction. Thus, CARs can instantaneously redirect cytotoxic T lymphocytes towards cancer cells and provoke tumor cell lysis (Eshhar, Z. et al., *PNAS.* 1993; 90(2):720-724; Geiger T L, et al., *J Immunol.* 1999; 162(10):5931-5939; Brentjens R J, et al., *Nat Med.* 2003; 9(3):279-286; Cooper L J, et al., *Blood.* 2003; 101(4):1637-1644; Imai C, et al., *Leukemia.* 2004; 18:676-684). Because CD3ζ signaling alone is not sufficient to durably activate T cells (Schwartz R H. *Annu Rev Immunol.* 2003; 21:305-334; Zang X and Allison J P. *Clin Cancer Res.* 2007; 13(18 Pt 1):5271-5279), co-stimulatory molecules such as CD28 and 4-1BB (or CD137) have been incorporated into CAR constructs to boost signal transduction. This dual signaling design ("second generation CAR") is useful to elicit effective anti-tumor activity from T cells (Imai C, et al., *Leukemia.* 2004; 18:676-684; Campana D, et al., *Cancer J.* 2014; 20(2):134-140).

A specific CAR, anti-CD19 CAR, containing both 4-1BB and CD3ζ has been described in U.S. Pat. No. 8,399,645. Infusion of autologous T cells expressing an anti-CD19-4-1BB-CD3ζ CAR resulted in dramatic clinical responses in patients with chronic lymphocytic leukemia (CLL) (Porter D L, et al., Chimeric antigen receptor-modified T cells in chronic lymphoid leukemia; 2011: N Engl J Med. 2011; 365(8):725-733; Kalos M, et al., *Sci Transl Med.* 2011; 3(95):95ra73), and acute lymphoblastic leukemia (ALL) (Grupp S A, et al., *N Engl J Med.* 2013; 368(16):1509-1518; Maude S L, et al., *N Engl J Med.* 2014; 371(16):1507-1517). These studies, and studies with CARs bearing different signaling modules (Till B G, et al., *Blood.* 2012; 119(17): 3940-3950; Kochenderfer J N, et al., *Blood.* 2012; 119(12): 2709-2720; Brentjens R J, et al., *Blood.* 2011; 118(18):4817-4828; Brentjens R J, et al., *Sci Transl Med.* 2013; 5(177): 177ra138), provide a convincing demonstration of the clinical potential of this technology, and of immunotherapy in general.

The methods described herein enable rapid removal or inactivation of specific proteins in immune cells redirected by a natural or artificial receptor, e.g., CARs, thus broadening the application potential and significantly improving the function of the engineered cells. The method relies, in part, on a single construct or multiple constructs containing an immune activating receptor, e.g., a CAR (which comprises an extracellular domain (e.g., an scFv) that binds to a specific target, a transmembrane domain, and a cytoplasmic domain) together with a target-binding molecule that binds a target (e.g., protein) to be removed or neutralized; the target-binding molecule is linked to a domain (i.e., localizing domain) that directs it to specific cellular compartments, such as the Golgi or endoplasmic reticulum, the proteasome, or the cell membrane, depending on the application. For simplicity, a target-binding molecule linked to a localizing domain (LD) is sometimes referred to herein as "LD-linked target-binding molecule."

As will be apparent from the teachings herein, a variety of immune activating receptors may be suitable for the methods of the present invention. That is, any receptor that comprises a molecule that, upon binding (ligation) to a ligand (e.g., peptide or antigen) expressed on a cancer cell, is capable of activating an immune response may be used according to the present methods. For example, as described above, the immune activating receptor can be a chimeric antigen receptor (CAR); methods for designing and manipulating a CAR is known in the art (see, Geiger T L, et al., *J Immunol.* 1999; 162(10):5931-5939; Brentjens R J, et al., *Nat Med.* 2003; 9(3):279-286; Cooper L J, et al., *Blood.* 2003; 101(4):1637-1644). Additionally, receptors with antibody-binding capacity can be used (e.g., CD16-4-1BB-CD3zeta receptor—Kudo K, et al. *Cancer Res.* 2014; 74(1): 93-103), which are similar to CARs, but with the scFv replaced with an antibody-binding molecule (e.g., CD16, CD64, CD32). Further, T-cell receptors comprising T-cell receptor alpha and beta chains that bind to a peptide expressed on a tumor cell in the context of the tumor cell HLA can also be used according to the present methods. In addition, other receptors bearing molecules that activate an immune response by binding a ligand expressed on a cancer cell can also be used—e.g. NKG2D-DAP10-CD3zeta receptor, which binds to NKG2D ligand expressed on tumor cells (see, e.g., Chang Y H, et al., *Cancer Res.* 2013; 73(6):1777-1786). All such suitable receptors collectively, as used herein, are referred to as an "immune activating receptor" or a "receptor that activates an immune response upon binding a cancer cell ligand." Therefore, an immune activating receptor having a molecule activated by a cancer cell ligand can be expressed together with a LD-linked target-binding molecule according to the present methods.

The present methods significantly expand the potential applications of immunotherapies based on the infusion of immune cells redirected by artificial receptors. The method described is practical and can be easily incorporated in a clinical-grade cell processing. For example, a single bicistronic construct containing, e.g., a CAR and a LD-linked target-binding molecule, e.g., scFv-myc KDEL (or PEST or transmembrane) can be prepared by inserting an internal ribosomal entry site (IRES) or a 2A peptide-coding region site between the 2 cDNAs encoding the CAR and the LD-linked target-binding molecule. The design of tricistronic delivery systems to delete more than one target should also be feasible. Alternatively, separate transductions of the 2 genes (simultaneously or sequentially) could be performed. In the context of cancer cell therapy, the CAR could be replaced by an antibody-binding signaling receptor (Kudo K, et al., *Cancer Res.* 2014; 74(1):93-103), a T-cell receptor directed against a specific HLA-peptide combination, or any receptor activated by contact with cancer cells (Chang Y H, et al., *Cancer Res.* 2013; 73(6):1777-1786). The results of the studies described herein with simultaneous anti-CD19-4-1BB-CD3ζ CAR and anti-CD3ε scFv-KDEL demonstrate that the signaling capacity of the CAR was not impaired.

Both the anti-CD3ε scFv-KDEL (and -PEST) tested herein stably downregulate CD3 as well as TCR expression. Residual CD3+ T cells could be removed using CD3 beads, an approach that is also available in a clinical-grade format. The capacity to generate CD3/TCR-negative cells that respond to CAR signaling represents an important advance. Clinical studies with CAR T cells have generally been performed using autologous T cells. Thus, the quality of the cell product varies from patient to patient and responses are heterogeneous. Infusion of allogeneic T cells is currently impossible as it has an unacceptably high risk of potentially fatal GvHD, due to the stimulation of the endogenous TCR by the recipient's tissue antigens. Downregulation of CD3/TCR opens the possibility of infusing allogeneic T cells because lack of endogenous TCR eliminates GvHD capacity. Allogeneic products could be prepared with the optimal cellular composition (e.g., enriched in highly cytotoxic T cells, depleted of regulatory T cells, etc.) and selected so that the cells infused have high CAR expression and functional potency. Moreover, fully standardized products could be cryopreserved and be available for use regardless of the patient immune cell status and his/her fitness to undergo apheresis or extensive blood draws. Removal of TCR expression has been addressed using gene editing tools, such as nucleases (Torikai H, et al. *Blood,* 2012; 119(24):5697-5705). Although this is an effective approach, it is difficult to implement in a clinical setting as it requires several rounds of cell selection and expansion, with prolonged culture. The methods described herein have considerable practical advantages.

Additionally, a LD-linked target-binding molecule (e.g., scFv-myc KDEL, scFv-EEKKMP or scFv-PEST, wherein scFv targets a specific protein/molecule) can be used according to the present invention to delete HLA Class I molecules, reducing the possibility of rejection of allogeneic cells. While infusion of allogeneic T cells is a future goal of CAR T cell therapy, infusion of allogeneic natural killer (NK) cells is already in use to treat patients with cancer. A key factor that determines the success of NK cell-based therapy is that NK cells must persist in sufficient numbers to achieve an effector:target ratio likely to produce tumor cytoreduction (Miller J S. Hematology *Am Soc Hematol Educ Program.* 2013; 2013:247-253). However, when allogeneic cells are infused, their persistence is limited. Immunosuppressive chemotherapy given to the patient allows transient engraftment of the infused NK cells but these are rejected within 2-4 weeks of infusion (Miller J S, et al. *Blood.* 2005; 105:3051-3057; Rubnitz J E, et al., *J Clin Oncol.* 2010; 28(6):955-959). Contrary to organ transplantation, continuing immunosuppression is not an option because immunosuppressive drugs also suppress NK cell function. Because rejection is primarily mediated by recognition of HLA Class I molecules by the recipient's CD8+T lymphocytes, removing HLA Class I molecules from the infused NK cells (or T cells) will diminish or abrogate the rejection rate, extend the survival of allogeneic cells, and hence their anti-tumor capacity.

Furthermore, a LD-linked target-binding molecule can be used according to the present invention to target inhibitory receptors. Specifically, administration of antibodies that release T cells from inhibitory signals such as anti-PD1 or anti-CTLA-4 have produced dramatic clinical responses (Sharma P, et al., *Nat Rev Cancer.* 2011; 11(11):805-812; Pardoll D M. *Nat Rev Cancer.* 2012; 12(4):252-264). CAR-T cells, particularly those directed against solid tumors, might be inhibited by similar mechanisms. Thus, expression of a target-binding molecule (e.g., scFv or ligands) against PD1, CTLA-4, Tim3 or other inhibitory receptors would prevent the expression of these molecules (if linked to, e.g., KDEL (SEQ ID NO: 4), EEKKMP (SEQ ID NO: 64) or PEST motif SHGFPPEVEEQDDGTLPMS-CAQESGMDRHPAACASARINV (SEQ ID NO: 7)) or prevent binding of the receptors to their ligands (if linked to a transmembrane domain) and sustain CAR-mediated signal transduction. In NK cells, examples of inhibitory receptors include killer immunoglobulin-like receptors (KIRs) and NKG2A (Vivier E, et al., *Science,* 2011; 331(6013):44-49).

The methods of the present invention also enable targeting of a greater number of targets amenable for CAR-directed T cell therapy. One of the main limitations of CAR-directed therapy is the paucity of specific antigens expressed by tumor cells. In the case of hematologic malignancies, such as leukemias and lymphomas, molecules which are not expressed in non-hematopoietic cells could be potential targets but cannot be used as CAR targets because they are also expressed on T cells and/or NK cells. Expressing such CARs on immune cells would likely lead to the demise of the immune cells themselves by a "fratricidal" mechanism, nullifying their anti-cancer capacity. If the target molecule can be removed from immune cells without adverse functional effects, then the CAR with the corresponding specificity can be expressed. This opens many new opportunities to target hematologic malignancies. Examples of the possible targets include CD38 expressed in multiple myeloma, CD7 expressed in T cell leukemia and lymphoma, Tim-3 expressed in acute leukemia, CD30 expressed in Hodgkin disease, CD45 and CD52 expressed in all hematologic malignancies. These molecules are also expressed in a substantial proportion of T cells and NK cells.

Moreover, it has been shown that secretion of cytokines by activated immune cells triggers cytokine release syndrome and macrophage activation syndrome, presenting serious adverse effects of immune cell therapy (Lee D W, et al., *Blood.* 2014; 124(2):188-195). Thus, the LD-linked target-binding molecule can be used according to the present invention to block cytokines such as IL-6, IL-2, IL-4, IL-7, IL-10, IL-12, IL-15, IL-18, IL-21, IL-27, IL-35, interferon (IFN)-γ, IFN-β, IFN-α, tumor necrosis factor (TNF)-α, and transforming growth factor (TGF)-β, which may contribute to such inflammatory cascade.

Accordingly, in one embodiment, the present invention relates to an engineered immune cell that comprises a nucleic acid comprising a nucleotide sequence encoding an immune activating receptor, and a nucleic acid comprising a nucleotide sequence encoding a target-binding molecule linked to a localizing domain.

As used herein, an "engineered" immune cell includes an immune cell that has been genetically modified as compared to a naturally-occurring immune cell. For example, an engineered T cell produced according to the present methods carries a nucleic acid comprising a nucleotide sequence that does not naturally occur in a T cell from which it was derived. In some embodiments, the engineered immune cell of the present invention includes a chimeric antigen receptor (CAR) and a target-binding molecule linked to a localizing domain (LD-linked target-binding molecule). In a particular embodiment, the engineered immune cell of the present invention includes an anti-CD19-4-1BB-CD3ζ CAR and an anti-CD3 scFv linked to a localizing domain.

In certain embodiments, the engineered immune cell is an engineered T cell, an engineered natural killer (NK) cell, an engineered NK/T cell, an engineered monocyte, an engineered macrophage, or an engineered dendritic cell.

In certain embodiments, an "immune activating receptor" as used herein refers to a receptor that activates an immune response upon binding a cancer cell ligand. In some embodiments, the immune activating receptor comprises a molecule that, upon binding (ligation) to a ligand (e.g., peptide or antigen) expressed on a cancer cell, is capable of activating an immune response. In one embodiment, the immune activating receptor is a chimeric antigen receptor (CAR);

methods for designing and manipulating a CAR are known in the art. In other embodiments, the immune activating receptor is an antibody-binding receptor, which is similar to a CAR, but with the scFv replaced with an antibody-binding molecule (e.g., CD16, CD64, CD32) (see e.g., CD16-4-1BB-CD3zeta receptor—Kudo K, et al. *Cancer Res.* 2014; 74(1):93-103). In various embodiments, T-cell receptors comprising T-cell receptor alpha and beta chains that bind to a peptide expressed on a tumor cell in the context of the tumor cell HLA can also be used according to the present methods. In certain embodiments, other receptors bearing molecules that activate an immune response by binding a ligand expressed on a cancer cell can also be used—e.g., NKG2D-DAP10-CD3zeta receptor, which binds to NKG2D ligand expressed on tumor cells (see, e.g., Chang Y H, et al., *Cancer Res.* 2013; 73(6):1777-1786). All such suitable receptors capable of activating an immune response upon binding (ligation) to a ligand (e.g., peptide or antigen) expressed on a cancer cell are collectively referred to as an "immune activating receptor." As would be appreciated by those of skill in the art, an immune activating receptor need not contain an antibody or antigen-binding fragment (e.g., scFv); rather the portion of the immune activating receptor that binds to a target molecule can be derived from, e.g., a receptor in a receptor-ligand pair, or a ligand in a receptor-ligand pair.

In certain aspects, the immune activating receptor binds to molecules expressed on the surface of tumor cells, including but not limited to, CD20, CD22, CD33, CD2, CD3, CD4, CD5, CD7, CD8, CD45, CD52, CD38, CS-1, TIM3, CD123, mesothelin, folate receptor, HER2-neu, epidermal-growth factor receptor, and epidermal growth factor receptor. In some embodiments, the immune activating receptor is a CAR (e.g., anti-CD19-4-1BB-CD3ζ CAR). In certain embodiments, the immune activating receptor comprises an antibody or antigen-binding fragment thereof (e.g., scFv) that binds to molecules expressed on the surface of tumor cells, including but not limited to, CD20, CD22, CD33, CD2, CD3, CD4, CD5, CD7, CD8, CD45, CD52, CD38, CS-1, TIM3, CD123, mesothelin, folate receptor, HER2-neu, epidermal-growth factor receptor, and epidermal growth factor receptor. Antibodies to such molecules expressed on the surface of tumor cells are known and available in the art. By way of example, antibodies to CD3 and CD7 are commercially available and known in the art. Such antibodies, as well as fragments of antibodies (e.g., scFv) derived therefrom, can be used in the present invention, as exemplified herein. Further, methods of producing antibodies and antibody fragments against a target protein are well-known and routine in the art.

The transmembrane domain of an immune activating receptor according to the present invention (e.g., CAR) can be derived from a single-pass membrane protein, including, but not limited to, CD8α, CD8β, 4-1BB, CD28, CD34, CD4, FcεRIγ, CD16 (e.g., CD16A or CD16B), OX40, CD3ζ, CD38, CD3γ, CD3δ, TCRα, CD32 (e.g., CD32A or CD32B), CD64 (e.g., CD64A, CD64B, or CD64C), VEGFR2, FAS, and FGFR2B. In some examples, the membrane protein is not CD8α. The transmembrane domain may also be a non-naturally occurring hydrophobic protein segment.

The hinge domain of the immune activating receptor (e.g., CAR) can be derived from a protein such as CD8α, or IgG. The hinge domain can be a fragment of the transmembrane or hinge domain of CD8α, or a non-naturally occurring peptide, such as a polypeptide consisting of hydrophilic residues of varying length, or a (GGGGS)$_n$ (SEQ ID NO: 8) polypeptide, in which n is an integer of, e.g., 3-12, inclusive.

The signaling domain of the immune activating receptor (e.g., CAR) can be derived from CD3ζ, FcεRIγ, DAP10, DAP12 or other molecules known to deliver activating signals in immune cells. At least one co-stimulatory signaling domain of the receptor can be a co-stimulatory molecule such as 4-1BB (also known as CD137), CD28, CD28$_{LL \to GG}$ variant, OX40, ICOS, CD27, GITR, HVEM, TIM1, LFA1, or CD2. Such molecules are readily available and known in the art.

As would be appreciated by those of skill in the art, the components of an immune activating receptor can be engineered to comprise a number of functional combinations, as described herein, to produce a desired result. Using the particular CAR anti-CD19-4-1BB-CD3ζ as an example, the antibody (e.g., or antigen-binding fragment thereof such as an scFv) that binds a molecule can be substituted for an antibody that binds different molecule, as described herein (e.g., anti-CD20, anti-CD33, anti-CD123, etc., instead of anti-CD19). In other embodiments, the co-stimulatory molecule (4-1BB in this specific example) can also be varied with a different co-stimulatory molecule, e.g., CD28. In some embodiments, the stimulatory molecule (CD3ζ in this specific example), can be substituted with another known stimulatory molecule. In various embodiments, the transmembrane domain of the receptor can also be varied as desired. The design, production, and testing for functionality of such immune activating receptors can be readily determined by those of skill in the art. Similarly, the design, delivery into cells and expression of nucleic acids encoding such immune activating receptors are readily known and available in the art.

As used herein, the term "nucleic acid" refers to a polymer comprising multiple nucleotide monomers (e.g., ribonucleotide monomers or deoxyribonucleotide monomers). "Nucleic acid" includes, for example, genomic DNA, cDNA, RNA, and DNA-RNA hybrid molecules. Nucleic acid molecules can be naturally occurring, recombinant, or synthetic. In addition, nucleic acid molecules can be single-stranded, double-stranded or triple-stranded. In some embodiments, nucleic acid molecules can be modified. In the case of a double-stranded polymer, "nucleic acid" can refer to either or both strands of the molecule.

The term "nucleotide sequence," in reference to a nucleic acid, refers to a contiguous series of nucleotides that are joined by covalent linkages, such as phosphorus linkages (e.g., phosphodiester, alkyl and aryl-phosphonate, phosphorothioate, phosphotriester bonds), and/or non-phosphorus linkages (e.g., peptide and/or sulfamate bonds). In certain embodiments, the nucleotide sequence encoding, e.g., a target-binding molecule linked to a localizing domain is a heterologous sequence (e.g., a gene that is of a different species or cell type origin).

The terms "nucleotide" and "nucleotide monomer" refer to naturally occurring ribonucleotide or deoxyribonucleotide monomers, as well as non-naturally occurring derivatives and analogs thereof. Accordingly, nucleotides can include, for example, nucleotides comprising naturally occurring bases (e.g., adenosine, thymidine, guanosine, cytidine, uridine, inosine, deoxyadenosine, deoxythymidine, deoxyguanosine, or deoxycytidine) and nucleotides comprising modified bases known in the art.

As will be appreciated by those of skill in the art, in some aspects, the nucleic acid further comprises a plasmid sequence. The plasmid sequence can include, for example, one or more sequences selected from the group consisting of a promoter sequence, a selection marker sequence, and a locus-targeting sequence.

As used herein, the gene encoding a target-binding molecule linked to a localizing domain is sometimes referred to as "LD-linked target-binding molecule."

In certain embodiments, the target-binding molecule is an antibody or antigen-binding fragment thereof. As used herein, "antibody" means an intact antibody or antigen-binding fragment of an antibody, including an intact antibody or antigen-binding fragment that has been modified or engineered, or that is a human antibody. Examples of antibodies that have been modified or engineered are chimeric antibodies, humanized antibodies, multiparatopic antibodies (e.g., biparatopic antibodies), and multispecific antibodies (e.g., bispecific antibodies). Examples of antigen-binding fragments include Fab, Fab', F(ab')$_2$, Fv, single chain antibodies (e.g., scFv), minibodies and diabodies.

A "Fab fragment" comprises one light chain and the C$_H$1 and variable regions of one heavy chain. The heavy chain of a Fab molecule cannot form a disulfide bond with another heavy chain molecule.

An "Fc" region contains two heavy chain fragments comprising the CH2 and CH3 domains of an antibody. The two heavy chain fragments are held together by two or more disulfide bonds and by hydrophobic interactions of the CH3 domains.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the C$_H$1 and C$_{H^2}$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

In a particular embodiment, the target-binding molecule is single-chain Fv antibody ("scFv antibody"). scFv refers to antibody fragments comprising the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun (1994) *The Pharmacology Of Monoclonal Antibodies*, vol. 113, Rosenburg and Moore eds. Springer-Verlag, New York, pp. 269-315. See also, PCT Publication No. WO 88/01649 and U.S. Pat. Nos. 4,946,778 and 5,260,203. By way of example, the linker between the VH and VL domains of the scFvs disclosed herein comprise, e.g., GGGGSGGGG-SGGGGSGGGGS (SEQ ID NO: 41) or GGGGSGGGG-SGGGGS (SEQ ID NO: 43). As would be appreciated by those of skill in the art, various suitable linkers can be designed and tested for optimal function, as provided in the art, and as disclosed herein.

The scFv that is part of the LD-linked target-binding molecule is not necessarily the same as the scFv that occurs in the context of, e.g., a chimeric antigen receptor (CAR) or a similar antibody-binding signaling receptor. In some embodiments, the scFv that is part of the LD-linked target-binding molecule is the same as the scFv that occurs in the context of, e.g., a chimeric antigen receptor (CAR) or a similar antibody-binding signaling receptor.

In some embodiments, the nucleic acid comprising a nucleotide sequence encoding a target-binding molecule (e.g., an scFv in the context of a LD-linked target-binding molecule) comprises one or more sequences that have at least 80%, at least 85%, at least 88%, at least 90%, at least 92%, at least 94%, at least 95%, at least 96%, at least 97%, at least 98%, at least 99%, or 100% sequence identity to any one or more of SEQ ID NOs: 14, 15, 18, 19, 22, 23, 26, 27, 30, 31, 34, 35, 38, or 39.

The term "sequence identity" means that two nucleotide or amino acid sequences, when optimally aligned, such as by the programs GAP or BESTFIT using default gap weights, share at least, e.g., 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In certain embodiments, the antibody (e.g., scFv) comprises VH and VL having amino acid sequences set forth in SEQ ID NO: 12 and 13, respectively; SEQ ID NO: 16 and 17, respectively; SEQ ID NO: 20 and 21, respectively; SEQ ID NO: 24 and 25, respectively; SEQ ID NO: 28 and 29, respectively; SEQ ID NO: 32 and 33, respectively; or SEQ ID NO: 36 and 37, respectively. In some embodiments, the antibody (e.g., scFv) comprises VH and VL having sequence that each have at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, or 100% sequence identity to the VH and VL sequences set forth in SEQ ID NO: 12 and 13, respectively; SEQ ID NO: 16 and 17, respectively; SEQ ID NO: 20 and 21, respectively; SEQ ID NO: 24 and 25, respectively; SEQ ID NO: 28 and 29, respectively; SEQ ID NO: 32 and 33, respectively; or SEQ ID NO: 36 and 37, respectively.

A "diabody" is a small antibody fragment with two antigen-binding sites. The fragments comprise a heavy chain variable region (VH) connected to a light chain variable region (VL) in the same polypeptide chain (VH-VL or VL-VH). By using a linker that is too short to allow pairing between the two domains on the same chain, the domains are forced to pair with the complementary domains of another chain and create two antigen-binding sites. Diabodies are described in, e.g., patent documents EP 404,097; WO 93/11161; and Holliger et al., (1993) *Proc. Nat. Acad. Sci. USA* 90: 6444-6448.

In certain embodiments, the antibody is a triabody or a tetrabody. Methods of designing and producing triabodies and tetrabodies are known in the art. See, e.g. Todorovska et al., J. Immunol. Methods 248(1-2):47-66, 2001.

A "domain antibody fragment" is an immunologically functional immunoglobulin fragment containing only the variable region of a heavy chain or the variable region of a light chain. In some instances, two or more VH regions are covalently joined with a peptide linker to create a bivalent domain antibody fragment. The two VH regions of a bivalent domain antibody fragment may target the same or different antigens.

In some embodiments, the antibody is modified or engineered. Examples of modified or engineered antibodies include chimeric antibodies, multiparatopic antibodies (e.g., biparatopic antibodies), and multispecific antibodies (e.g., bispecific antibodies).

As used herein, "multiparatopic antibody" means an antibody that comprises at least two single domain antibodies, in which at least one single domain antibody is directed against a first antigenic determinant on an antigen and at least one other single domain antibody is directed against a second antigenic determinant on the same antigen. Thus, for example, a "biparatopic" antibody comprises at least one single domain antibody directed against a first antigenic determinant on an antigen and at least one further single domain antibody directed against a second antigenic determinant on the same antigen.

As used herein, "multispecific antibody" means an antibody that comprises at least two single domain antibodies, in which at least one single domain antibody is directed against a first antigen and at least one other single domain antibody is directed against a second antigen (different from the first antigen). Thus, for example, a "bispecific" antibody is one that comprises at least one single domain antibody directed against a first antigen and at least one further single domain antibody directed against a second antigen, e.g., different from the first antigen.

In some embodiments, the antibodies disclosed herein are monoclonal antibodies, e.g., murine monoclonal antibodies. Methods of producing monoclonal antibodies are known in the art. See, for example, Pluckthun (1994) *The Pharmacology of Monoclonal Antibodies*, Vol. 113, Rosenburg and Moore eds. Springer-Verlag, New York, pp. 269-315.

In various embodiments, the target-binding molecule in the context of a LD-linked target-binding molecule is a receptor or a ligand that binds to a target molecule. For example, that target-binding molecule can be a ligand that binds PD-1 (e.g., PD-L1 or PD-L2). Thus, as would be appreciated by those of skill in the art, the target-binding molecule can be an antibody, or a ligand/receptor that binds a target molecule.

As used herein, "linked" in the context of a LD-linked target-binding molecule refers to a gene encoding a target-binding molecule directly in frame (e.g., without a linker) adjacent to one or more genes encoding one or more localizing domains. Alternatively, the gene encoding a target-binding molecule may be connected to one or more gene encoding one or more localizing domains through a linker sequence, as described herein. Various suitable linkers known in the art can be used to tether the target-binding molecule to a localizing domain. For example, non-naturally occurring peptides, such as a polypeptide consisting of hydrophilic residues of varying length, or a (GGGGS)~ (SEQ ID NO: 8) polypeptide, in which n is an integer of, e.g., 3-12, inclusive, can be used according to the present invention. In particular embodiments, the linker comprises, e.g., GGGGSGGGGS (SEQ ID NO: 62). In some embodiments, the linker comprises, e.g., GGGGSGGGGS-GGGGSGGGGS (SEQ ID NO: 41). In various embodiments, peptide linkers having lengths of about 5 to about 100 amino acids, inclusive, can be used in the present invention. In certain embodiments, peptide linkers having lengths of about 20 to about 40 amino acids, inclusive, can be used in the present invention. In some embodiments, peptide linkers having lengths of at least 5 amino acids, at least 10 amino acids, at least 15 amino acids, at least 20 amino acids, at least 25 amino acids, at least 30 amino acids, at least 35 amino acids, or at least 40 amino acids can be used in the present invention. As would be appreciated by those of skill in the art, such linker sequences as well as variants of such linker sequences are known in the art. Methods of designing constructs that incorporate linker sequences as well as methods of assessing functionality are readily available to those of skill in the art.

In certain embodiments, the LD-linked target-binding molecule binds to a target expressed on the surface of an immune cell. In some embodiments, the LD-linked target-binding molecule inhibits the activity or function of the target molecule. By way of example, as disclosed herein, the LD-linked target-binding molecule can be designed to bind to, e.g. CD3, CD7, CD45, hB2MG, KIR2DL1, KIR2DL2/DL3, or NKG2A, thereby downregulating the cell surface expression of such molecules. Downregulation of such molecules can be achieved through, for example, localizing/targeting the molecules for degradation and/or internalization. In other embodiments, the LD-linked target-binding molecule renders the target inactive (e.g., the target can no longer interact and/or bind to its cognate ligand or receptor).

In some embodiments, the engineered immune cells of the present invention have enhanced therapeutic efficacy. As used herein, "enhanced therapeutic efficacy" refers to one or more of reduced graft-versus-host disease (GvHD) in a host, reduced or elimination of rejection by a host, extended survival in a host, reduced inhibition by the tumor in a host, reduced self-killing in a host, reduced inflammatory cascade in a host, or sustained CAR-mediated signal transduction in a host.

In certain embodiments of the present invention, the target-binding molecule in the context of a LD-linked target-binding molecule binds to a molecule in a CD3/T-cell receptor (TCR) complex, a cytokine, a human leukocyte antigen (HLA) Class I molecule, or a receptor that downregulates immune response.

In certain embodiments, a molecule in a CD3/TCR complex can be CD3ε, TCRα, TCRβ, TCRγ, TCRδ, CD3δ, CD3γ, or CD3ζ. In a particular embodiment, the molecule is CD3ε.

In another embodiment, the HLA Class I molecule is beta-2 microglobulin, α1-microglobulin, α2-microglobulin, or α3-microglobulin.

In other embodiments, a receptor that downregulates immune response is selected from, e.g., PD-1, CTLA-4, Tim3, killer immunoglobulin-like receptors (KIRs—e.g. KIR2DL1 (also known as CD158a), KIR2DL2/DL3 (also known as CD158b)), CD94 or NKG2A (also known as CD159a), protein tyrosine phosphatases such as Src homology region 2 domain-containing phosphatase (SHP)-1 and SHP-2. Thus, such receptors can be targeted by moiety LD-linked target-binding molecule, as described herein.

In various embodiments, examples of cytokines that can be targeted with moiety LD-linked target-binding molecule include, e.g., interleukin (IL)-6, IL-2, IL-4, IL-7, IL-10, IL-12, IL-15, IL-18, IL-21, IL-27, IL-35, interferon (IFN)-γ, IFN-β, IFN-α, tumor necrosis factor (TNF)-α, or transforming growth factor (TGF)-β.

In a further aspect, the LD-linked target-binding molecule binds to a molecule selected from, e.g., CD2, CD4, CD5, CD7, CD8, CD30, CD38, CD45, CD52, or CD127.

Methods of producing antibodies and antibody fragments thereof against any target protein are well-known and routine in the art. Moreover, as exemplified herein, commercially available antibodies to various targets, e.g., CD3 and CD7 can be used to generate a LD-linked target-binding molecule, as exemplified herein. Antibodies known in the art, as well as fragments of antibodies (e.g., scFv) derived therefrom, can be used in the present invention, as exemplified herein.

In other aspects, the localizing domain of the LD-linked target-binding molecule comprises an endoplasmic reticulum (ER) retention sequence KDEL (SEQ ID NO: 4), or other ER or Golgi retention sequences such as KKXX (SEQ ID NO: 9), KXD/E (SEQ ID NO: 10) (where X can be any amino acid—see Gao C, et al., *Trends in Plant Science* 19: 508-515, 2014) and YQRL (SEQ ID NO: 11) (see Zhan J, et al., *Cancer Immunol Immunother* 46:55-60, 1998); a proteosome targeting sequence that comprises, e.g., "PEST" motif—SHGFPPEVEEQDDGTLPMSCAQESGMDRHPAACASARINV (SEQ ID NO: 7); and/or a sequence that targets the target-binding molecule to the cell membrane, such as the CD8α transmembrane domain, or the transmembrane of another single-pass membrane protein, as described herein (e.g., CD8α, CD8β, 4-1BB, CD28, CD34, CD4, FcεRIγ, CD16 (such as CD16A or CD16B), OX40, CD3ζ, CD3ε, CD3γ, CD3δ, TCRα, CD32 (such as CD32A or CD32B), CD64 (such as CD64A, CD64B, or CD64C), VEGFR2, FAS, or FGFR2B). Examples of particular localizing domains (sequences) exemplified herein are shown in FIG. 2. Various other localizing sequences are known and available in the art.

As shown in FIG. 2, the LD-linked target-binding molecules of the present invention can comprise one or more localizing domains. For example, the LD-linked target-binding molecule can have at least one, at least two, at least three, at least four, at least five, at least six, at least seven, at least eight, at least nine, or at least ten localizing domains linked together. When more than one localizing domain is used in a given LD-linked target-binding molecule, each localizing domain can be linked with or without any intervening linker. By way of example, as shown in FIG. 2, localization domains CD8 TM, PEST motif, and EEKKMP can be used in a single LD-linked target-binding molecule. While this particular construct shows the localization domains without any intervening linkers, various intervening linkers can be incorporated between some or all of the localization domains. Other examples are shown in FIG. 2.

As would be appreciated by those of skill in the art, the immune activating receptor and/or the LD-linked target-binding molecule can be designed to bind to the targets disclosed herein, as well as variants of the targets disclosed herein. By way of example, an immune activating receptor and/or the LD-linked target-binding molecule can be designed to bind to a molecule in a CD3/TCR complex, or a naturally-occurring variant molecule thereof. Such naturally-occurring variants can have the same function as the wild-type form of the molecule. In other embodiments, the variant can have a function that is altered relative to the wild-type form of the molecule (e.g., confers a diseased state).

As would be appreciated by those of skill in the art, the various components of the LD-linked target-binding molecule constructs shown in FIG. 2 can be substituted in different combinations (e.g., to contain a different linker, different localizing sequence, different scFv, etc.), so long as the combination produces a functional LD-linked target-binding molecule. Methods of assessing functionality for a particular construct are within the ambit of those of skill in the art, as disclosed herein.

In further aspects, the present invention relates to the use of an engineered immune cell that comprises a nucleic acid comprising a nucleotide sequence encoding an immune activating receptor, and a nucleic acid comprising a nucleotide sequence encoding a target-binding molecule (e.g., scFv) linked to a localizing domain for treating cancer, comprising administering a therapeutic amount of the engineered immune cell to a subject in need thereof.

In another aspect, the present invention relates to the use of an engineered immune cell that comprises a nucleic acid comprising a nucleotide sequence encoding a chimeric antigen receptor (CAR) and a nucleic acid comprising a nucleotide sequence encoding a single-chain variable fragment (scFv) linked to a localizing domain for treating cancer, comprising administering a therapeutic amount of the engineered immune cell to a subject in need thereof.

In other aspects, the present invention relates to the use of an engineered immune cell that comprises a nucleic acid comprising a nucleotide sequence encoding an immune activating receptor, and a nucleic acid comprising a nucleotide sequence encoding a target-binding molecule (e.g., scFv) linked to a localizing domain for treating an autoimmune disorder, comprising administering a therapeutic amount of the engineered immune cell to a subject in need thereof.

In other aspects, the present invention also relates to the use of an engineered immune cell that comprises a nucleic acid comprising a nucleotide sequence encoding an immune activating receptor, and a nucleic acid comprising a nucleotide sequence encoding a target-binding molecule (e.g., scFv) linked to a localizing domain for treating an infectious disease, comprising administering a therapeutic amount of the engineered immune cell to a subject in need thereof.

In various embodiments, the immune activating receptor is a CAR (e.g., anti-CD19-4-1BB-CD3ζ CAR).

In other embodiments, the single-chain variable fragment (scFv) linked to a localizing domain is selected from any one or more constructs shown in FIG. 2.

In some aspects, the engineered immune cell is administered by infusion into the subject. Methods of infusing immune cells (e.g., allogeneic or autologous immune cells) are known in the art. A sufficient number of cells are administered to the recipient in order to ameliorate the symptoms of the disease. Typically, dosages of $10^7$ to $10^{10}$ cells are infused in a single setting, e.g., dosages of $10^9$ cells. Infusions are administered either as a single $10^9$ cell dose or divided into several $10^9$ cell dosages. The frequency of infusions can be every 3 to 30 days or even longer intervals if desired or indicated. The quantity of infusions is generally at least 1 infusion per subject and preferably at least 3 infusions, as tolerated, or until the disease symptoms have been ameliorated. The cells can be infused intravenously at a rate of 50-250 ml/hr. Other suitable modes of administration include intra-arterial infusion, direct injection into tumor and/or perfusion of tumor bed after surgery, implantation at the tumor site in an artificial scaffold, intrathecal administration, and intraocular administration. Methods of adapting the present invention to such modes of delivery are readily available to one skilled in the art.

In certain aspects, the cancer to be treated is a solid tumor or a hematologic malignancy. Examples of hematologic malignancies include acute myeloid leukemia, chronic myelogenous leukemia, myelodysplasia, acute lymphoblastic leukemia, chronic lymphocytic leukemia, multiple myeloma, Hodgkin and non-Hodgkin lymphoma. Examples of solid tumors include lung cancer, melanoma, breast cancer, prostate cancer, colon cancer, renal cell carcinoma, ovarian cancer, pancreatic cancer, hepatocellular carcinoma, neuroblastoma, rhabdomyosarcoma, brain tumor.

In another embodiment, the present invention relates to a method for producing an engineered immune cell of the present invention, comprising introducing into an immune cell a nucleic acid comprising a nucleotide sequence encoding an immune activating receptor, and a nucleic acid comprising a nucleotide sequence encoding a target-binding molecule linked to a localizing domain, thereby producing an engineered immune cell.

In certain embodiments, the nucleic acid comprising a nucleotide sequence is introduced into an immune cell ex vivo. In other embodiments, the nucleic acid comprising a nucleotide sequence is introduced into an immune cell in vivo.

In some embodiments, an "immune cell" includes, e.g., a T cell, a natural killer (NK) cell, an NK/T cell, a monocyte, a macrophage, or a dendritic cell.

The nucleic acid comprising a nucleotide sequence to be introduced can be a single bicistronic construct containing an immune activating receptor described herein and a target-binding molecule (e.g., scFv) linked to a localizing domain. As described herein, a single bicistronic construct can be prepared by inserting an internal ribosomal entry site (IRES) or a 2A peptide-coding region site between the 2 cDNAs encoding the immune activating receptor as described herein (e.g., CAR) and the target-binding molecule (e.g., scFv). The design of tricistronic delivery systems to delete more than one target should also be feasible. Alternatively, separate transductions (simultaneously or sequentially) of the individual constructs (e.g., CAR and LD-linked target-binding molecule) could be performed. Methods of introducing exogenous nucleic acids are exemplified herein, and are well-known in the art.

As used herein, the indefinite articles "a" and "an" should be understood to mean "at least one" unless clearly indicated to the contrary.

EXEMPLIFICATION

Methods

Cloning of scFv from Mouse Anti-Human CD3 Hybridoma
PLU4 hybridoma cells secreting an anti-human CD3 monoclonal antibody (IgG2a isotype; Creative Diagnostics, Shirley, NY) were cultured in IMDM plus GlutaMAX medium (Life Technologies, Carlsbad, CA) with 20% fetal bovine serum (Thermo Fisher Scientific, Waltham, MA) and antibiotics. Total RNA was extracted using TRIzol reagent (Life Technologies), and cDNA was synthesized by M-MLV reverse transcriptase (Promega, Madison, WI) and Oligo $(dT)_{15}$ primer (Promega). IgG Library Primer Set Mouse BioGenomics (US Biological, Salem, MA) was used to amplify the variable region of heavy chain (VH) and light chain (VL); PCR products were cloned into TOPO TA cloning kit for sequencing (Life Technologies). The VH and VL genes were assembled into scFv by a flexible linker sequence which encodes $(Gly_4Ser)_4$ using splicing by overlapping extension-PCR. Signal peptide domain of CD8α was subcloned by PCR using cDNA derived from human activated T cell from healthy donor, and connected to 5' end of the VL fragment. The Myc tag (EQKLISEEDL; SEQ ID NO: 1) was added to C-terminus of VH by PCR using sense primer: 5'-ATATATGAATTCGGCTTCCACCATGGCCT-TACCAGTGACC-3' (SEQ ID NO: 2) and reverse primer: 5'-CAGATCTTCTTCAGAAATAAGTTTTTGTTCGGCT-GAGGAGACTGTGAGAG-3'(SEQ ID NO: 3). Also the KDEL (SEQ ID NO: 4) coding sequence was generated after Myc tag by sense primer: 5'-ATATATGAATTCGGCTTC-CACCATGGCCTTACCAGTGACC-3' (SEQ ID NO: 5) and reverse primer: 5'-TATATACTCGAGTTACAACT-CGTCCTTCAGATCTTCTTCAGAAATAAG-3' (SEQ ID NO: 6). The synthesized gene consisting of CD8 signal peptide, scFv against human CD3, Myc tag and KDEL (SEQ ID NO: 4) sequence was subcloned into EcoRI and XhoI sites of the MSCV-IRES-GFP vector. Constructs in which myc-KDEL was replaced by other sequences were also made as listed in FIG. 2.

The sequence of "PEST"-SHGFPPEVEEQDDGTLPMS-CAQESGMDRHPAACASARINV (SEQ ID NO: 7) motif corresponding to amino acids 422-461 of mouse ornithine decarboxylase was obtained from GenBank (accession number NM_013614.2). Codon optimization and gene synthesis was done by GenScript (Piscataway, NJ), and subcloned into the 3' end of VH by PCR. The constructs were subcloned into EcoRI and XhoI sites of the MSCV-IRES-GFP vector.

Cloning of scFv Against Human CD7

The sequence scFv derived from murine TH69 (anti-CD7) antibody was obtained from literature (Peipp et al., *Cancer Res* 2002 (62): 2848-2855). After codon optimization, the synthesized gene consisting of CD8 signal peptide, scFv against human CD7, Myc tag and KDEL (SEQ ID NO: 4) sequence was subcloned into EcoRI and XhoI sites of the MSCV-IRES-GFP vector. Constructs in which myc-KDEL was replaced by other sequences were also made as listed in FIG. 2.

Cloning of scFv Against Human Beta-2 Microglobulin (hB2MG)

The sequence scFv derived from murine BBM.1 (anti-hB2MG) IgG2b antibody was obtained from literature (Grovender, E. A. et al., *Kidney Int.* 2004; 65(1):310-322). After codon optimization, synthesized gene consists of CD8 signal peptide, scFv against human B2MG, Myc tag and KDEL (SEQ ID NO: 4) sequence was subcloned into EcoRI and XhoI sites of the MSCV-IRES-GFP vector.

Cloning of scFv against human KIR2DL1 and KIR2DL2/DL3

The amino acid sequence of human monoclonal antibody I-7F9 (anti-KIR2DL1, KIR2DL2, and KIR2DL3) was derived from published International Patent Application WO2006003179 A2 by Moretta et al. After codon optimization, the sequence of scFv was designed by connecting variable light (VL) region and variable heavy (VH) region with linker sequence. The synthesized gene consisting of CD8 signal peptide, scFv against human KIRs (KIR2DL1, KIR2DL2 and KIR2DL3), CD8 hinge and transmembrane domain, and KKMP sequence was subcloned into EcoRI and XhoI sites of the MSCV-IRES-GFP vector. Constructs in which KKMP was replaced by other sequences were also made as listed in FIG. 2.

Cloning of scFv Against Human NKG2A

The sequence of murine antibody Z199 (anti-NKG2A) was derived from the published patent by Spee et al. (EP2247619 A1). After codon optimization, the sequence of scFv was designed by connecting variable light (VL) region and variable heavy (VH) region with linker sequence. The synthesized gene consisting of CD8 signal peptide, scFv against human NKG2A, CD8 hinge and transmembrane, and KKMP sequence was subcloned into EcoRI and XhoI sites of the MSCV-IRES-GFP vector. Constructs in which KKMP was replaced by other sequences were also made as listed in FIG. 2. The sequence information for the scFvs generated herein is shown in Table 1. Sequence information for the various components depicted in FIG. 2 is shown in Table 2.

Anti-CD19-4-1BB-CD3ζ CAR

This CAR was generated as previously described (Imai, C. et al., *Leukemia*. 2004; 18:676-684; Imai, C. et al., *Blood*. 2005; 106:376-383).

TABLE 1 scFv sequence information

| Target | VH amino acid | VL amino acid | VH cDNA | VL cDNA |
|---|---|---|---|---|
| CD3 | EVQLQQSGAELAR PGASVKMSCKAS GYTFTRYTMHWV KQRPGQGLEWIGY INPSRGYTNYNQK FKDKATLTTDKSS STAYMQLSSLTSE DSAVYYCARYYD DHYCLDYWGQGT TLTVSSA (SEQ ID NO: 12) | QIVLTQSPAIMSA SPGEKVTMTCSAS SSVSYMNWYQQ KSGTSPKRWIYDT SKLASGVPAHFR GSGSGTSYSLTIS GMEAEDAATYYC QQWSSNPFTFGSG TKLEINR (SEQ ID NO: 13) | GAGGTCCAGCTGCAGCAG TCTGGGGCTGAACTGGCA AGACCTGGGGCCTCAGTG AAGATGTCCTGCAAGGCTT CTGGCTACACCTTTACTAG GTACACGATGCACTGGGT AAAACAGAAGTCAGGCAC GGGTCTGGAATGGATTGG ATACATTAATCCTAGCCGT GGTTATACTAATTACAATC AGAAGTTCAAGGACAAGG CCACATTGACTACAGACA AATCCTCCAGCACAGCCTA CATGCAACTGAGCAGCCT GACATCTGAGGACTCTGCA GTCTATTACTGTGCAAGAT ATTATGATGATCATTACTG CCTTGACTACTGGGGCCAA GGCACCACTCTCACAGTCT CCTCAGCC (SEQ ID NO: 14) | CAAATTGTTCTCACCCAG TCTCCAGCAATCATGTCT GCATCTCCAGGGGAGAA GGTCACCATGACCTGCA GTGCCAGCTCAAGTGTA AGTTACATGAACTGGTAC CAGCAGAAGTCAGGCAC CTCCCCCAAAAGATGGA TTTATGACACATCCAAAC TGGCTTCTGGAGTCCCTG CTCACTTCAGGGGCAGTG GGTCTGGGACCTCTTACT CTCTCACAATCAGCGGCA TGGAGGCTGAAGATGCT GCCACTTATTACTGCCAG CAGTGGAGTAGTAACCC ATTCACGTTCGGCTCGGG GACAAAGTTGGAAATAA ACCGG (SEQ ID NO: 15) |
| CD7 (TH69) | EVQLVESGGGLVK PGGSLKLSCAASG LTFSSYAMSWVR QTPEKRLEWVASI SSGGFTYYPDSVK GRFTISRDNARNIL YLQMSSLRSEDTA MYYCARDEVRGY LDVWGAGTTVTV SS (SEQ ID NO: 16) | AAYKDIQMTQTT SSLSASLGDRVTIS CSASQGISNYLN WYQQKPDGTVKL LIYYTSSLHSGVP SRFSGSGSGTDYS LTISNLEPEDIATY YCQQYSKLPYTF GGGTKLEIKR (SEQ ID NO: 17) | GAGGTGCAGCTGGTCGAA TCTGGAGGAGGACTGGTG AAGCCAGGAGGATCTCTG AAACTGAGTTGTGCCGCTT CAGGCCTGACCTTCTCAAG CTACGCCATGAGCTGGGTG CGACAGACACCTGAGAAG CGGCTGGAATGGGTCGCT AGCATCTCCTCTGGCGGGT TCACATACTATCCAGACTC CGTGAAAGGCAGATTTACT ATCTCTCGGGATAACGAA GAAATATTCTGTACCTGCA GATGAGTTCACTGAGGAG CGAGGACACCGCAATGTA CTATTGTGCCAGGGACGA AGTGCGCGGCTATCTGGAT GTCTGGGGAGCTGGCACT ACCGTCACCGTCTCCAGC (SEQ ID NO: 18) | GCCGCATACAAGGATAT TCAGATGACTCAGACCA CAAGCTCCCTGAGCGCCT CCCTGGGAGACCGAGTG ACAATCTCTTGCAGTGCA TCACAGGGAATTAGCAA CTACCTGAATTGGTATCA GCAGAAGCCAGATGCA CTGTGAAACTGCTGATCT ACTATACCTCTAGTCTGC ACAGTGGGGTCCCCTCAC GATTCAGCGGATCCGGCT CTGGGACAGACTACAGC CTGACTATCTCCAACCTG GAGCCCGAAGATATTGC CACCTACTATTGCCAGCA GTACTCCAAGCTGCCTTA TACCTTTGGCGGGGGAA CAAAGCTGGAGATTAAA AGG (SEQ ID NO: 19) |
| CD7 (3alf) | QVQLQESGAELVK PGASVKLSCKASG YTFTSYWMHWVK QRPGQGLEWIGKI NPSNGRTNYNEKF KSKATLTVDKSSS TAYMQLSSLTSED SAVYYCARGGVY YDLYYYALDYWG QGTTVTVSS (SEQ ID NO: 20) | DIELTQSPATLSVT PGDSVSLSCRASQ SISNNLHWYQQK SHESPRLLIKSASQ SISGIPSRFSGSGS GTDFTLSINSVETE DFGMYFCQQSNS WPYTFGGGTKLEI KR (SEQ ID NO: 21) | CAGGTCCAGCTGCAGGAG TCAGGGGCAGAGCTGGTG AAACCCGGAGCCAGTGTC AAACTGTCCTGTAAGGCCA GCGGCTATACTTTCACCAG CTACTGGATGCACTGGGTG AAACAGAGGCCAGGACAG GGCCTGGAGTGGATCGGC AAGATTAACCCCAGCAAT GGGCGCACCAACTACAAC GAAAAGTTTAAATCCAAG GCTACACTGACTGTGGACA AGAGCTCCTCTACCGCATA CATGCAGCTGAGTTCACTG ACATCTGAAGATAGTGCC | GACATCGAGCTGACACA GTCTCCAGCCACTCTGAG CGTGACCCCTGGCGATTC TGTCAGTCTGTCATGTAG AGCTAGCCAGTCCATCTC TAACAATCTGCACTGGTA CCAGCAGAAATCACATG AAAGCCCTCGGCTGCTG ATTAAGAGTGCTTCACAG AGCATCTCCGGGATTCCA AGCAGATTCTCTGGCAGT GGGTCAGGAACCGACTT TACACTGTCCATTAACTC TGTGGAGACCGAAGATT TCGGCATGTATTTTTGCC |

TABLE 1-continued scFv sequence information

| Target | VH amino acid | VL amino acid | VH cDNA | VL cDNA |
|---|---|---|---|---|
| | | | GTGTACTATTGCGCCAGAG GCGGGGTCTACTATGACCT GTACTATTACGCACTGGAT TATTGGGGGCAGGGAACC ACAGTGACTGTCAGCTCC (SEQ ID NO: 22) | AGCAGAGCAATTCCTGG CCTTACACATTGGAGGC GGGACTAAACTGGAGAT TAAGAGG (SEQ ID NO: 23) |
| CD45 | QVQLVESGGGLV QPGGSLKLSCAAS GFDFSRYWMSWV RQAPGKGLEWIGE INPTSSTINFTPSLK DKVFISRDNAKNT LYLQMSKVRSEDT ALYYCARGNYYR YGDAMDYWGQG TSVTVS (SEQ ID NO: 24) | DIVLTQSPASLAV SLGQRATISCRAS KSVSTSGYSYLH WYQQKPGQPPKL LIYLASNLESGVP ARFSGSGSGTDFT LNIHPVEEEDAAT YYCQHSRELPFTF GSGTKLEIK (SEQ ID NO: 25) | CAGGTGCAGCTGGTCGAG TCTGGAGGAGGACTGGTG CAGCCTGGAGGAAGTCTG AAGCTGTCATGTGCAGCCA GCGGGTTCGACTTTTCTCG ATACTGGATGAGTTGGGTG CGGCAGGCACCAGGAAAA GGACTGGAATGGATCGGC GAGATTAACCCAACTAGCT CCACCATCAATTTCACACC CAGCCTGAAGGACAAAGT GTTTATTTCCAGAGATAAC GCCAAGAATACTCTGTATC TGCAGATGTCCAAAGTCA GGTCTGAAGATACCGCCCT GTACTATTGTGCTCGGGGC AACTACTATAGATACGGG GACGCTATGGATTATTGGG GGCAGGGAACTAGCGTGA CCGTGAGT (SEQ ID NO: 26) | GACATTGTGCTGACCCAG TCCCCTGCTTCACTGGCA GTGAGCCTGGGACAGAG GGCAACCATCAGCTGCC GAGCCTCTAAGAGTGTCT CAACAAGCGGATACTCC TATCTGCACTGGTACCAG CAGAAGCCAGGACAGCC ACCTAAACTGCTGATCTA TCTGGCTTCCAACCTGGA ATCTGGAGTGCCTGCACG CTTCTCCGGATCTGGAAG TGGAACCGACTTTACACT GAATATTCACCCAGTCGA GGAAGAGGATGCCGCTA CCTACTATTGCCAGCACA GCCGGGAGCTGCCCTTCA CATTTGGCAGCGGGACT AAGCTGGAGATCAAG (SEQ ID NO: 27) |
| B2MG | EVQLQQSGAELVK PGASVKLSCTPSG FNVKDTYIHWVK QRPKQGLEWIGRI DPSDGDIKYDPKF QGKATITADTSSN TVSLQLSSLTSEDT AVYYCARWFGDY GAMNYWGQGTSV TVSS (SEQ ID NO: 28) | DIQMTQSPASQSA SLGESVTITCLAS QTIGTWLAWYQQ KPGKSPQLLIYAA TSLADGVPSRFSG SGSGTKFSLKIRT LQAEDFVSYYCQ QLYSKPYTFGGG TKLEIKRAD (SEQ ID NO: 29) | GAGGTGCAGCTGCAGCAG AGCGGAGCAGAACTGGTG AAACCTGGAGCCAGCGTC AAGCTGTCCTGTACTCCAT CTGGCTTCAACGTGAAGG ACACATACATTCACTGGGT CAAGCAGCGGCCCAAACA GGGACTGGAGTGGATCGG CAGAATTGACCCATCCGAC GGCGATATCAAGTATGATC CCAAATTCCAGGGGAAGG CTACTATTACCGCAGATAC CAGCTCCAACACAGTGAG TCTGCAGCTGTCTAGTCTG ACTAGCGAAGACACCGCC GTCTACTATTGTGCTAGAT GGTTTGGCGATTACGGGGC CATGAATTATTGGGGGCA GGGAACCAGCGTCACCGT GTCCAGC (SEQ ID NO: 30) | GATATTCAGATGACCCA GTCCCCTGCATCACAGAG CGCCTCCCTGGGCGAGTC AGTGACCATCACATGCCT GGCTAGCCAGACAATTG GCACTTGGCTGGCATGGT ACCAGCAGAAGCCCGGC AAATCCCCTCAGCTGCTG ATCTATGCAGCTACCTCT CTGGCAGACGGAGTGCC CAGTAGGTTCTCTGGGAG TGGATCAGGCACCAAGT TTTCTCTGAAAATTCGCA CACTGCAGGCTGAGGAT TTCGTCTCCTACTATTGC CAGCAGCTGTACTCTAAA CCTTATACATTTGGCGGG GGAACTAAGCTGGAAAT CAAACGAGCAGAC (SEQ ID NO: 31) |
| NKG2A | EVQLVESGGGLVK PGGSLKLSCAASG FTFSSYAMSWVRQ SPEKRLEWVAEISS GGSYTYYPDTVTG RFTISRDNAKNTL YLEISSLRSEDTAM YYCTRHGDYPRFF DVWGAGTTVTVS S (SEQ ID NO: 32) | QIVLTQSPALMSA SPGEKVTMTCSAS SSVSYIYWYQQK PRSSPKPWIYLTS NLASGVPARFSGS GSGTSYSLTISSM EAEDAATYYCQQ WSGNPYTFGGGT KLEIKR (SEQ ID NO: 33) | GAGGTGCAGCTGGTGGAG AGCGGAGGAGGACTGGTG AAGCCCAGGAGGACTTG GCCTCCCCTGGCGAGAA AAGCTGTCCTGTGCCGCT CTGGCTTCACATTTTCCTC TTATGCAATGAGCTGGGTG CGGCAGTCCCCAGAGAAG AGACTGGAGTGGGTCGCA GAGATCAGCTCCGGAGGA TCCTACACCTACTATCCTG ACACAGTGACCGGCCGGT TCACAATCTCTAGAGATAA CGCCAAGAATACCCTGTAT CTGGAGATCTCTAGCCTGA GATCCGAGGATACAGCCA TGTACTATTGCACCAGGCA CGGCGACTACCCACGCTTC TTTGACGTGTGGGGAGCA GGAACCACAGTGACCGTG TCCTCT (SEQ ID NO: 34) | CAGATTGTCCTGACCCAG TCTCCAGCCCTGATGAGC GCCTCCCCTGGCGAGAA GGTGACAATGACCTGCTC TGCCAGTCCTCTGTGAG CTACATCTATTGGTACCA GCAGAAGCCTCGGAGCT CCCCAAAGCCCTGGATCT ATCTGACATCCAACCTGG CCTCTGGCGTGCCAGCCA GATTCTCTGGCAGCGGCT CCGGCACATCTTACAGCC TGACCATCTCTAGCATGG AGGCCGAGGACGCCGCC ACCTACTATTGCCAGCAG TGGTCCGGCAATCCATAT ACATTTGGCGGCGGCAC CAAGCTGGAGATCAAGA GG (SEQ ID NO: 35) |
| KIR 2DL1 and 2/3 | QVQLVQSGAEVK KPGSSVKVSCKAS GGTFSFYAISWVR | EIVLTQSPVTLSLS PGERATLSCRASQ SVSSYLAWYQQK | CAGGTCCAGCTGGTGCAGT CTGGAGCTGAAGTGAAGA AACCAGGGAGCTCCGTCA | GAGATCGTGCTGACCCA GTCTCCTGTCACACTGAG TCTGTCACCAGGGGAAC |

TABLE 1-continued scFv sequence information

| Target | VH amino acid | VL amino acid | VH cDNA | VL cDNA |
|---|---|---|---|---|
| | QAPGQGLEWMGG FIPIFGAANYAQKF QGRVTITADESTST AYMELSSLRSDDT AVYYCARiPSGSY YYDYDMDVWGQ GTTVTVSS (SEQ ID NO: 36) | PGQAPRLLIYDAS NRATGIPARFSGS GSGTDFTLTISSLE PEDFAVYYCQQR SNWMYTFGQGTK LEIKRT (SEQ ID NO: 37) | AGGTGTCATGCAAAGCAA GCGGCGGGACTTTCTCCTT TTATGCAATCTCTTGGGTG AGACAGGCACCTGGACAG GGACTGGAGTGGATGGGA GGCTTCATCCCAATTTTTG GAGCCGCTAACTATGCCCA GAAGTTCCAGGGCAGGGT GACCATCACAGCTGATGA GTCTACTAGTACCGCATAC ATGGAACTGTCTAGTCTGA GGAGCGACGATACCGCCG TGTACTATTGTGCTCGCAT TCCATCAGGCAGCTACTAT TACGACTATGATATGGACG TGTGGGGCCAGGGGACCA CAGTCACCGTGAGCAGC (SEQ ID NO: 38) | GGGCTACACTGTCTTGCA GAGCAAGCCAGTCCGTG AGCTCCTACCTGGCCTGG TATCAGCAGAAGCCAGG CCAGGCTCCCAGGCTGCT GATCTACGATGCAAGCA ACAGGGCCACTGGGATT CCCGCCCGCTTCTCTGGC AGTGGGTCAGGAACCGA CTTTACTCTGACCATTTC TAGTCTGGAGCCTGAAG ATTTCGCCGTGTACTATT GCCAGCAGCGATCCAAT TGGATGTATACTTTTGGC CAGGGGACCAAGCTGGA GATCAAACGGACA (SEQ ID NO: 39) |

TABLE 2

Sequence information for components depicted in FIG. 2

| Target | CD8 SP amino acid | VH-VL linker amino acid | CD8 hinge and TM amino acid | CD8 SP cDNA | VH-VL linker cDNA | CD8 hinge and TM cDNA |
|---|---|---|---|---|---|---|
| CD3 | MALPVT ALLLPLA LLLHAAR P (SEQ ID NO: 40) | GGGGSGG GGSGGGG SGGGGS (SEQ ID NO: 41) | KPTTTPAPRPPTP APTIASQPLSLRP EACRPAAGGAVH TRGLDFACDIYI WAPLAGTCGVLL LSLVITLY (SEQ ID NO: 42) | ATGGCCTTACC AGTGACCGCCT TGCTCCTGCCG CTGGCCTTGCT GCTCCACGCCG CCAGGCCG (SEQ ID NO: 44) | GGTGGTGGTG GTTCTGGTGG TGGTGGTTCT GGCGGCGGCG GCTCCGGTGG TGGTGGATCC (SEQ ID NO: 51) | AAGCCCACCACG ACGCCAGCGCCG CGACCACCAACA CCGGCGCCCACC ATCCGCGTCGCAG CCCCTGTCCCTGC GCCCAGAGGCGT GCCGGCCAGCGG CGGGGGGCGCAG TGCACACGAGGG GGCTGGACTTCG CCTGTGATATCTA CATCTGGGCGCC CTTGGCCGGGAC TTGTGGGGTCCTT CTCCTGTCACTGG TTATCACCCTTTA C (SEQ ID NO: 57) |
| CD7 (TH69) | MALPVT ALLLPLA LLLHAAR P (SEQ ID NO: 40) | GGGGSGG GGSGGGG SGGGGS (SEQ ID NO: 41) | TTTPAPRPPTPAP TIASQPLSLRPEA CRPAAGGAVHTR GLDFACDIYIWA PLAGTCGVLLLS LVITLY (SEQ ID NO: 50) | ATGGCTCTGCC TGTGACCGCAC TGCTGCTGCCC CTGGCTCTGCT GCTGCACGCCG CAAGACCT (SEQ ID NO: 45) | GGAGGAGGAG GAAGCGGAGG AGGAGGATCC GGAGGCGGGG GATCTGGAGG AGGAGGAAGT (SEQ ID NO: 52) | ACCACTACACCT GCACCAAGGCCT CCCACACCCGCTC CCACTATCGCTTC CCAGCCACTGTCC CTGAGGCCCGAG GCCTGCAGGCCA GCAGCTGGCGGA GCCGTGCATACT AGGGGGCTGGAC TTCGCTTGCGACA TCTATATCTGGGC CCCACTGGCAGG GACATGCGGAGT CCTGCTGCTGTCC CTGGTCATCACAC TTTAC (SEQ ID NO: 58) |
| CD7 (3a1f) | MALPVT ALLLPLA LLLHAAR P (SEQ ID NO: 40) | GGGGSGG GGSGGGG S (SEQ ID NO: 43) | TTTPAPRPPTPAP TIASQPLSLRPEA CRPAAGGAVHTR GLDFACDIYIWA PLAGTCGVLLLS LVITLY (SEQ ID NO: 50) | ATGGCTCTGCC CGTGACCGCTC TGCTGCTGCCT CTGGCTCTGCT GCTGCACGCTG CTCGACCA (SEQ ID NO: | GGAGGAGGAG GATCCGGCGG AGGAGGCTCT GGGGGAGGCG GGAGT (SEQ ID NO: 53) | ACTACCACACCA GCTCCAAGACCA CCTACCCCTGCAC CAACAATTGCTA GTCAGCCACTGTC ACTGAGACCAGA AGCATGTAGGCC |

TABLE 2-continued

Sequence information for components depicted in FIG. 2

| Target | CD8 SP amino acid | VH-VL linker amino acid | CD8 hinge and TM amino acid | CD8 SP cDNA | VH-VL linker cDNA | CD8 hinge and TM cDNA |
|---|---|---|---|---|---|---|
| | | | | | 46) | TGCAGCTGGAGG AGCTGTGCACAC CAGAGGCCTGGA CTTTGCCTGCGAT ATCTACATTTGGG CTCCTCTGGCAGG AACCTGTGGCGT GCTGCTGCTGTCT CTGGTCATCACAC TTTAC (SEQ ID NO: 59) |
| CD45 | MALPVT ALLLPLA LLLHAAR P (SEQ ID NO: 40) | GGGGSGG GGSGGGG SGGGGS (SEQ ID NO: 41) | KPTTTPAPRPPTP APTIASQPLSLRP EACRPAAGGAVH TRGLDFACDIYI WAPLAGTCGVLL LSLVITLY (SEQ ID NO: 42) | ATGGCTCTGCC CGTGACCGCTC TGCTGCTGCCT CTGGCTCTGCT GCTGCATGCTG CTCGACCT (SEQ ID NO: 47) | GGAGGAGGAG GAAGTGGAGG GGAGGCGGGG GAAGCGGCGG GGGAGGCTCC (SEQ ID NO: 54) | AAGCCCACCACG ACGCCAGCGCCG CGACCACCAACA CCGGCGCCCACC ATCGCGTCGCAG CCCCTGTCCCTGC GCCCAGAGGCGT GCCGGCCAGCGG CGGGGGGCGCAG TGCACACGAGGG GGCTGGACTTCG CCTGTGATATCTA CATCTGGGCGCC CTTGGCCGGGAC TTGTGGGGTCCTT CTCCTGTCACTGG TTATCACCCTTTA C (SEQ ID NO: 57) |
| B2MG | MALPVT ALLLPLA LLLHAAR P (SEQ ID NO: 40) | GGGGSGG GGSGGGG SGGGGS (SEQ ID NO: 41) | KPTTTPAPRPPTP APTIASQPLSLRP EACRPAAGGAVH TRGLDFACDIYI WAPLAGTCGVLL LSLVITLY (SEQ ID NO: 42) | ATGGCCCTGCC CGTCACCGCCC TGCTGCTGCCC CTGGCTCTGCT GCTGCACGCCG CAAGACCC (SEQ ID NO: 48) | GGAGGAGGAG GAAGTGGAGG AGGAGGGTCA GGAGGCGGGG GAAGCGGCGG GGGAGGATCC (SEQ ID NO: 55) | AAGCCCACCACG ACGCCAGCGCCG CGACCACCAACA CCGGCGCCCACC ATCGCGTCGCAG CCCCTGTCCCTGC GCCCAGAGGCGT GCCGGCCAGCGG CGGGGGGCGCAG TGCACACGAGGG GGCTGGACTTCG CCTGTGATATCTA CATCTGGGCGCC CTTGGCCGGGAC TTGTGGGGTCCTT CTCCTGTCACTGG TTATCACCCTTTA C (SEQ ID NO: 57) |
| NKG2A | MALPVT LLLPLAA LLLHAAR P (SEQ ID NO: 40) | GGGGSGG GGSGGGG SGGGGS (SEQ ID NO: 41) | KPTTTPAPRPPTP APTIASQPLSLRP EACRPAAGGAVH TRGLDFACDIYI WAPLAGTCGVLL LSLVITLY (SEQ ID NO: 42) | ATGGCTCTGCC CGTGACCGCCC TGCTGCTGCCT CTGGCTCTGCT GCTGCACGCTG CCCGCCCA (SEQ ID NO: 49) | GGAGGAGGAG GATCTGGAGG AGGAGGCAGC GGCGGCGGCG GCTCCGGCGG CGGCGGCTCT (SEQ ID NO: 56) | AAGCCAACCACA ACCCCTGCACCA AGGCCACCTACA CCAGCACCTACC ATCGCAAGCCAG CCACTGTCCCTGA GGCCAGAGGCAT GTAGGCCTGCAG CAGGAGGCGCCG TGCACACACGCG GCCTGGACTTTGC CTGCGATATCTAC ATCTGGGCACCA CTGGCAGGAACC TGTGGCGTGCTGC TGCTGAGCCTGGT GATTACCCTGTAT (SEQ ID NO: 60) |
| KIR 2DL1 | MALPVT ALLLPLA | GGGGSGG GGSGGGG | KPTTTPAPRPPTP APTIASQPLSLRP | ATGGCCTTACC AGTGACCGCCT | GGTGGTGGTG GTTCTGGTGG | AAGCCCACCACG ACGCCAGCGCCG |

TABLE 2-continued

Sequence information for components depicted in FIG. 2

| Target | CD8 SP amino acid | VH-VL linker amino acid | CD8 hinge and TM amino acid | CD8 SP cDNA | VH-VL linker cDNA | CD8 hinge and TM cDNA |
|---|---|---|---|---|---|---|
| and 2/3 | LLLHAARP (SEQ ID NO: 40) | SGGGGS (SEQ ID NO: 41) | EACRPAAGGAVH TRGLDFACDIYI WAPLAGTCGVLL LSLVITLY (SEQ ID NO: 42) | TGCTCCTGCCG CIGGCcrTGur GCTCCACGCCG CCAGGCCG (SEQ ID NO: 44) | TGGTGGTTCT GGCGGCGGCG GCTCCGGTGG TGGTGGATCC (SEQ ID NO: 51) | CGACCACCAACA CCGGCGCCCACC ATCGCGTCGCAG CCCCTGTCCCTGC GCCCAGAGGCGT GCCGGCCAGCGG CGGGGGGCGCAG TGCACACGAGGG GGCTGGACTTCG CCTGTGATATCTA CATCTGGGCGCC CTTGGCCGGGAC TTGTGGGGTCCTT CTCCTGTCACTGG TTATCACCCTTTA C (SEQ ID NO: 57) |

Gene Transduction, Cell Expansion, Flow Cytometric Analysis and Functional Studies These were performed as previously described (Kudo, K et al., *Cancer Res.* 2014; 74(1):93-103).

Results

Generation of scFv Constructs

Figure 1B:
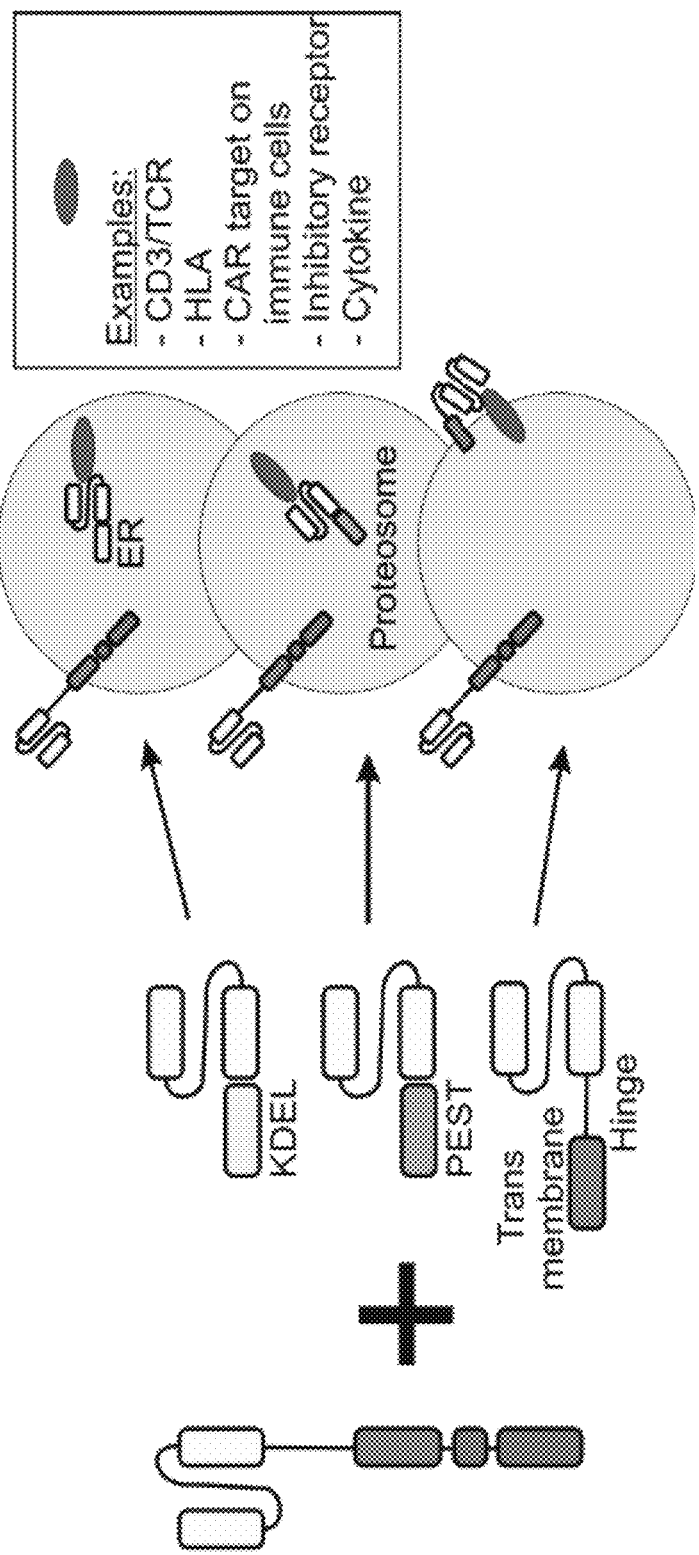

A schematic of the technology is outlined in FIG. 1. A schematic representation of the inhibitory constructs that we generated is shown in FIG. 2. The scFv portion can be derived by cloning the cDNA encoding variable light (VL) and variable heavy (VH) immunoglobulin chain regions from an antibody-producing hybridoma cell line or from the corresponding published sequences. VL and VH are linked with a short peptide sequence ("linker") according to standard techniques to make a full scFv. To be expressed, the scFv is linked to a signal peptide at the N-terminus; the signal peptide is required for the scFv to be expressed, as confirmed in preliminary experiments. Proteins containing scFv plus signal peptide are generally released into the cells' milieu. For example, in preliminary experiments (not shown), an anti-CD3ε scFv plus signal peptide expressed in Jurkat T cells was detected in the cells' culture supernatant. By directing the scFv to specific compartments and preventing its secretion, possible effects on other cells are prevented. To direct it to the endoplasmic reticulum (ER), the KDEL (SEQ ID NO: 4) motif (which retains proteins in the ER) was utilized (Strebe N. et al., *J Immunol Methods.* 2009; 341(1-2):30-40). To promote the degradation of the targeted protein, we linked it to a proteasome-targeting PEST motif (Joshi, S. N. et al., MAbs. 2012; 4(6):686-693). The scFv can also be directed to the cell membrane by linking it to the transmembrane domain and hinge of CD8α or another transmembrane protein.

Downregulation of T-Cell Receptor in T Lymphocytes Expressing Anti-CD19-BB-ζ CAR To determine whether the proposed strategy could be applied to generate immune cells expressing CAR and lacking one or more markers, T-cell receptor (TCR) expression was downregulated in anti-CD19 CAR T-cells.

To be expressed on the cell membrane, the CD3/TCR complex requires assembly of all its components (TCRα, TCRβ, CD3δ, CD3ε, CD3γ, CD3ζ). Lack of one component prevents CD3/TCR expression and, therefore, antigen recognition. In preliminary studies, the scFv from an anti-CD3ε hybridoma (purchased from Creative Diagnostics, Shirley, NY) was cloned and generated the constructs containing KDEL (SEQ ID NO: 4), PEST, CD8α transmembrane domain or others as shown in FIG. 2.

Figure 3C:
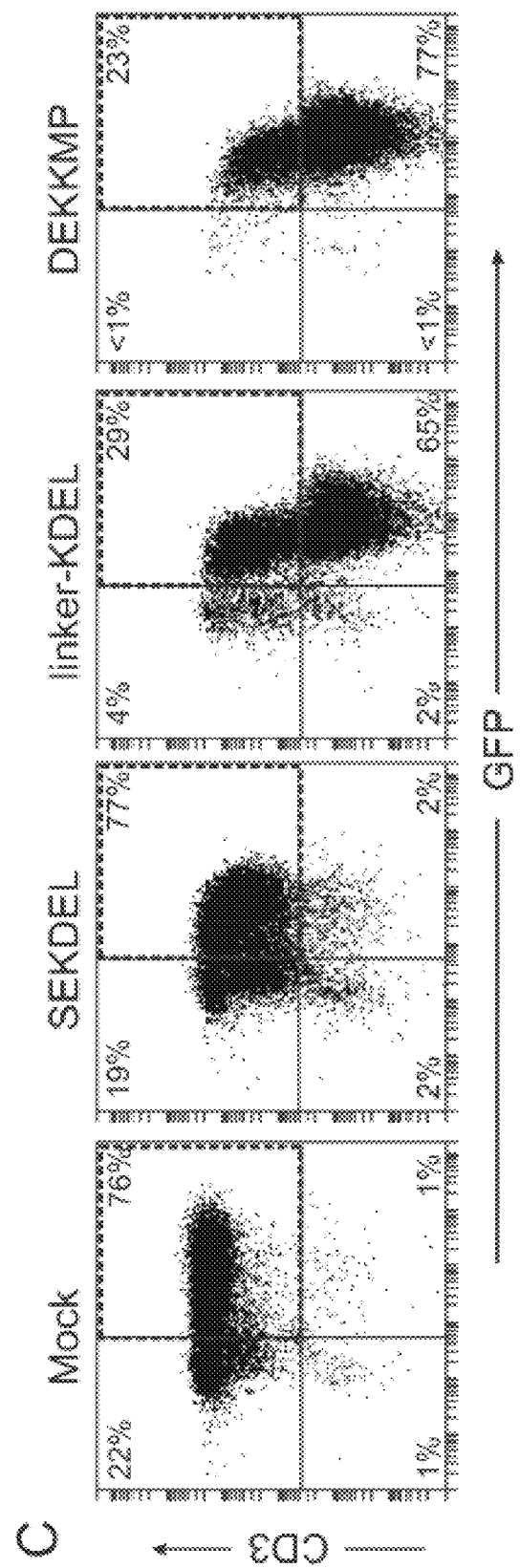

The constructs disclosed herein were transduced in the CD3/TCR+ Jurkat cell line using a murine stem cell virus (MSCV) retroviral vector containing green fluorescent protein (GFP). Percentage of GFP+ cells after transduction was >90% in all experiments. FIG. 3A shows results of staining with anti-CD3ε antibody among GFP+ cells, as measured by flow cytometry. Antibody staining of CD3ε was decreased to variable degree in cells transduced with the constructs listed. Similar downregulation of CD3ε was obtained with human peripheral blood T lymphocytes (FIG. 3B). FIG. 3C shows illustrative flow cytometry dot plots of CD3ε expression in GFP-positive Jurkat cells after transduction with different gene constructs in comparison with cells transduced with a vector containing GFP alone. Downregulation of CD3 did not affect growth of Jurkat cells or expression of all other cell markers tested, including CD2, CD4, CD8, CD45, CD25, CD69. Inhibition of CD3 expression persisted for over 3 months. Further enrichment of CD3-negative cells could be achieved by CD3+ T cell depletion with anti-CD3 magnetic beads (Dynal, Life Technologies, Carlsbad, CA).

Figure 4:
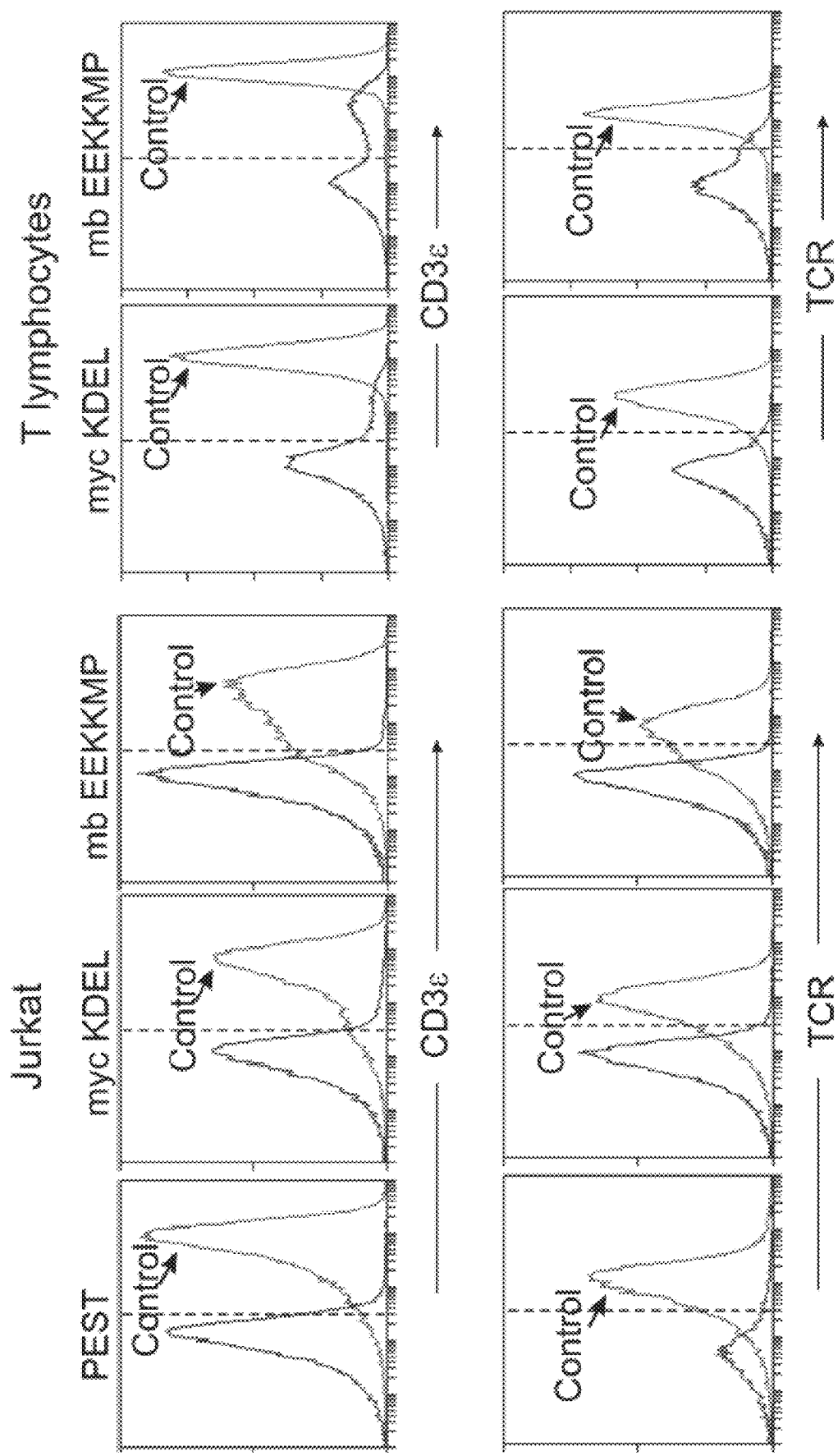
FIG. 4 shows downregulation of CD3ε and TCRαβ on the cell membrane in Jurkat T cells upon transduction with anti-CD3ε scFv-KDEL or -PEST, or -mb EEKKMP. Membrane marker expression was measured 1 week after transduction using an anti-CD3 antibody conjugated to allophycocyanin (BD Biosciences) or an anti-TCRαβ conjugated to phycoerythrin (Biolegend). Lines labeled "Control" represent labelling of mock-transduced cells. Dashed vertical line represents the upper limit of staining obtained with an isotype-matched non-reactive antibody.

Staining with anti-TCRαβ antibody of Jurkat cells or human peripheral blood T lymphocytes showed that down regulation of CD3ε expression was associated with downregulation of TCRαβ expression (FIG. 4).

Figure 5:
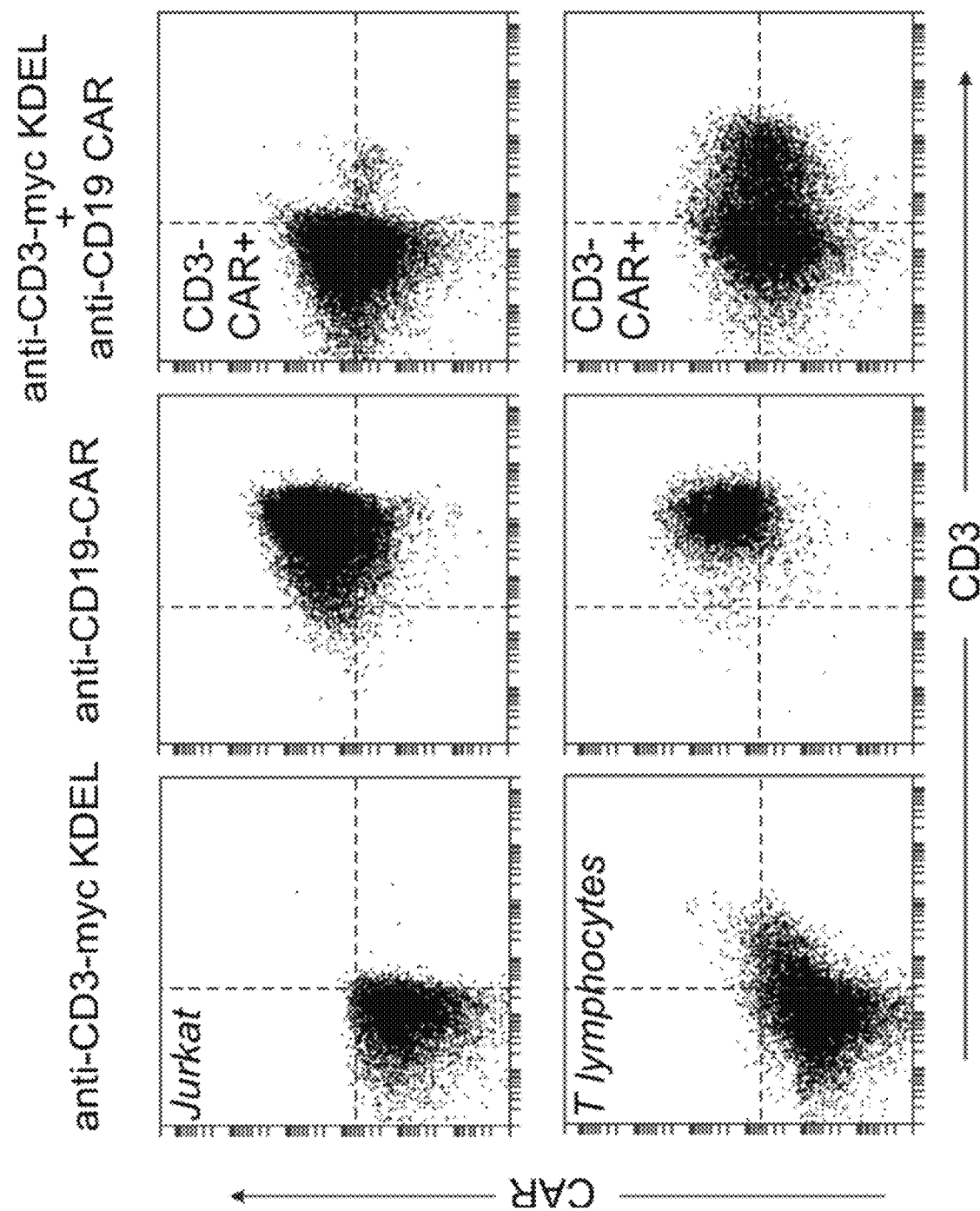
FIG. 5 shows that anti-scFv and CAR can be expressed simultaneously. Flow cytometric dot plots represent staining of Jurkat cells (top row) or peripheral blood lymphocytes (bottom row) with anti-CD3 allophycocyanin antibody and goat-anti-mouse Fab2 biotin plus streptavidin conjugated to phycoerythrin (to detect the CAR). Cells were transduced with the anti-CD3 scFv-myc KDEL construct, the anti-CD19-4-1BB-CD3ζ construct, or both. After gating on GFP-positive cells, those transduced with anti-CD3 scFv-myc KDEL downregulated CD3 (left column, bottom left quadrants) and those transduced with the anti-CD19-4-1BB-CD3ζ construct expressed the CAR (middle column, top right quadrants). A substantial proportion of cells transduced with both constructs were CD3-negative and CAR-positive (right column, top left quadrants).

Next, it was determined whether the anti-CD3 scFv-myc KDEL could be expressed simultaneously with an anti-CD19-4-1BB-CD3ζ CAR. As shown in FIG. 5, this resulted in T cells lacking CD3 expression while expressing the anti-CD19 CAR. TCR was also absent on these cells (not shown).

Figure 6:
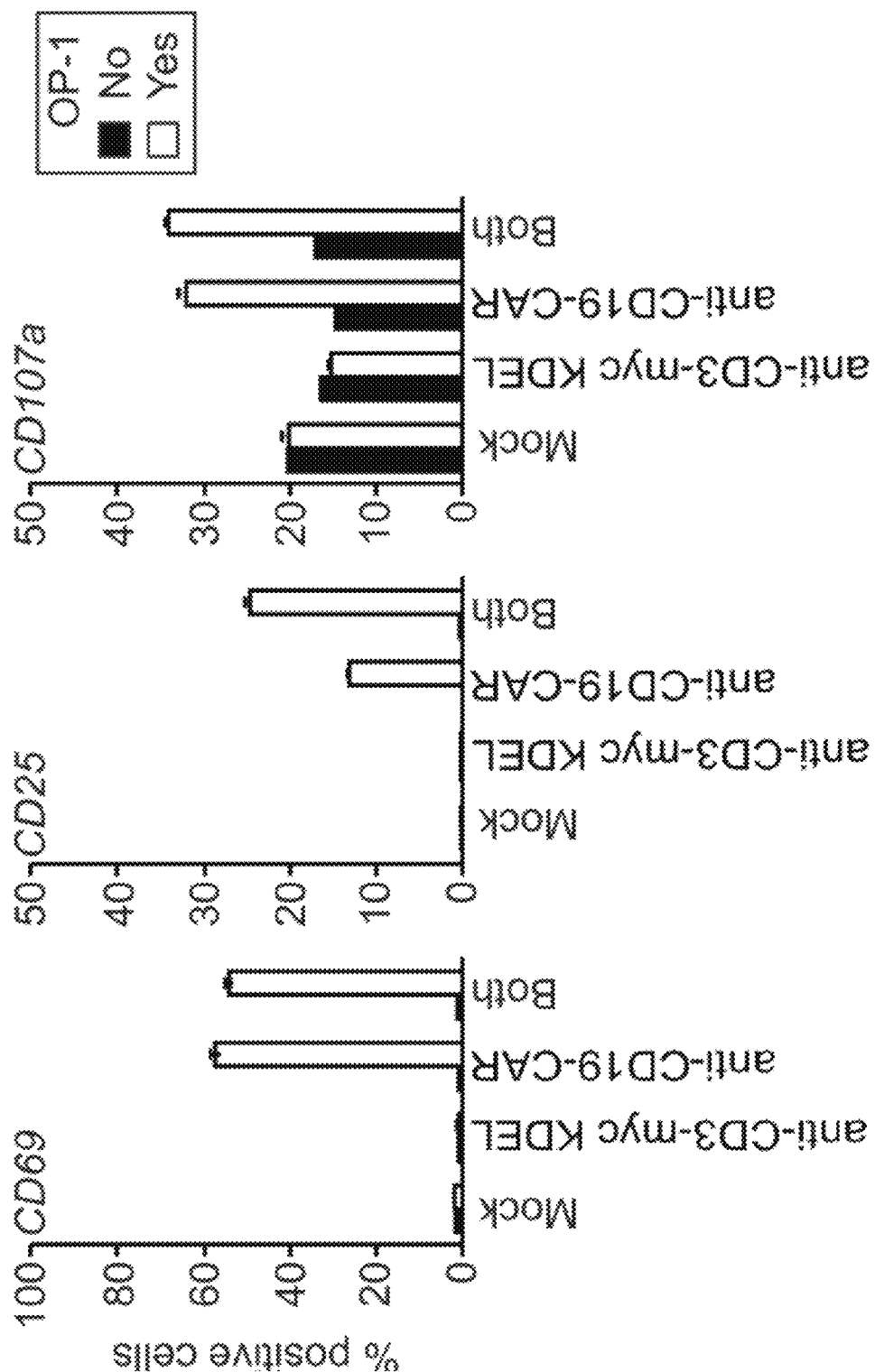
FIG. 6 illustrates that anti-CD19 CAR triggers T cell activation and degranulation regardless of CD3/TCR downregulation. Jurkat cells were transduced with the anti-CD3 scFv-myc KDEL construct, the anti-CD19-4-1BB-CD3ζ construct, or both. T cell activation and degranulation was compared to that of mock-transduced cells. Cells were co-cultured alone or with the CD19+ leukemia cell line OP-1 at a 1:1 ratio. After 18 hours, expression of CD69 and CD25 was tested by flow cytometry using specific antibodies (from BD Biosciences); expression of CD107a was tested after 6 hours (antibody from BD Biosciences). In the presence of OP-1 cells, CD69 and CD25 expression in CAR-expressing cells occurred regardless of whether cells were also transduced with anti-CD3 scFv-KDEL; no activation occurred in mock- or anti-CD3 scFv-myc KDEL transduced cells, or in the absence of OP-1 cells. CAR stimulation enhanced CD107 expression which was not affected by CD3/TCR downregulation.
Figure 7:
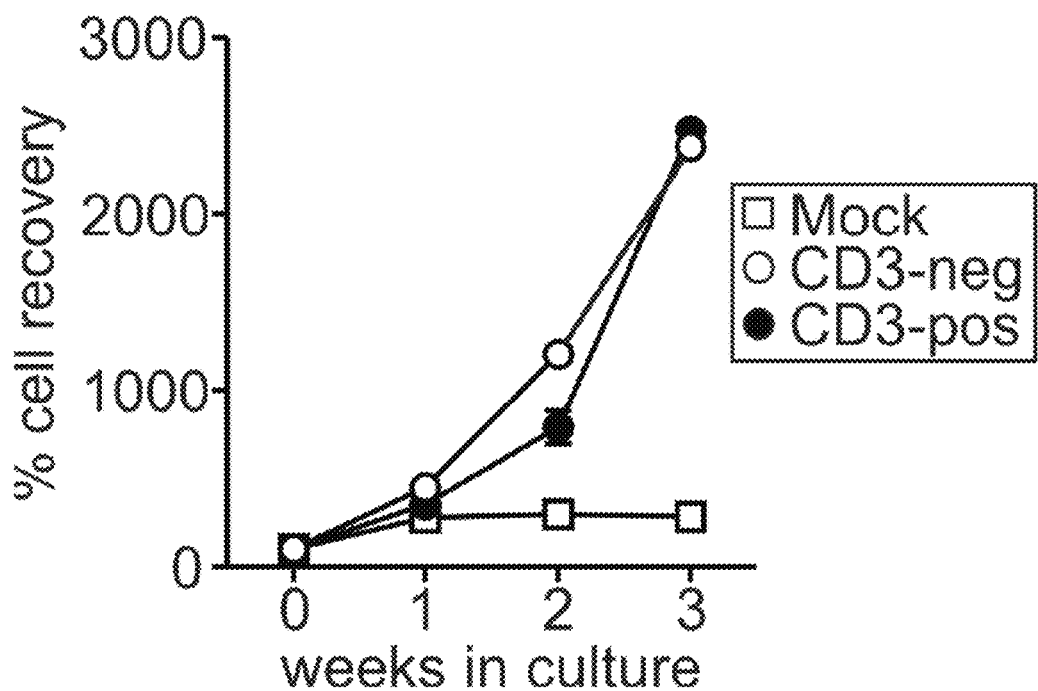
FIG. 7 shows that anti-CD19 CAR expressed in T cells causes T cell proliferation regardless of CD3/TCR downregulation. Peripheral blood T lymphocytes were transduced with both the anti-CD3 scFv-myc KDEL construct and the anti-CD19-4-1BB-CD3ζ construct. Transduced T lymphocytes were co-cultured with OP-1 cells treated with Streck (Omaha, NE) to inhibit their proliferation for the time indicated. Expansion of CD3-positive and CD3-negative T lymphocytes expressing the anti-CD19 CAR was compared to that of mock-transduced T cells. Each symbol shows the average cell count of two parallel cultures. CAR T cell expanded equally well regardless of CD3/TCR expression.

To assess whether CAR could signal in Jurkat cells with downregulated CD3/TCR, the expression of the activation markers CD69 and CD25 was tested, and exocytosis of lytic granules was measured by CD107a expression in Jurkat cells co-cultured with the CD19+ leukemia cell line OP-1. As shown in FIG. 6, downregulation of CD3/TCR with the anti-CD3 scFv-myc KDEL construct did not diminish the capacity of anti-CD19-4-1BB-CD3ζ CAR to activate Jurkat cells. To further explore the effects of CD3/TCR deletion on CAR signaling, it was determined whether CD3-negative T lymphocytes expressing the CAR could be stimulated by its ligation. As shown in FIG. 7, co-culture of T lymphocytes expressing the anti-CD19 CAR with CD19+ leukemic cells led to T cell proliferation regardless of whether CD3 was downregulated or not, indicating that CD3/TCR downregulation did not diminish the CAR proliferative stimulus.

Accordingly, CD3/TCR can be effectively downregulated in CAR-T cells using the anti-CD3 scFv-myc KDEL construct without affecting T cell activation, degranulation and proliferation driven by the CAR.

Downregulation of CD7

Figure 8:
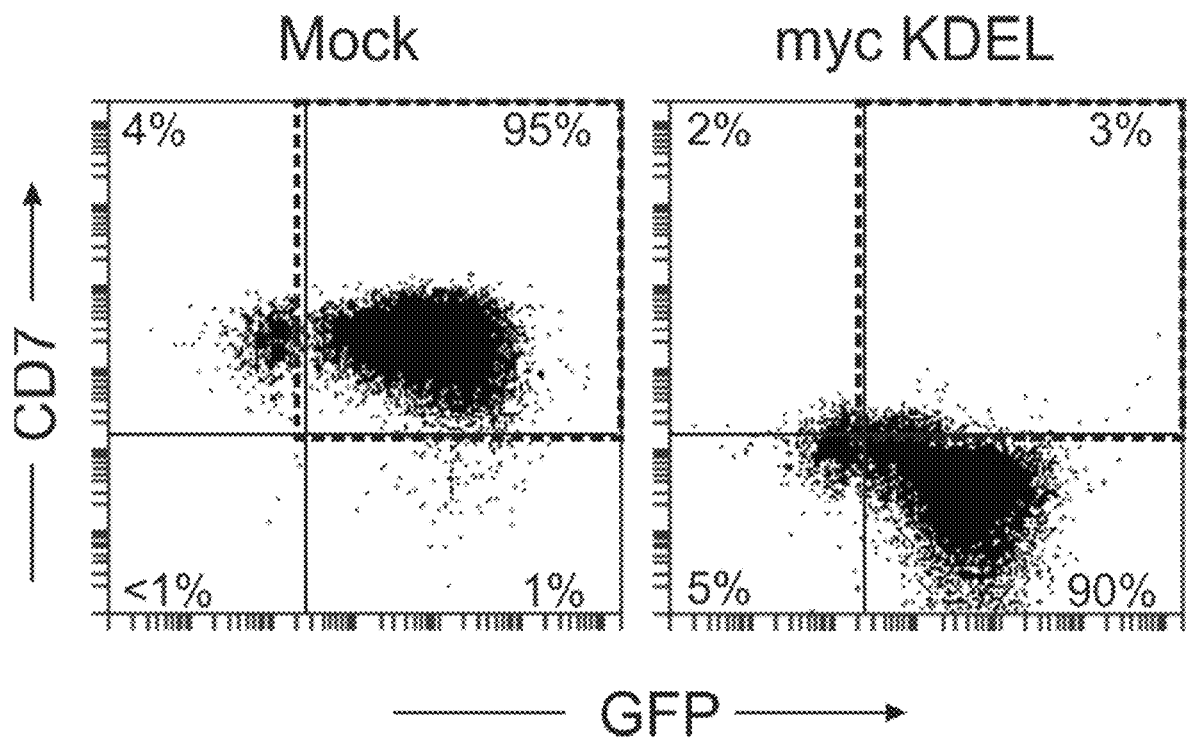
FIG. 8 shows expression of CD7 on the membrane of peripheral blood T lymphocytes transduced with either a retroviral vector containing GFP only ("mock") or a vector containing GFP plus and anti-CD7 scFv-myc KDEL construct. Expression of CD7 on the cell membrane was compared to that of mock-transduced cells 1 week after transduction using an anti-CD7 antibody conjugated to phycoerythrin (BD Biosciences). Dashed rectangles on the upper right quadrant of each plot enclose GFP+CD7+ cells.

It was determined whether the strategy that successfully modulated CD3/TCR expression could be applied to other surface molecules. For this purpose, CD7 expression was modulated. The scFv sequence was derived from that published by Peipp et al. (Cancer Res 2002 (62): 2848-2855), which was linked to the CD8 signal peptide and the myc-KDEL sequence as illustrated in FIG. 2. Using the MSCV retroviral vector, the anti-CD7-myc KDEL construct was transduced in peripheral blood lymphocytes, which have high expression of CD7 as detected by an anti-CD7 antibody conjugated to phycoerythrin (BD Bioscience). As shown in FIG. 8, CD7 in T lymphocytes transduced with the construct was virtually abrogated.

Downregulation of HLA-Class I

The strategy was then applied to downregulate another surface molecule, HLA class I.

HLA class I consists of polymorphic α chains and a non-polymorphic chain termed β2-microglobulin. Knockdown of the latter subunit results in abrogation of HLA (MHC in the mouse) Class I expression (Koller, B H et al., *Science.* 1990; 248(4960):1227-1230). An scFv reacting with β2-microglobulin was used to suppress expression of HLA Class I in immune cells.

Figure 9:
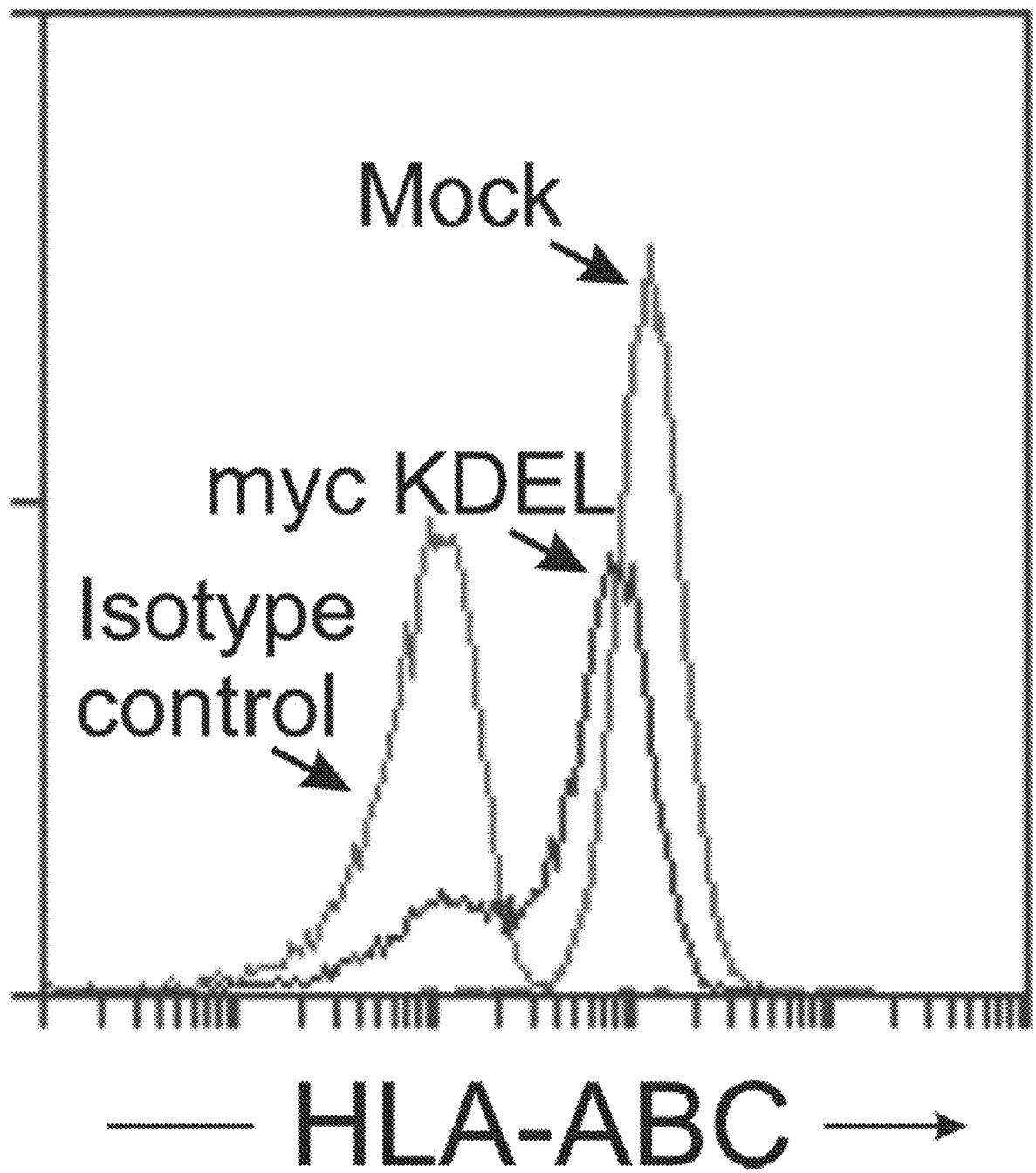
FIG. 9 depicts the downregulation of HLA Class I in T cells by scFv targeting of β2-microglobulin. Jurkat T cells were transduced with anti-β2M scFv-myc KDEL. Expression of HLA-ABC on the cell membrane was compared to that of mock-transduced cells 1 week after transduction using an anti-HLA-ABC antibody conjugated to phycoerythrin (BD Biosciences). Staining with an isotype-matched control antibody is also shown. Analysis was performed after gating on GFP-positive cells.

The scFv sequence was derived from that published by Grovender et al. (*Kidney Int.* 2004; 65(1):310-322), which was linked to the CD8 signal peptide and the myc KDEL sequence as illustrated in FIG. 2. Using the MSCV retroviral vector, the anti-β2M-myc KDEL construct was transduced in Jurkat cells, which have high expression of HLA Class I as detected by an anti-HLA-ABC antibody conjugated to phycoerythrin (BD Pharmingen). As shown in FIG. 9, Jurkat cells transduced with the construct had a substantial downregulation of HLA-ABC expression. Cells maintained their morphology and growth capacity.

Downregulation of Inhibitory Receptors in NK Cells

To determine if the strategy outlined above would also apply to surface molecules expressed in other immune cells, downregulation of function of the inhibitory receptor KIR2DL1, KIR2DL2/DL3 and NKG2A was tested in NK cells.

Figure 10:
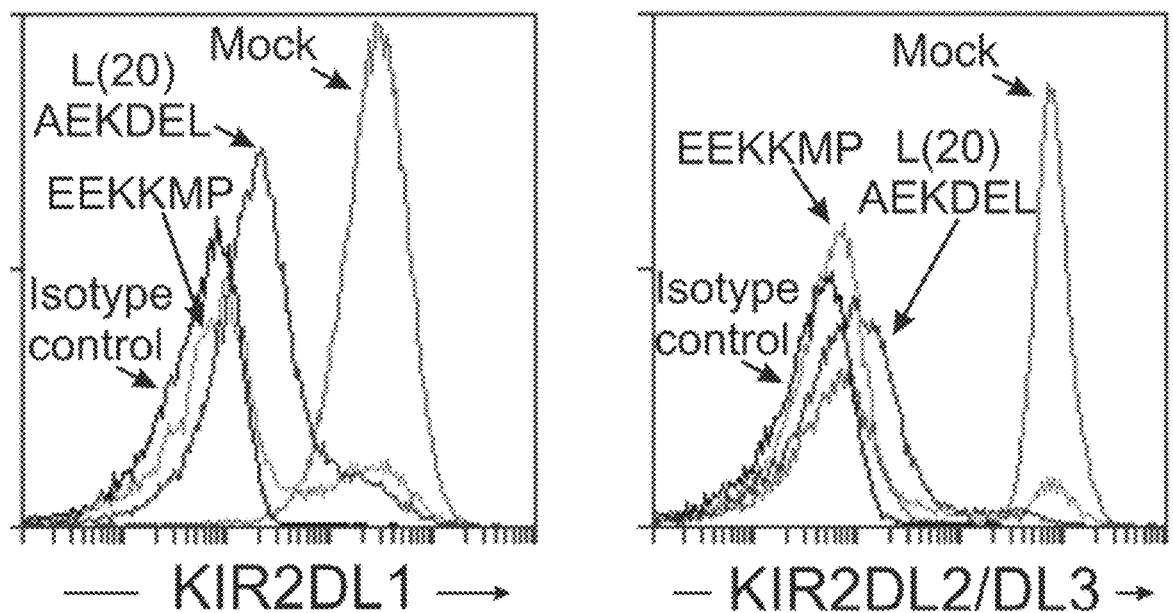
FIG. 10 depicts the downregulation of Killer Immunoglobulin-like Receptor (KIR) 2DL1 and KIR2DL2/DL3 in human NK cells by scFv targeting of KIR2DL1 and KIR2DL2/DL3. NK cells, expanded ex vivo and selected for KIR2DL1 expression, were transduced with anti-KIR2DL1-KIR2DL2/DL3 scFv-linker (20) AEKDEL or -EEKKMP. Expression of the corresponding KIR on the cell membrane was compared to that of mock-transduced cells 8 days after transduction using an anti-KIR2DL1 antibody conjugated to allophycocyanin (R&D Systems) or an anti-KIR2DL2/DL3 antibody conjugated to phycoerythrin (BD Biosciences). Staining with an isotype-matched control antibody is also shown. Analysis was performed after gating on GFP-positive cells.

To downregulate KIR receptors, an scFv reacting with KIR2DL1 and KIR2DL2/DL3 was used to suppress their expression in NK cells. The scFv sequence was derived from that published by Moretta et al. (patent WO2006003179 A2), which was linked to the CD8 signal peptide and the ER retention sequences as illustrated in FIG. 2. Using the MSCV retroviral vector, the constructs were transduced in NK cells expanded from human peripheral blood and selected for KIR2DL1 expression. These cells had high KIR2DL1 expression as detected by an anti-KIR2DL1 antibody conjugated to allophycocyanin (R&D Systems) and also high KIR2DL2/DL3 expression as detected by an anti-KIR2DL2/DL3 antibody conjugated to phycoerythrin (BD Bioscience). FIG. 10 shows results obtained with scFv-linker(20) AEKEDL and scFv-EEKKMP, with substantial down regulation of the targeted KIRs.

Figure 11:
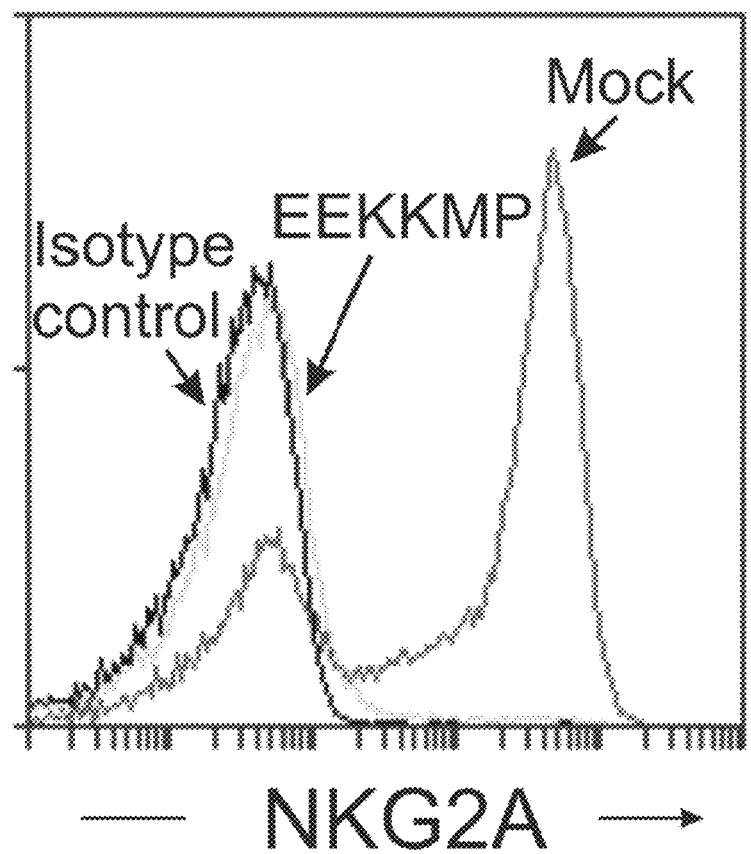
FIG. 11 depicts the downregulation of NKG2A in human NK cells by scFv targeting. NK cells, expanded ex vivo, were transduced with anti-NKG2A scFv-EEKKMP. Expression of NKG2A on the cell membrane was compared to that of mock-transduced cells 8 days after transduction using an NKG2A antibody conjugated to phycoerythrin (Beckman Coulter). Staining with an isotype-matched control antibody is also shown. Analysis was performed after gating on GFP-positive cells.

To downregulate NKG2A, an scFv reacting with NKG2A was used to suppress its expression in NK cells. The scFv sequence, which was derived from published European Patent Application No. EP2247619 A1 by Spee et al. was linked to the CD8 signal peptide and the ER retention sequences as illustrated in FIG. 2. Using the MSCV retroviral vector, the constructs were transduced in NK cells expanded from human peripheral blood, which had high NKG2A expression as detected by an anti-NKG2A antibody conjugated to phycoerythrin (Beckman Coulter). FIG. 11 shows substantial downregulation of NKG2A obtained with scFv-EEKKMP.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. An in vitro method for producing an engineered immune cell, the method comprising: introducing into an immune cell (i) a first polynucleotide sequence encoding an immune activating receptor comprising a first binding domain that binds to a molecule expressed on the surface of a cancer cell, and (ii) a second polynucleotide sequence encoding a target-binding molecule linked to a localizing domain, wherein the target-binding molecule comprises a second binding domain that binds to a target of the immune cell, and wherein the target-binding molecule linked to the localizing domain downregulates expression of the target of the immune cell, thereby producing an engineered immune cell,
   wherein the engineered immune cell retains similar or higher (i) expression of the immune activating receptor, (ii) expression of a T cell activation marker, (iii) T cell proliferation, or (iv) any combination thereof, as compared to that of an otherwise identical immune cell that comprises the first polynucleotide sequence but not the second polynucleotide sequence,
   wherein the second polynucleotide sequence comprises, from 5' terminus to 3' terminus, a first nucleotide sequence encoding the second binding domain, a second nucleotide sequence encoding a peptide linker, and a third nucleotide sequence encoding the localizing domain, and wherein the peptide linker comprises at least 5 amino acids, and
   wherein the molecule expressed on the surface of the cancer cell and the target of the immune cell are the same.

2. The in vitro method of claim 1, wherein the localizing domain 3 comprises an ER retention sequence, a Golgi retention sequence, or a PEST sequence.

3. The in vitro method of claim 1, wherein the first polynucleotide sequence and the second polynucleotide sequence are on the same polynucleotide molecule.

4. The in vitro method of claim 3, further comprising an internal ribosomal entry site or a 2A peptide-coding region site between the first polynucleotide sequence encoding the immune activating receptor and the second polynucleotide sequence encoding the target-binding molecule linked to a localizing domain.

5. The in vitro method of claim 2, wherein the localizing domain comprises an ER retention sequence.

6. The in vitro method of claim 5, wherein the ER retention sequence comprises a KDEL amino acid sequence.

7. The in vitro method of claim 5, wherein the ER retention sequence comprises a KKXX amino acid sequence, wherein X represents any amino acid.

8. The in vitro method of claim 2, wherein the localizing domain comprises a Golgi retention sequence.

9. The in vitro method of claim 8, wherein the Golgi retention sequence comprises a YQRL amino acid sequence.

10. The in vitro method of claim 2, wherein the localizing domain comprises a PEST sequence.

11. The in vitro method of claim 1, wherein the immune cell is a T cell.

12. The in vitro method of claim 1, wherein the immune cell is a natural killer (NK) cell.

13. The in vitro method of claim 1, wherein the second binding domain is a single chain binding domain.

14. The in vitro method of claim 13, wherein the single chain binding domain is a single chain variable fragment (scFv).

15. The in vitro method of claim 1, wherein the target-binding molecule linked to a localizing domain further comprises a transmembrane domain.

16. The in vitro method of claim 15, wherein the transmembrane domain is a CD8 transmembrane domain.

17. The in vitro method of claim 1, wherein the immune activating receptor is a chimeric antigen receptor (CAR) comprising the first binding domain, a signaling domain, and a costimulatory domain.

18. The in vitro method of claim 1, wherein the first binding domain and the second binding domain have the same sequence.

19. The in vitro method of claim 1, wherein the second binding domain and the first binding domain are different.

20. The in vitro method of claim 17, wherein the signaling domain comprises a CD3ζ, a Fc, a DAP10, or a DAP12 domain.

21. The in vitro method of claim 17, wherein the costimulatory domain comprises a 4-1BB domain, a CD28 domain, a $CD28_{LL \rightarrow GG}$ variant domain, an OX40 domain, an ICOS domain, a CD27 domain, a GITR domain, a HVEM domain, a TIM1 domain, a LFA1 domain, or a CD2 domain.

22. The in vitro method of claim 1, wherein the second polynucleotide sequence further comprises a nucleotide sequence encoding a signal peptide.

23. The in vitro method of claim 1, wherein the first binding domain is a first single chain variable fragment (scFv) and the second binding domain is a second scFv.

* * * * *

SEQUENCE LISTING

```
<160> NUMBER OF SEQ ID NOS: 64

<210> SEQ ID NO 1
<211> LENGTH: 10
<212> TYPE: PRT
<213> ORGANISM: Artificial Sequence
<220> FEATURE:
<223> OTHER INFORMATION: Myc tag

<400> SEQUENCE: 1

Glu Gln Lys Leu Ile Ser Glu Glu Asp Leu
1               5                   10

<210> SEQ ID NO 2
<211> LENGTH: 40
<212> TYPE: DNA
<213> ORGANISM: Artificial Sequence
<220> FEATURE:
<223> OTHER INFORMATION: Sense primer
```

<400> SEQUENCE: 2
atatatgaat tcggcttcca ccatggcctt accagtgacc                           40

<210> SEQ ID NO 3
<211> LENGTH: 50
<212> TYPE: DNA
<213> ORGANISM: Artificial Sequence
<220> FEATURE:
<223> OTHER INFORMATION: Reverse primer

<400> SEQUENCE: 3
cagatcttct tcagaaataa gtttttgttc ggctgaggag actgtgagag                50

<210> SEQ ID NO 4
<211> LENGTH: 4
<212> TYPE: PRT
<213> ORGANISM: Artificial Sequence
<220> FEATURE:
<223> OTHER INFORMATION: KDEL coding sequence

<400> SEQUENCE: 4

Lys Asp Glu Leu
1

<210> SEQ ID NO 5
<211> LENGTH: 40
<212> TYPE: DNA
<213> ORGANISM: Artificial Sequence
<220> FEATURE:
<223> OTHER INFORMATION: Sense primer

<400> SEQUENCE: 5
atatatgaat tcggcttcca ccatggcctt accagtgacc                           40

<210> SEQ ID NO 6
<211> LENGTH: 48
<212> TYPE: DNA
<213> ORGANISM: Artificial Sequence
<220> FEATURE:
<223> OTHER INFORMATION: Reverse primer

<400> SEQUENCE: 6
tatatactcg agttacaact cgtccttcag atcttcttca gaaataag                  48

<210> SEQ ID NO 7
<211> LENGTH: 40
<212> TYPE: PRT
<213> ORGANISM: Artificial Sequence
<220> FEATURE:
<223> OTHER INFORMATION: PEST motif

<400> SEQUENCE: 7

Ser His Gly Phe Pro Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40

<210> SEQ ID NO 8
<211> LENGTH: 5
<212> TYPE: PRT
<213> ORGANISM: Artificial Sequence
<220> FEATURE:

<223> OTHER INFORMATION: Hydrophilic peptide

<400> SEQUENCE: 8

Gly Gly Gly Gly Ser
1               5

<210> SEQ ID NO 9
<211> LENGTH: 4
<212> TYPE: PRT
<213> ORGANISM: Artificial Sequence
<220> FEATURE:
<223> OTHER INFORMATION: ER or Golgi retention sequence
<220> FEATURE:
<221> NAME/KEY: VARIANT
<222> LOCATION: 3, 4
<223> OTHER INFORMATION: Xaa = Any Amino Acid

<400> SEQUENCE: 9

Lys Lys Xaa Xaa
1

<210> SEQ ID NO 10
<211> LENGTH: 3
<212> TYPE: PRT
<213> ORGANISM: Artificial Sequence
<220> FEATURE:
<223> OTHER INFORMATION: ER or Golgi retention sequence
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 3
<223> OTHER INFORMATION: Xaa = ASP or GLU

<400> SEQUENCE: 10

Lys Xaa Xaa
1

<210> SEQ ID NO 11
<211> LENGTH: 4
<212> TYPE: PRT
<213> ORGANISM: Artificial Sequence
<220> FEATURE:
<223> OTHER INFORMATION: ER or Golgi retention sequence

<400> SEQUENCE: 11

Tyr Gln Arg Leu
1

<210> SEQ ID NO 12
<211> LENGTH: 120
<212> TYPE: PRT
<213> ORGANISM: Artificial Sequence
<220> FEATURE:
<223> OTHER INFORMATION: Variable heavy region for scFv targeting CD3

<400> SEQUENCE: 12

Glu Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Ala
        115                 120

<210> SEQ ID NO 13
<211> LENGTH: 107
<212> TYPE: PRT
<213> ORGANISM: Artificial Sequence
<220> FEATURE:
<223> OTHER INFORMATION: Variable light region for scFv targeting CD3

<400> SEQUENCE: 13

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 14
<211> LENGTH: 360
<212> TYPE: DNA
<213> ORGANISM: Artificial Sequence
<220> FEATURE:
<223> OTHER INFORMATION: Variable heavy region for scFv targeting CD3

<400> SEQUENCE: 14
gaggtccagc tgcagcagtc tggggctgaa ctggcaagac ctggggcctc agtgaagatg      60
tcctgcaagg cttctggcta cacctttact aggtacacga tgcactgggt aaaacagagg     120
cctggacagg gtctggaatg gattggatac attaatccta gccgtggtta tactaattac     180
aatcagaagt tcaaggacaa ggccacattg actacagaca atcctccag cacagcctac      240 atgcaactga gcagcctgac atctgaggac tctgcagtct attactgtgc aagatattat     300
gatgatcatt actgccttga ctactggggc caaggcacca ctctcacagt ctcctcagcc     360

<210> SEQ ID NO 15
<211> LENGTH: 321
<212> TYPE: DNA
<213> ORGANISM: Artificial Sequence
<220> FEATURE:
<223> OTHER INFORMATION: Variable light region for scFv targeting CD3

<400> SEQUENCE: 15
caaattgttc tcacccagtc tccagcaatc atgtctgcat ctccagggga gaaggtcacc      60
atgacctgca gtgccagctc aagtgtaagt tacatgaact ggtaccagca gaagtcaggc     120

```
acctccccca aaagatggat ttatgacaca tccaaactgg cttctggagt ccctgctcac      180
ttcaggggca gtgggtctgg gacctcttac tctctcacaa tcagcggcat ggaggctgaa      240
gatgctgcca cttattactg ccagcagtgg agtagtaacc cattcacgtt cggctcgggg      300
acaaagttgg aaataaaccg g                                                321
```

```
<210> SEQ ID NO 16
<211> LENGTH: 117
<212> TYPE: PRT
<213> ORGANISM: Artificial Sequence
<220> FEATURE:
<223> OTHER INFORMATION: Variable heavy region for scFv targeting CD7
      (TH69)

<400> SEQUENCE: 16

Glu Val Gln Leu Val Glu Ser Gly Gly Gly Leu Val Lys Pro Gly Gly
1               5                   10                  15

Ser Leu Lys Leu Ser Cys Ala Ala Ser Gly Leu Thr Phe Ser Ser Tyr
            20                  25                  30

Ala Met Ser Trp Val Arg Gln Thr Pro Glu Lys Arg Leu Glu Trp Val
        35                  40                  45

Ala Ser Ile Ser Ser Gly Gly Phe Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Asp Glu Val Arg Gly Tyr Leu Asp Val Trp Gly Ala Gly Thr Thr
            100                 105                 110

Val Thr Val Ser Ser
        115

<210> SEQ ID NO 17
<211> LENGTH: 112
<212> TYPE: PRT
<213> ORGANISM: Artificial Sequence
<220> FEATURE:
<223> OTHER INFORMATION: Variable light region for scFv targeting CD7
      (TH69)

<400> SEQUENCE: 17

Ala Ala Tyr Lys Asp Ile Gln Met Thr Gln Thr Thr Ser Ser Leu Ser
1               5                   10                  15

Ala Ser Leu Gly Asp Arg Val Thr Ile Ser Cys Ser Ala Ser Gln Gly
            20                  25                  30

Ile Ser Asn Tyr Leu Asn Trp Tyr Gln Gln Lys Pro Asp Gly Thr Val
        35                  40                  45

Lys Leu Leu Ile Tyr Tyr Thr Ser Ser Leu His Ser Gly Val Pro Ser
    50                  55                  60

Arg Phe Ser Gly Ser Gly Ser Gly Thr Asp Tyr Ser Leu Thr Ile Ser
65                  70                  75                  80

Asn Leu Glu Pro Glu Asp Ile Ala Thr Tyr Tyr Cys Gln Gln Tyr Ser
                85                  90                  95

Lys Leu Pro Tyr Thr Phe Gly Gly Gly Thr Lys Leu Glu Ile Lys Arg
            100                 105                 110

<210> SEQ ID NO 18
<211> LENGTH: 351
```

<212> TYPE: DNA
<213> ORGANISM: Artificial Sequence
<220> FEATURE:
<223> OTHER INFORMATION: Variable heavy region for scFv targeting CD7
      (TH69)

<400> SEQUENCE: 18

| | |
|---|---|
| gaggtgcagc tggtcgaatc tggaggagga ctggtgaagc caggaggatc tctgaaactg | 60 |
| agttgtgccg cttcaggcct gaccttctca agctacgcca tgagctgggt gcgacagaca | 120 |
| cctgagaagc ggctggaatg ggtcgctagc atctcctctg gcgggttcac atactatcca | 180 |
| gactccgtga aaggcagatt tactatctct cgggataacg caagaaatat tctgtacctg | 240 |
| cagatgagtt cactgaggag cgaggacacc gcaatgtact attgtgccag ggacgaagtg | 300 |
| cgcggctatc tggatgtctg gggagctggc actaccgtca ccgtctccag c | 351 |

<210> SEQ ID NO 19
<211> LENGTH: 336
<212> TYPE: DNA
<213> ORGANISM: Artificial Sequence
<220> FEATURE:
<223> OTHER INFORMATION: Variable light region for scFv targeting CD7
      (TH69)

<400> SEQUENCE: 19

| | |
|---|---|
| gccgcataca aggatattca gatgactcag accacaagct ccctgagcgc ctccctggga | 60 |
| gaccgagtga caatctcttg cagtgcatca cagggaatta gcaactacct gaattggtat | 120 |
| cagcagaagc cagatggcac tgtgaaactg ctgatctact atacctctag tctgcacagt | 180 |
| ggggtcccct cacgattcag cggatccggc tctgggacag actacagcct gactatctcc | 240 |
| aacctggagc cgaagatat tgccacctac tattgccagc agtactccaa gctgccttat | 300 |
| acctttggcg ggggaacaaa gctggagatt aaaagg | 336 |

<210> SEQ ID NO 20
<211> LENGTH: 123
<212> TYPE: PRT
<213> ORGANISM: Artificial Sequence
<220> FEATURE:
<223> OTHER INFORMATION: Variable heavy region for scFv targeting CD7
      (3a1f)

<400> SEQUENCE: 20

Gln Val Gln Leu Gln Glu Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Lys Ile Asn Pro Ser Asn Gly Arg Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Val Tyr Tyr Asp Leu Tyr Tyr Ala Leu Asp Tyr
            100                 105                 110

Trp Gly Gln Gly Thr Thr Val Thr Val Ser Ser
        115                 120

<210> SEQ ID NO 21
<211> LENGTH: 108
<212> TYPE: PRT
<213> ORGANISM: Artificial Sequence
<220> FEATURE:
<223> OTHER INFORMATION: Variable light region for scFv targeting CD7 (3a1f)

<400> SEQUENCE: 21

```
Asp Ile Glu Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Ser Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys Arg
            100                 105
```

<210> SEQ ID NO 22
<211> LENGTH: 369
<212> TYPE: DNA
<213> ORGANISM: Artificial Sequence
<220> FEATURE:
<223> OTHER INFORMATION: Variable heavy region for scFv targeting CD7 (3a1f)

<400> SEQUENCE: 22

```
caggtccagc tgcaggagtc aggggcagag ctggtgaaac ccggagccag tgtcaaactg      60
tcctgtaagg ccagcggcta tactttcacc agctactgga tgcactgggt gaaacagagg     120
ccaggacagg gcctggagtg gatcggcaag attaacccca gcaatgggcg caccaactac     180
aacgaaaagt ttaaatccaa ggctacactg actgtggaca gagctcctc taccgcatac      240 atgcagctga gttcactgac atctgaagat agtgccgtgt actattgcgc cagaggcggg     300
gtctactatg acctgtacta ttacgcactg gattattggg gcagggaac cacagtgact      360 gtcagctcc                                                             369
```

<210> SEQ ID NO 23
<211> LENGTH: 324
<212> TYPE: DNA
<213> ORGANISM: Artificial Sequence
<220> FEATURE:
<223> OTHER INFORMATION: Variable light region for scFv targeting CD7 (3a1f)

<400> SEQUENCE: 23

```
gacatcgagc tgacacagtc tccagccact ctgagcgtga cccctggcga ttctgtcagt      60
ctgtcatgta gagctagcca gtccatctct aacaatctgc actggtacca gcagaaatca     120
catgaaagcc ctcggctgct gattaagagt gcttcacaga gcatctccgg gattccaagc     180
agattctctg gcagtgggtc aggaaccgac tttacactgt ccattaactc tgtggagacc     240
gaagatttcg gcatgtattt ttgccagcag agcaattcct ggccttacac attcggaggc     300
gggactaaac tggagattaa gagg                                            324
```

<210> SEQ ID NO 24
<211> LENGTH: 120
<212> TYPE: PRT
<213> ORGANISM: Artificial Sequence
<220> FEATURE:
<223> OTHER INFORMATION: Variable heavy region for scFv targeting CD45

<400> SEQUENCE: 24

```
Gln Val Gln Leu Val Glu Ser Gly Gly Gly Leu Val Gln Pro Gly Gly
1               5                  10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Thr Ser Ser Thr Ile Asn Phe Thr Pro Ser Leu
    50                  55                  60

Lys Asp Lys Val Phe Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Gly Asn Tyr Tyr Arg Tyr Gly Asp Ala Met Asp Tyr Trp Gly
            100                 105                 110

Gln Gly Thr Ser Val Thr Val Ser
        115                 120
```

<210> SEQ ID NO 25
<211> LENGTH: 111
<212> TYPE: PRT
<213> ORGANISM: Artificial Sequence
<220> FEATURE:
<223> OTHER INFORMATION: Variable light region for scFv targeting CD45

<400> SEQUENCE: 25

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys
            100                 105                 110
```

<210> SEQ ID NO 26
<211> LENGTH: 360
<212> TYPE: DNA
<213> ORGANISM: Artificial Sequence
<220> FEATURE:
<223> OTHER INFORMATION: Variable heavy region for scFv targeting CD45

<400> SEQUENCE: 26

```
caggtgcagc tggtcgagtc tggaggagga ctggtgcagc ctggaggaag tctgaagctg      60
tcatgtgcag ccagcgggtt cgactttct cgatactgga tgagttgggt gcggcaggca     120
```

```
ccaggaaaag gactggaatg gatcggcgag attaacccaa ctagctccac catcaatttc      180
acacccagcc tgaaggacaa agtgtttatt tccagagata cgccaagaa tactctgtat       240 ctgcagatgt ccaaagtcag gtctgaagat accgccctgt actattgtgc tcggggcaac      300
tactatagat acggggacgc tatggattat tggggggcagg aactagcgt gaccgtgagt      360
```

<210> SEQ ID NO 27
<211> LENGTH: 333
<212> TYPE: DNA
<213> ORGANISM: Artificial Sequence
<220> FEATURE:
<223> OTHER INFORMATION: Variable light region for scFv targeting CD45

<400> SEQUENCE: 27

```
gacattgtgc tgacccagtc ccctgcttca ctggcagtga gcctgggaca gagggcaacc      60
atcagctgcc gagcctctaa gagtgtctca acaagcggat actcctatct gcactggtac      120
cagcagaagc caggacagcc acctaaactg ctgatctatc tggcttccaa cctggaatct      180
ggagtgcctg cacgcttctc cggatctgga agtggaaccg acttacact gaatattcac       240 ccagtcgagg aagaggatgc cgctacctac tattgccagc acagccggga gctgcccttc      300
acatttggca gcgggactaa gctggagatc aag                                   333
```

<210> SEQ ID NO 28
<211> LENGTH: 119
<212> TYPE: PRT
<213> ORGANISM: Artificial Sequence
<220> FEATURE:
<223> OTHER INFORMATION: Variable heavy region for scFv targeting B2MG

<400> SEQUENCE: 28

```
Glu Val Gln Leu Gln Gln Ser Gly Ala Glu Leu Val Lys Pro Gly Ala
1               5                   10                  15

Ser Val Lys Leu Ser Cys Thr Pro Ser Gly Phe Asn Val Lys Asp Thr
            20                  25                  30

Tyr Ile His Trp Val Lys Gln Arg Pro Lys Gln Gly Leu Glu Trp Ile
        35                  40                  45

Gly Arg Ile Asp Pro Ser Asp Gly Asp Ile Lys Tyr Asp Pro Lys Phe
    50                  55                  60

Gln Gly Lys Ala Thr Ile Thr Ala Asp Thr Ser Ser Asn Thr Val Ser
65                  70                  75                  80

Leu Gln Leu Ser Ser Leu Thr Ser Glu Asp Thr Ala Val Tyr Tyr Cys
                85                  90                  95

Ala Arg Trp Phe Gly Asp Tyr Gly Ala Met Asn Tyr Trp Gly Gln Gly
            100                 105                 110

Thr Ser Val Thr Val Ser Ser
        115
```

<210> SEQ ID NO 29
<211> LENGTH: 110
<212> TYPE: PRT
<213> ORGANISM: Artificial Sequence
<220> FEATURE:
<223> OTHER INFORMATION: Variable light region for scFv targeting B2MG

<400> SEQUENCE: 29

```
Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30
```

Leu Ala Trp Tyr Gln Gln Lys Pro Gly Lys Ser Pro Gln Leu Leu Ile
            35                  40                  45

Tyr Ala Ala Thr Ser Leu Ala Asp Gly Val Pro Ser Arg Phe Ser Gly
        50                  55                  60

Ser Gly Ser Gly Thr Lys Phe Ser Leu Lys Ile Arg Thr Leu Gln Ala
65                  70                  75                  80

Glu Asp Phe Val Ser Tyr Tyr Cys Gln Gln Leu Tyr Ser Lys Pro Tyr
                85                  90                  95

Thr Phe Gly Gly Gly Thr Lys Leu Glu Ile Lys Arg Ala Asp
            100                 105                 110

<210> SEQ ID NO 30
<211> LENGTH: 357
<212> TYPE: DNA
<213> ORGANISM: Artificial Sequence
<220> FEATURE:
<223> OTHER INFORMATION: Variable heavy region for scFv targeting B2MG

<400> SEQUENCE: 30
gaggtgcagc tgcagcagag cggagcagaa ctggtgaaac ctggagccag cgtcaagctg       60
tcctgtactc catctggctt caacgtgaag gacacataca ttcactgggt caagcagcgg      120
cccaaacagg gactggagtg gatcggcaga attgacccat ccgacggcga tatcaagtat      180
gatcccaaat tccaggggaa ggctactatt accgcagata ccagctccaa cacagtgagt      240
ctgcagctgt ctagtctgac tagcgaagac accgccgtct actattgtgc tagatggttt      300
ggcgattacg gggccatgaa ttattggggg cagggaacca gcgtcaccgt gtccagc        357

<210> SEQ ID NO 31
<211> LENGTH: 330
<212> TYPE: DNA
<213> ORGANISM: Artificial Sequence
<220> FEATURE:
<223> OTHER INFORMATION: Variable light region for scFv targeting B2MG

<400> SEQUENCE: 31
gatattcaga tgacccagtc ccctgcatca cagagcgcct ccctgggcga gtcagtgacc       60
atcacatgcc tggctagcca gacaattggc acttggctgg catggtacca gcagaagccc      120
ggcaaatccc ctcagctgct gatctatgca gctacctctc tggcagacgg agtgcccagt      180
aggttctctg ggagtggatc aggcaccaag ttttctctga aaattcgcac actgcaggct      240
gaggatttcg tctcctacta ttgccagcag ctgtactcta aaccttatac atttggcggg      300
ggaactaagc tggaaatcaa acgagcagac                                       330

<210> SEQ ID NO 32
<211> LENGTH: 119
<212> TYPE: PRT
<213> ORGANISM: Artificial Sequence
<220> FEATURE:
<223> OTHER INFORMATION: Variable heavy region for scFv targeting NKG2A

<400> SEQUENCE: 32

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ser Pro Glu Lys Arg Leu Glu Trp Val
        35                  40                  45

```
Ala Glu Ile Ser Ser Gly Gly Ser Tyr Thr Tyr Tyr Pro Asp Thr Val
     50                  55                  60

Thr Gly Arg Phe Thr Ile Ser Arg Asp Asn Ala Lys Asn Thr Leu Tyr
 65                  70                  75                  80

Leu Glu Ile Ser Ser Leu Arg Ser Glu Asp Thr Ala Met Tyr Tyr Cys
                 85                  90                  95

Thr Arg His Gly Asp Tyr Pro Arg Phe Phe Asp Val Trp Gly Ala Gly
            100                 105                 110

Thr Thr Val Thr Val Ser Ser
            115
```

```
<210> SEQ ID NO 33
<211> LENGTH: 107
<212> TYPE: PRT
<213> ORGANISM: Artificial Sequence
<220> FEATURE:
<223> OTHER INFORMATION: Variable light region for scFv targeting NKG2A

<400> SEQUENCE: 33

Gln Ile Val Leu Thr Gln Ser Pro Ala Leu Met Ser Ala Ser Pro Gly
  1               5                  10                  15

Glu Lys Val Thr Met Thr Cys Ser Ala Ser Ser Val Ser Tyr Ile
                 20                  25                  30

Tyr Trp Tyr Gln Gln Lys Pro Arg Ser Ser Pro Lys Pro Trp Ile Tyr
             35                  40                  45

Leu Thr Ser Asn Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Gly Asn Pro Tyr Thr
                 85                  90                  95

Phe Gly Gly Gly Thr Lys Leu Glu Ile Lys Arg
            100                 105
```

```
<210> SEQ ID NO 34
<211> LENGTH: 357
<212> TYPE: DNA
<213> ORGANISM: Artificial Sequence
<220> FEATURE:
<223> OTHER INFORMATION: Variable heavy region for scFv targeting NKG2A

<400> SEQUENCE: 34
gaggtgcagc tggtggagag cggaggagga ctggtgaagc caggaggaag cctgaagctg      60
tcctgtgccg cctctggctt cacatttttcc tcttatgcaa tgagctgggt gcggcagtcc    120
ccagagaaga gactggagtg ggtggcagag atcagctccg gaggatccta cacctactat    180
cctgacacag tgaccggccg gttcacaatc tctagagata cgccaagaa taccctgtat     240 ctggagatct ctagcctgag atccgaggat acagccatgt actattgcac caggcacggc    300
gactacccac gcttctttga cgtgtgggga gcaggaacca cagtgaccgt gtcctct      357
```

```
<210> SEQ ID NO 35
<211> LENGTH: 321
<212> TYPE: DNA
<213> ORGANISM: Artificial Sequence
<220> FEATURE:
<223> OTHER INFORMATION: Variable light region for scFv targeting NKG2A

<400> SEQUENCE: 35
cagattgtcc tgacccagtc tccagccctg atgagcgcct cccctggcga aaggtgaca      60
```

```
atgacctgct ctgccagctc ctctgtgagc tacatctatt ggtaccagca gaagcctcgg    120
agctccccaa agccctggat ctatctgaca tccaacctgg cctctggcgt gccagccaga    180
ttctctggca gcggctccgg cacatcttac agcctgacca tctctagcat ggaggccgag    240
gacgccgcca cctactattg ccagcagtgg tccggcaatc catatacatt tggcggcggc    300
accaagctgg agatcaagag g                                              321
```

```
<210> SEQ ID NO 36
<211> LENGTH: 122
<212> TYPE: PRT
<213> ORGANISM: Artificial Sequence
<220> FEATURE:
<223> OTHER INFORMATION: Variable heavy region for scFv targeting
      KIR2DL1 and 2/3

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Phe Tyr
                20                  25                  30

Ala Ile Ser Trp Val Arg Gln Ala Pro Gly Gln Gly Leu Glu Trp Met
            35                  40                  45

Gly Gly Phe Ile Pro Ile Phe Gly Ala Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Pro Ser Gly Ser Tyr Tyr Tyr Asp Tyr Asp Met Asp Val Trp
            100                 105                 110

Gly Gln Gly Thr Thr Val Thr Val Ser Ser
        115                 120
```

```
<210> SEQ ID NO 37
<211> LENGTH: 109
<212> TYPE: PRT
<213> ORGANISM: Artificial Sequence
<220> FEATURE:
<223> OTHER INFORMATION: Variable light region for scFv targeting
      KIR2DL1 and 2/3

<400> SEQUENCE: 37

Glu Ile Val Leu Thr Gln Ser Pro Val Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Met Tyr
                85                  90                  95

Thr Phe Gly Gln Gly Thr Lys Leu Glu Ile Lys Arg Thr
            100                 105
```

```
<210> SEQ ID NO 38
<211> LENGTH: 369
<212> TYPE: DNA
<213> ORGANISM: Artificial Sequence
<220> FEATURE:
<223> OTHER INFORMATION: Variable heavy region for scFv targeting
      KIR2DL1 and 2/3

<400> SEQUENCE: 38
caggtccagc tggtgcagtc tggagctgaa gtgaagaaac cagggagctc cgtcaaggtg        60
tcatgcaaag caagcggcgg gactttctcc ttttatgcaa tctcttgggt gagacaggca       120
cctggacagg gactggagtg gatgggaggc ttcatcccaa ttttggagc cgctaactat        180 gcccagaagt tccagggcag ggtgaccatc acagctgatg agtctactag taccgcatac       240
atggaactgt ctagtctgag gagcgacgat accgccgtgt actattgtgc tcgcattcca       300
tcaggcagct actattacga ctatgatatg gacgtgtggg gccaggggac cacagtcacc       360
gtgagcagc                                                                369

<210> SEQ ID NO 39
<211> LENGTH: 327
<212> TYPE: DNA
<213> ORGANISM: Artificial Sequence
<220> FEATURE:
<223> OTHER INFORMATION: Variable light region for scFv targeting
      KIR2DL1 and 2/3

<400> SEQUENCE: 39
gagatcgtgc tgacccagtc tcctgtcaca ctgagtctgt caccagggga acgggctaca        60
ctgtcttgca gagcaagcca gtccgtgagc tcctacctgg cctggtatca gcagaagcca       120
ggccaggctc ccaggctgct gatctacgat gcaagcaaca gggccactgg gattcccgcc       180
cgcttctctg gcagtgggtc aggaaccgac tttactctga ccatttctag tctggagcct       240
gaagatttcg ccgtgtacta ttgccagcag cgatccaatt ggatgtatac ttttggccag       300
gggaccaagc tggagatcaa acggaca                                            327

<210> SEQ ID NO 40
<211> LENGTH: 21
<212> TYPE: PRT
<213> ORGANISM: Artificial Sequence
<220> FEATURE:
<223> OTHER INFORMATION: CD8 signal peptide

<400> SEQUENCE: 40

Met Ala Leu Pro Val Thr Ala Leu Leu Leu Pro Leu Ala Leu Leu Leu
1               5                   10                  15

His Ala Ala Arg Pro
            20

<210> SEQ ID NO 41
<211> LENGTH: 20
<212> TYPE: PRT
<213> ORGANISM: Artificial Sequence
<220> FEATURE:
<223> OTHER INFORMATION: Variable heavy-variable light linker

<400> SEQUENCE: 41

Gly Gly Gly Gly Ser Gly Gly Gly Gly Ser Gly Gly Gly Gly Ser Gly
1               5                   10                  15

Gly Gly Gly Ser
            20
```

<210> SEQ ID NO 42
<211> LENGTH: 70
<212> TYPE: PRT
<213> ORGANISM: Artificial Sequence
<220> FEATURE:
<223> OTHER INFORMATION: CD8 hinge and transmembrane

<400> SEQUENCE: 42

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Val Ile Thr Leu Tyr
65                  70
```

<210> SEQ ID NO 43
<211> LENGTH: 15
<212> TYPE: PRT
<213> ORGANISM: Artificial Sequence
<220> FEATURE:
<223> OTHER INFORMATION: Variable heavy-variable light linker

<400> SEQUENCE: 43

```
Gly Gly Gly Gly Ser Gly Gly Gly Gly Ser Gly Gly Gly Gly Ser
1               5                   10                  15
```

<210> SEQ ID NO 44
<211> LENGTH: 63
<212> TYPE: DNA
<213> ORGANISM: Artificial Sequence
<220> FEATURE:
<223> OTHER INFORMATION: CD8 signal peptide

<400> SEQUENCE: 44

```
atggccttac cagtgaccgc cttgctcctg ccgctggcct tgctgctcca cgccgccagg    60
ccg                                                                 63
```

<210> SEQ ID NO 45
<211> LENGTH: 63
<212> TYPE: DNA
<213> ORGANISM: Artificial Sequence
<220> FEATURE:
<223> OTHER INFORMATION: CD8 signal peptide

<400> SEQUENCE: 45

```
atggctctgc ctgtgaccgc actgctgctg cccctggctc tgctgctgca cgccgcaaga    60
cct                                                                 63
```

<210> SEQ ID NO 46
<211> LENGTH: 63
<212> TYPE: DNA
<213> ORGANISM: Artificial Sequence
<220> FEATURE:
<223> OTHER INFORMATION: CD8 signal peptide

<400> SEQUENCE: 46

```
atggctctgc ccgtcaccgc tctgctgctg cctctggctc tgctgctgca cgctgctcga    60
cca                                                                 63
```

<210> SEQ ID NO 47
<211> LENGTH: 63
<212> TYPE: DNA
<213> ORGANISM: Artificial Sequence
<220> FEATURE:
<223> OTHER INFORMATION: CD8 signal peptide

<400> SEQUENCE: 47

```
atggctctgc cgtgaccgc tctgctgctg cctctggctc tgctgctgca tgctgctcga    60
cct                                                                  63
```

<210> SEQ ID NO 48
<211> LENGTH: 63
<212> TYPE: DNA
<213> ORGANISM: Artificial Sequence
<220> FEATURE:
<223> OTHER INFORMATION: CD8 signal peptide

<400> SEQUENCE: 48

```
atggccctgc cgtcaccgc cctgctgctg ccctggctc tgctgctgca cgccgcaaga     60
ccc                                                                  63
```

<210> SEQ ID NO 49
<211> LENGTH: 63
<212> TYPE: DNA
<213> ORGANISM: Artificial Sequence
<220> FEATURE:
<223> OTHER INFORMATION: CD8 signal peptide

<400> SEQUENCE: 49

```
atggctctgc cgtgaccgc cctgctgctg cctctggctc tgctgctgca cgctgcccgc    60
cca                                                                  63
```

<210> SEQ ID NO 50
<211> LENGTH: 68
<212> TYPE: PRT
<213> ORGANISM: Artificial Sequence
<220> FEATURE:
<223> OTHER INFORMATION: CD8 hinge and transmembrane

<400> SEQUENCE: 50

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr
65
```

<210> SEQ ID NO 51
<211> LENGTH: 60
<212> TYPE: DNA
<213> ORGANISM: Artificial Sequence
<220> FEATURE:
<223> OTHER INFORMATION: Variable heavy-variable light linker

<400> SEQUENCE: 51

```
ggtggtggtg gttctggtgg tgtggttct ggcggcggcg gctccggtgg tgtggatcc     60
```

<210> SEQ ID NO 52
<211> LENGTH: 60
<212> TYPE: DNA
<213> ORGANISM: Artificial Sequence
<220> FEATURE:
<223> OTHER INFORMATION: Variable heavy-variable light linker

<400> SEQUENCE: 52
ggaggaggag gaagcggagg aggaggatcc ggaggcgggg gatctggagg aggaggaagt    60

<210> SEQ ID NO 53
<211> LENGTH: 45
<212> TYPE: DNA
<213> ORGANISM: Artificial Sequence
<220> FEATURE:
<223> OTHER INFORMATION: Variable heavy-variable light linker

<400> SEQUENCE: 53
ggaggaggag gatccggcgg aggaggctct gggggaggcg ggagt    45

<210> SEQ ID NO 54
<211> LENGTH: 60
<212> TYPE: DNA
<213> ORGANISM: Artificial Sequence
<220> FEATURE:
<223> OTHER INFORMATION: Variable heavy-variable light linker

<400> SEQUENCE: 54
ggaggaggag gaagtggagg aggaggatca ggaggcgggg gaagcggcgg gggaggctcc    60

<210> SEQ ID NO 55
<211> LENGTH: 60
<212> TYPE: DNA
<213> ORGANISM: Artificial Sequence
<220> FEATURE:
<223> OTHER INFORMATION: Variable heavy-variable light linker

<400> SEQUENCE: 55
ggaggaggag gaagtggagg aggagggtca ggaggcgggg gaagcggcgg gggaggatcc    60

<210> SEQ ID NO 56
<211> LENGTH: 60
<212> TYPE: DNA
<213> ORGANISM: Artificial Sequence
<220> FEATURE:
<223> OTHER INFORMATION: Variable heavy-variable light linker

<400> SEQUENCE: 56
ggaggaggag gatctggagg aggaggcagc ggcggcggcg gctccggcgg cggcggctct    60

<210> SEQ ID NO 57
<211> LENGTH: 210
<212> TYPE: DNA
<213> ORGANISM: Artificial Sequence
<220> FEATURE:
<223> OTHER INFORMATION: CD8 hinge and transmembrane

<400> SEQUENCE: 57
aagcccacca cgacgccagc gccgcgacca ccaacaccgg cgcccaccat cgcgtcgcag    60
cccctgtccc tgcgcccaga ggcgtgccgg ccagcggcgg ggggcgcagt gcacacgagg   120
gggctggact cgcctgtgta tatctacatc tgggcgccct ggccgggac ttgtggggtc   180 cttctcctgt cactggttat cacccttta                                    210

```
<210> SEQ ID NO 58
<211> LENGTH: 204
<212> TYPE: DNA
<213> ORGANISM: Artificial Sequence
<220> FEATURE:
<223> OTHER INFORMATION: CD8 hinge and transmembrane

<400> SEQUENCE: 58
accactacac ctgcaccaag gcctcccaca cccgctccca ctatcgcttc ccagccactg      60
tccctgaggc ccgaggcctg caggccagca gctggcggag ccgtgcatac taggggctg     120 gacttcgctt gcgacatcta catctgggcc ccactggcag ggacatgcgg agtcctgctg    180
ctgtccctgg tcatcacact ttac                                           204

<210> SEQ ID NO 59
<211> LENGTH: 204
<212> TYPE: DNA
<213> ORGANISM: Artificial Sequence
<220> FEATURE:
<223> OTHER INFORMATION: CD8 hinge and transmembrane

<400> SEQUENCE: 59
actaccacac cagctccaag accacctacc cctgcaccaa caattgctag tcagccactg      60
tcactgagac cagaagcatg taggcctgca gctggaggag ctgtgcacac cagaggcctg    120
gactttgcct gcgatatcta catttgggct cctctggcag gaacctgtgg cgtgctgctg    180
ctgtctctgg tcatcacact ttac                                           204

<210> SEQ ID NO 60
<211> LENGTH: 210
<212> TYPE: DNA
<213> ORGANISM: Artificial Sequence
<220> FEATURE:
<223> OTHER INFORMATION: CD8 hinge and transmembrane

<400> SEQUENCE: 60
aagccaacca caaccctgc accaaggcca cctacaccag cacctaccat cgcaagccag       60
ccactgtccc tgaggccaga ggcatgtagg cctgcagcag gaggcgccgt gcacacacgc    120
ggcctggact ttgcctgcga tatctacatc tgggcaccac tggcaggaac ctgtggcgtg    180
ctgctgctga gcctggtgat taccctgtat                                     210

<210> SEQ ID NO 61
<211> LENGTH: 30
<212> TYPE: DNA
<213> ORGANISM: Artificial Sequence
<220> FEATURE:
<223> OTHER INFORMATION: Variable heavy-variable light linker

<400> SEQUENCE: 61
ggtggtggcg gcagtggtgg cggtggctca                                      30

<210> SEQ ID NO 62
<211> LENGTH: 10
<212> TYPE: PRT
<213> ORGANISM: Artificial Sequence
<220> FEATURE:
<223> OTHER INFORMATION: Variable heavy-variable light linker

<400> SEQUENCE: 62

Gly Gly Gly Gly Ser Gly Gly Gly Gly Ser
1               5                   10
```

```
<210> SEQ ID NO 63
<211> LENGTH: 60
<212> TYPE: DNA
<213> ORGANISM: Artificial Sequence
<220> FEATURE:
<223> OTHER INFORMATION: Variable heavy-variable light linker

<400> SEQUENCE: 63
ggtggtggcg gcagtggtgg cggtggctca ggcggtggtg gctccggtgg cggtggctct    60

<210> SEQ ID NO 64
<211> LENGTH: 6
<212> TYPE: PRT
<213> ORGANISM: Artificial Sequence
<220> FEATURE:
<223> OTHER INFORMATION: Variable heavy-variable light linker

<400> SEQUENCE: 64

Glu Glu Lys Lys Met Pro
1               5
```